United States Patent
D'Souza

(10) Patent No.: US 10,463,608 B2
(45) Date of Patent: Nov. 5, 2019

(54) MICRONEEDLE-BASED TRANSDERMAL DELIVERY SYSTEM AND METHOD OF MAKING SAME

(71) Applicant: THE CORPORATION OF MERCER UNIVERSITY, Macon, GA (US)

(72) Inventor: Martin J. D'Souza, Duluth, GA (US)

(73) Assignee: THE CORPORATION OF MERCER UNIVERSITY, Macon, GA (US)

( * ) Notice: Subject to any disclaimer, the term of this patent is extended or adjusted under 35 U.S.C. 154(b) by 0 days.

(21) Appl. No.: 15/350,718

(22) Filed: Nov. 14, 2016

(65) Prior Publication Data

US 2017/0157036 A1 Jun. 8, 2017

Related U.S. Application Data

(63) Continuation-in-part of application No. 14/874,978, filed on Oct. 5, 2015, now Pat. No. 10,004,790, which is a continuation-in-part of application No. 12/569,867, filed on Sep. 29, 2009, now Pat. No. 9,149,441.

(60) Provisional application No. 61/100,886, filed on Sep. 29, 2008.

(51) Int. Cl.

| | |
|---|---|
| *A61K 9/00* | (2006.01) |
| *A61K 9/16* | (2006.01) |
| *A61K 39/095* | (2006.01) |
| *A61K 39/00* | (2006.01) |
| *C12N 7/00* | (2006.01) |
| *A61K 39/145* | (2006.01) |
| *A61K 39/12* | (2006.01) |
| *A61K 39/155* | (2006.01) |
| *A61M 37/00* | (2006.01) |
| *B29C 41/00* | (2006.01) |
| *B29C 41/04* | (2006.01) |
| *A61K 39/165* | (2006.01) |
| *A61K 39/39* | (2006.01) |
| *A61K 31/727* | (2006.01) |
| *C12N 5/071* | (2010.01) |
| *C12N 15/88* | (2006.01) |
| *B29C 33/42* | (2006.01) |
| *B29C 39/02* | (2006.01) |
| *A61K 35/39* | (2015.01) |
| *B29K 29/00* | (2006.01) |
| *B29K 105/00* | (2006.01) |
| *B29L 31/00* | (2006.01) |

(52) U.S. Cl.
CPC .......... *A61K 9/0021* (2013.01); *A61K 9/1652* (2013.01); *A61K 31/727* (2013.01); *A61K 39/0008* (2013.01); *A61K 39/0011* (2013.01); *A61K 39/095* (2013.01); *A61K 39/12* (2013.01); *A61K 39/145* (2013.01); *A61K 39/155* (2013.01); *A61K 39/165* (2013.01); *A61K 39/39* (2013.01); *A61M 37/0015* (2013.01); *B29C 33/42* (2013.01); *B29C 39/023* (2013.01); *B29C 41/003* (2013.01); *B29C 41/04* (2013.01); *C12N 5/0677* (2013.01); *C12N 7/00* (2013.01); *C12N 15/88* (2013.01); *A61K 35/39* (2013.01); *A61K 2039/5252* (2013.01); *A61K 2039/54* (2013.01); *A61M 2037/003* (2013.01); *A61M 2037/0061* (2013.01); *B29K 2029/04* (2013.01); *B29K 2105/0035* (2013.01); *B29L 2031/7544* (2013.01); *C12N 2710/20023* (2013.01); *C12N 2710/20034* (2013.01); *C12N 2760/16034* (2013.01); *C12N 2760/18534* (2013.01)

(58) Field of Classification Search
None
See application file for complete search history.

(56) References Cited

U.S. PATENT DOCUMENTS

| | | |
|---|---|---|
| 3,137,631 A | 6/1964 | Soloway |
| 3,202,731 A | 8/1965 | Grevenstuk et al. |
| 3,429,827 A | 2/1969 | Ruus |
| 3,663,685 A | 5/1972 | Evans |
| 3,663,686 A | 5/1972 | Grotenhuis et al. |
| 3,663,687 A | 5/1972 | Evans |
| 3,758,678 A | 9/1973 | Lindsay et al. |
| 3,937,668 A | 2/1976 | Zolle |
| 3,962,414 A | 6/1976 | Michaels |
| 4,147,767 A | 4/1979 | Yapel, Jr. |
| 4,169,804 A | 10/1979 | Yapel, Jr. |
| 4,186,183 A | 1/1980 | Steck et al. |

(Continued)

FOREIGN PATENT DOCUMENTS

| | | |
|---|---|---|
| JP | H09506109 A | 6/1997 |
| JP | H10506406 A | 6/1998 |

(Continued)

OTHER PUBLICATIONS

Bhowmik et al., A novel microparticulate vaccine for melanoma cancer using transdermal delivery, J Microencapsul., May 17, 2011, vol. 28, No. 4, pp. 294-300.

(Continued)

*Primary Examiner* — Anand U Desai
(74) *Attorney, Agent, or Firm* — Barnes & Thornburg LLP; Jason Bernstein

(57) ABSTRACT

A transdermal delivery system of microneedles containing a bioactive material, comprising at least one layer of a support material; at least one biodegradable needle associated with the support material, each needle comprising at least one biodegradable polymer and at least one sugar, wherein each biodegradable needle is hollow and is adapted to retain a bioactive material.

12 Claims, 28 Drawing Sheets

(56) References Cited

U.S. PATENT DOCUMENTS

| | | | |
|---|---|---|---|
| 4,230,687 A | 10/1980 | Sair et al. | |
| 4,349,530 A | 9/1982 | Royer | |
| 4,356,259 A | 10/1982 | Banba | |
| 4,671,954 A | 6/1987 | Goldberg et al. | |
| 4,674,480 A | 6/1987 | Lemelson | |
| 4,680,174 A | 7/1987 | Jarvis, Jr. et al. | |
| 4,764,359 A | 8/1988 | Lemelson | |
| 4,925,661 A | 5/1990 | Huang | |
| 4,963,367 A | 10/1990 | Ecanow | |
| 5,017,379 A | 5/1991 | Lemelson | |
| 5,069,936 A | 12/1991 | Yen | |
| 5,129,877 A | 7/1992 | Gallo et al. | |
| 5,690,954 A | 11/1997 | Illum | |
| 6,117,454 A | 9/2000 | Kreuter et al. | |
| 6,498,147 B2 | 12/2002 | Nerenberg et al. | |
| 6,555,110 B1 | 4/2003 | D'Souza | |
| 7,105,158 B1 | 9/2006 | D'Souza et al. | |
| 2002/0081336 A1 | 6/2002 | Jonsson et al. | |
| 2002/0177568 A1 | 11/2002 | Stinchcomb et al. | |
| 2004/0005569 A1 | 1/2004 | Baker et al. | |
| 2004/0043079 A1 | 3/2004 | D'Souza | |
| 2005/0089576 A1 | 4/2005 | Moreau | |
| 2007/0078414 A1 | 4/2007 | McAllister et al. | |
| 2008/0166414 A1 | 7/2008 | Hanes et al. | |
| 2008/0269666 A1 | 10/2008 | Wang et al. | |
| 2008/0269685 A1* | 10/2008 | Singh .................. | A61K 9/0021 604/173 |
| 2009/0081306 A1 | 3/2009 | D'Souza | |
| 2009/0155330 A1 | 6/2009 | Ghartey-Tagoe et al. | |
| 2010/0111984 A1 | 5/2010 | D'Souza | |
| 2011/0121486 A1 | 5/2011 | Oh et al. | |
| 2015/0112250 A1 | 4/2015 | Kwon | |
| 2016/0287668 A1 | 10/2016 | Tankovich | |

FOREIGN PATENT DOCUMENTS

| | | | |
|---|---|---|---|
| JP | 2005513098 A | 5/2005 | |
| JP | 2006511461 A | 4/2006 | |
| WO | 9410980 A1 | 5/1994 | |
| WO | 9522963 A1 | 8/1995 | |
| WO | 0002574 A1 | 1/2000 | |
| WO | 2008053481 A1 | 5/2008 | |
| WO | 2009094394 A1 | 7/2009 | |

OTHER PUBLICATIONS

Ceseracciu et al., Robust and biodegradable elastomers based on corn starch and polydimethylsiloxane (PDMS), ACS Appl Mater Interfaces, Jan. 26, 2015, vol. 7, No. 6, pp. 3742-3753.

Nasatto et al., Methylcellulose, a cellulose derivative with original physical properties and extended applications, Polymers, Apr. 24, 2015, vol. 7, pp. 777-803.

Search Report for International Patent Application No. PCT/US2017/061353; dated Jan. 29, 2018.

Crcarevska et al., Chitosan coated Ca-alginate microparticles loaded with budesonide for delivery to the inflamed colonic mucosa, European Journal of Pharmaceutics 2008, 68:565-578, Available online Jun. 14, 2007.

Prego et al., Chitosan-PEG nanocapsules as new carriers for oral peptide delivery: Effect of chitosan pegylation degree, Journal of Controlled Release, 2006, 111:299-308.

Notification of Reasons for Refusal Translation, dated Dec. 24, 2013, JP Patent Application No. 2011-529378.

Supplementary European Search Report for European Patent Application No. EP 09 81 7062, filed Sep. 29, 2009, dated Mar. 20, 2013.

Haswani et al., Formulation, Characterization and Pharmacokinetic Evaluation of Gentamicin Sulphate Loaded Albumin Microspheres; Journal of Microencapsulation, Dec. 2006; vol. 23, No. 8; pp. 875-886.

Huang et al., The Characteristics of Betamethasone-Loaded Chitosan Microparticles by Spray-Drying Method, Journal of Microencapsulation, vol. 20, No. 4, Jul./Aug. 2003, pp. 459-472.

Search Report and Written Opinion from International Application No. PCT/US2016/55515; dated Jan. 24, 2017.

International Preliminary Report on Patentability for International Patent Application No. PCT/US2017/061353, dated May 14, 2019.

\* cited by examiner

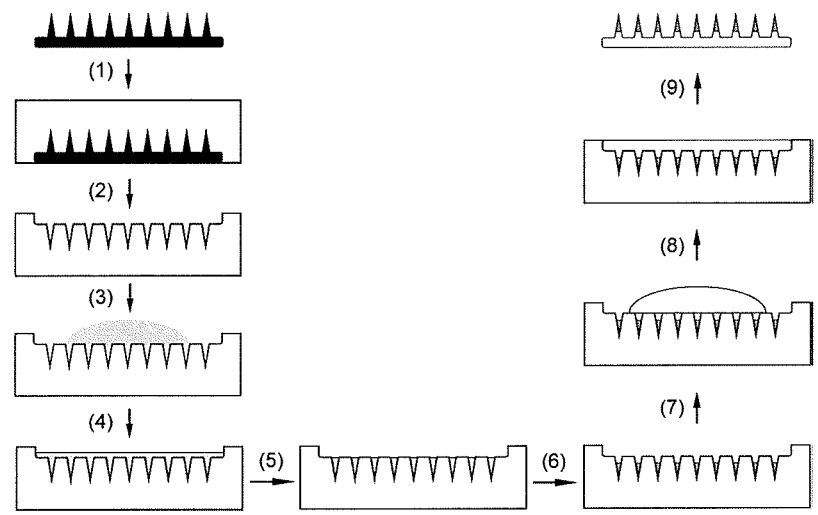
Figure 5
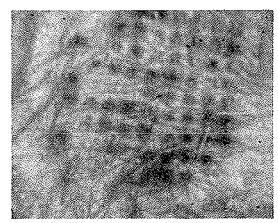 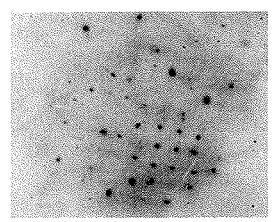
Figure 6A    Figure 6B
Figure 7

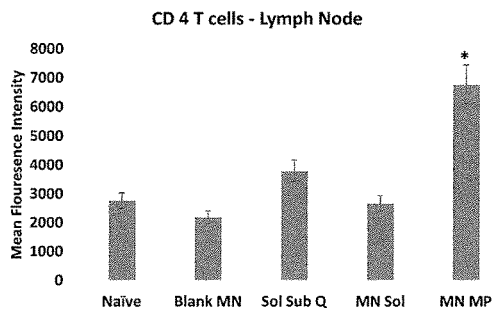 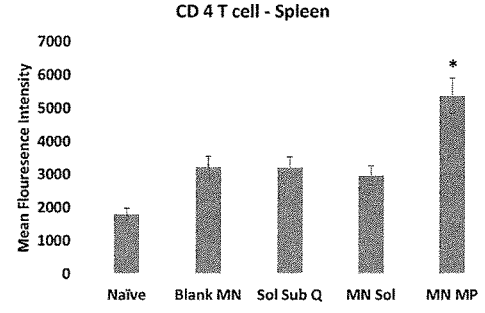
Figure 10A Figure 10B
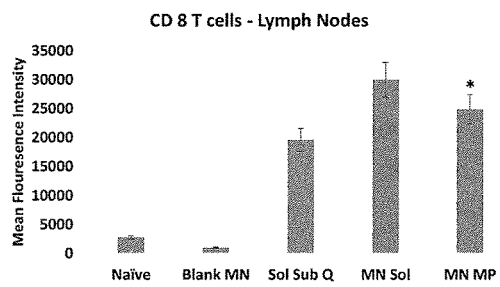 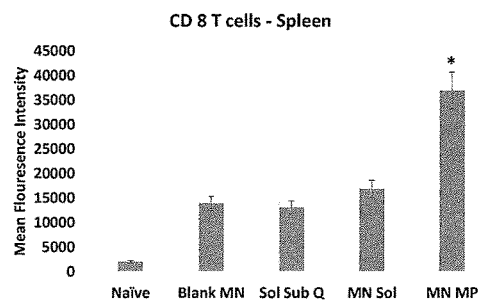
Figure 10C Figure 10D
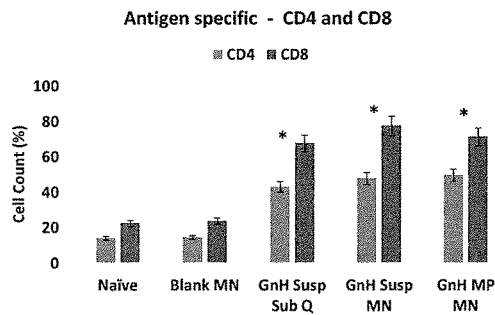
Figure 11

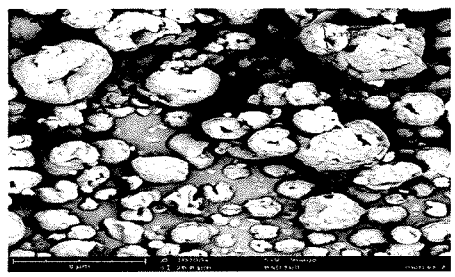 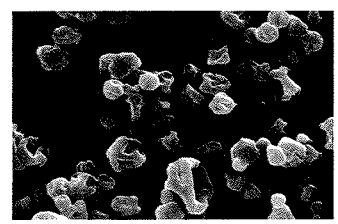
Figure 12A  Figure 12B
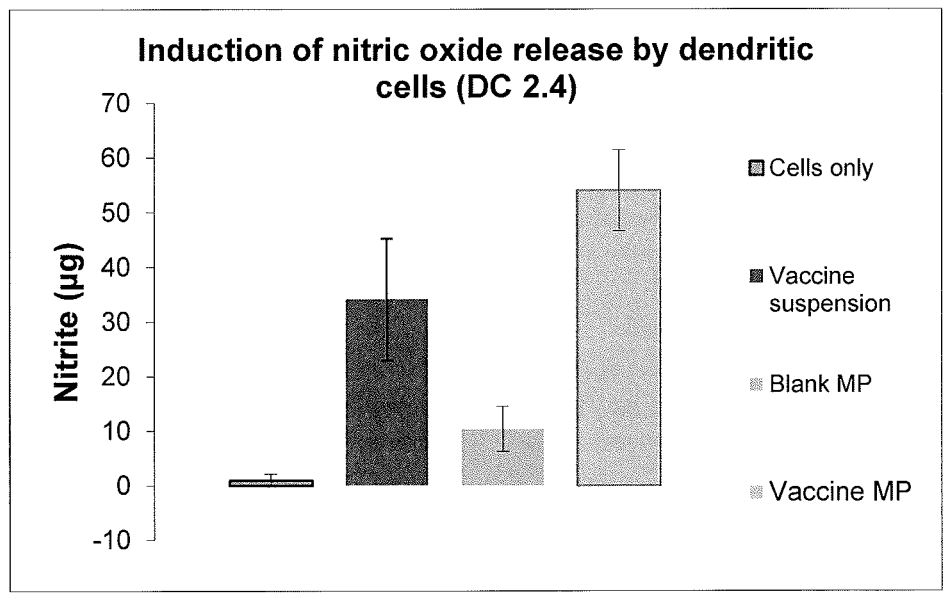
Figure 13

MICRONEEDLE-BASED TRANSDERMAL DELIVERY SYSTEM AND METHOD OF MAKING SAME

CROSS-REFERENCE TO RELATED APPLICATIONS

This application is a continuation-in-part of co-pending application Ser. No. 14/874,978, filed Oct. 5, 2015, entitled Nanospheres Encapsulating Bioactive Material and Method for Formulation of Nanospheres, which claims benefit of priority to U.S. patent application Ser. No. 12/569,867, filed Sep. 29, 2009, now U.S. Pat. No. 9,149,441, issued Oct. 6, 2015, and corresponding Provisional U.S. Patent Application No. 61/100,886, filed Sep. 29, 2008, and commonly assigned to the assignee of the present application, the disclosure of which is incorporated by reference in its entirety herein.

FIELD

The present disclosure relates, in exemplary embodiments, to a system for delivering bioactive and other materials through the skin (transdermally) using microneedles containing the material. The present disclosure also relates, in exemplary embodiments, to methods for forming biodegradable microneedles containing the bioactive material.

BACKGROUND

Currently, most vaccines are administered via subcutaneous or intramuscular route. These have been highly effective in generating protective immune response, but they remain invasive, potentially painful and require a skilled professional for vaccination. In an attempt to minimize some of these issues scientists have explored the potential of delivering vaccine antigens intradermally using microneedles. Microneedles, as the name indicates, are micron diameter-sized needles, which upon insertion into the skin result in formation of aqueous conduits forming a passage for the vaccine antigens towards the immune-competent skin layers. Due to their short needle length, they avoid contact with the nerve endings in the dermis thus remain to be a painless mode of immunization. Recently FDA approved Intanza™ (by Sanofi Pasteur), an intradermal influenza vaccine that incorporates a 1.5 mm needle attached to a pre-filled syringe loaded with flu antigens. It has been shown to be efficacious when compared with an IM flu vaccine thus bringing a switch from hypodermic needles to "micro"-needles for immunizations. This opens a new avenue of vaccine delivery through an effective, painless and patient-friendly route of administration. However, heretofore, there has not been a biodegradable and biocompatible microneedle transdermal delivery system.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

In exemplary embodiments, disclosed is a transdermal delivery system of microneedles containing a bioactive material, comprising at least one layer of a support material, at least one biodegradable needle associated with the support material, each needle comprising at least one biodegradable polymer and at least one sugar, wherein each biodegradable needle is hollow and is adapted to retain a bioactive material.

In exemplary embodiments, disclosed is a biodegradable microneedle, comprising: at least one biodegradable needle associated with the support material, each needle comprising at least one biodegradable polymer, and at least one sugar; wherein each biodegradable needle is at least partially hollow and is adapted to retain a bioactive material.

In exemplary embodiments, disclosed is a method of forming transdermal delivery system, comprising: (a) providing at least one biodegradable polymer material; (b) dissolving the polymer material in a solvent to form a solution; (c) mixing the solution of polymer material of step (b) with at least one sugar to form a polymer-sugar mixture; (d) providing a bioactive material; (e) providing a microneedle mold; (f) adding the bioactive material and the polymer-sugar mixture of step (c) to the microneedle mold; and, (g) forming at least one microneedle from the polymer-sugar mixture, the at least one microneedle having at least a portion that is hollow, wherein the bioactive material is retained within the hollow portion of the microneedle.

In exemplary embodiments, disclosed is a method of transdermally delivering a bioactive material, comprising: (a) forming at least one biodegradable and at least partially hollow microneedle from at least one biodegradable polymer and at least one sugar; (b) associating a bioactive material with the at least one microneedle; (c) associating the at least one microneedle with a backing layer; and, (d) contacting the at least one microneedle containing the bioactive material with the skin of a subject, whereby the at least one microneedle introduces the bioactive material to the subject and the at least one microneedle biodegrades.

In exemplary embodiments, disclosed is a method of forming transdermal delivery system, comprising: (a) mixing PVA, HPMC, and the at least one sugar in a vessel; (b) dissolving the mixture of step (a) in water to and mixing to form a mixture; (c) adding ammonium hydroxide to the mixture of step (b) and mixing; (d) adding to the mixture of step (c) at least one bioactive material in microencapsulated form to form a formulation; (e) adding an aliquot of the formulation of step (d) to a microneedle mold; and, (f) centrifuging the microneedle mold and formulation of step (e) to force the formulation into the microneedle mold.

BRIEF DESCRIPTION OF THE DRAWINGS

The drawings disclose exemplary embodiments in which like reference characters designate the same or similar parts throughout the figures of which.

Example 1 Figures.

Example 6 Figures.

DETAILED DESCRIPTION

Figure 1A:
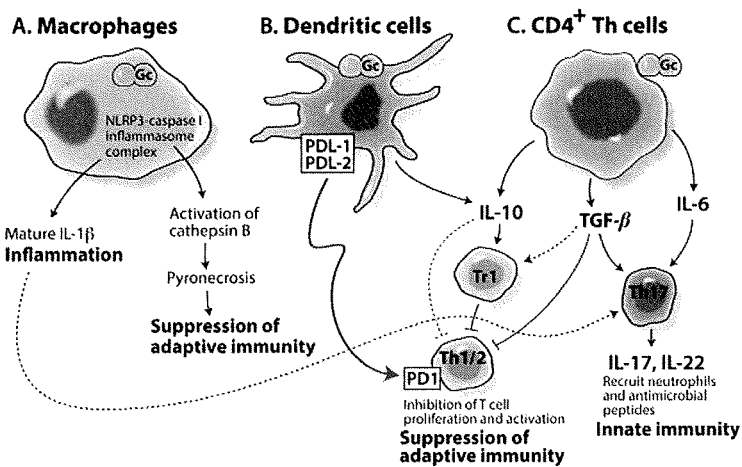
FIG. 1A is a diagram showing mechanisms of interaction of N. gonorrhoeae with cells of the immune system.

While transdermal delivery through skin is referred to herein, the presently disclosed microneedle systems and methods can be adapted for delivery to or through other structures, such as, but not limited to, blood vessel walls, muscle tissue, organs, and the like.

The following examples are set forth for purposes of illustration only. Parts and percentages appearing in such examples are by weight unless otherwise stipulated.

Example 1

Transdermal Microneedle Based Particulate Vaccines

1) Transdermal Microneedle Based Particulate *Neisseria gonorrheoeae* Vaccine

Background and Significance

*Neisseria gonorrhoeae* (the gonococcus, or GC) remains an important disease. Still relatively common in the US, with over 300,000 reported cases annually, and probably as many that are not reported, it is much more common in Africa and in many other parts of the less-developed world (Ison, Deal, & Unemo, 2013) [Example 1: Ref. 1]. Untreated gonococcal infection in women may progress to pelvic inflammatory disease, increasing the risk of ectopic pregnancy and infertility (Edwards, Jennings, Apicella, & Seib, 2016) [Example 1: Ref. 2]. The main reason to urge development of a gonococcal vaccine is emergence of antibiotic resistant GC. In many parts of the world, fluorinated quinolones are no longer recommended because of the prevalence of resistance (Jerse & Deal, 2013) [Example 1: Ref. 3]. The increasing threat of difficult-to-treat GC should make a gonococcal vaccine an important objective (Tapsall, 2009) [Example 1: Ref. 4].

The Gc interacts with the immune system and prevents the generation of an adaptive immune response. Gc can interact with various immune cells to elicit innate inflammatory responses and suppress Th1/Th2-mediated specific immune responses (FIG. 1). (A) Phagocytosis by macrophages results in activation of NLRP3 inflammasomes, the production of IL-1 and activation of PMNs, and activation of cathepsin B, which leads to pyronecrosis of APC (Duncan et al., 2009) [Example 1: Ref. 5]. (B) Interactions with DCs lead to up-regulation of PDL-1 and PDL-2, which induce apoptosis of cells bearing PD1. This up-regulation also causes release of IL-10, which has immunoregulatory properties and stimulates type 1 regulatory T cells (Tr1) (Zhu et al., 2012) [Example 1: Ref. 6]. (C) Interaction with CD4+ T helper cells (or B cells) induces secretion of IL-10, TGF-β, and IL-6 (Liu, Islam, Jarvis, Gray-Owen, & Russell, 2012)

[Example 1: Ref. 7]. IL-10 and TGF-β suppress the activation of Th1 and Th2 cells both directly, and through the activation of Tr1 cells. TGF-β and IL-6 drive the development of Th17 cells which secrete IL-17 and IL-22, leading to the recruitment or induction of innate defenses such as PMNs and anti-microbial peptides. Gc is able to resist destruction by PMNs and anti-microbial peptides while concomitantly suppressing the development of adaptive immune responses such as Gc-specific antibodies that could enhance phagocytosis and intracellular killing by phagocytes and bacteriolysis through the classical complement pathway (Jerse, Bash, & Russell, 2014 [Example 1: Ref. 8]). Thus exploring a transdermal microparticle vaccine formulation that confers protection in patients, induces herd immunity, and provides significant advantages over the conventional antibiotic therapy will have high public health impact in the United States.

Specific Aims:

Specific Aim 1: Optimize/Characterize a Novel Whole-Cell Inactivated *Neisseria Gonorrheae* Nanovaccine Formulation Delivered Using Biodegradable Microneedle Skin Patch:

1. Determine the optimal dose of antigen encapsulation into nanoparticles for further loading into biodegradable microneedles 2. Characterize the novel gonococcal nanoparticles formulation long-term stability, antigens release and antigens uptake by antigen presenting cells (macrophages and dendritic cells) in vitro.

3. Effective antigen presentation by APCs or dendritic cells pulsed with gonococcal nanoparticles (measure co-stimulatory molecules induction, DCs maturation markers and T cell proliferation 4. Monitor in vivo subcutaneous antigen release from gonococcal nanoparticles loaded into microneedles skin patch in mice using fluorescent probe bound to nanoparticles and imaging method. Monitor duration and scale of antigen release as nanoparticles diffusion into subcutaneous skin.

Specific Aim 2: Determine the Correlates of Protection in Immunized Mice:

1. Compare gonococcal nanoparticles-loaded into microneedles skin patch to gonococcal nanoparticles vaccine injected intraperitoneally in mice.

2. Measure the induction of antibody titers, total IgG and subclasses elicited against gonococcal antigens in vaccinated mice sera, and antigen-specific CD4/CD8 T cell in spleens and lymph nodes of vaccinated mice.

3. Determine the serum opsonic and bactericidal activity of elicited antibodies against live *Neisseria gonorrheae* using the parent strain F62 as well as other clinical gonococcal isolates (cross protection).

Innovation

A. Microparticulate Vaccines

We have developed a biodegradable and biocompatible polymer matrix system for making the microparticles loaded with the vaccine using the spray drier method (Chablani et al., 2012; Shastri, Kim, Quan, D'Souza, & Kang, 2012; Ubale, D'Souza, Infield, McCarty, & Zughaier, 2013; Ubale, Gala, Zughaier, & D'Souza, 2014a) [Example 1: Refs. 9-12]. This method does not require organic solvents which enhances the safety of such formulation. We formulated a microparticle gonococcal vaccine that serves as a sustained release system. The proposed vaccine formulation consists of formalin fixed dead whole cell gonococcal encapsulated in albumin-based microparticles that mimic the chemical conjugation process of CPS to a protein carrier similar to meningitis, and enhance antigen uptake via albumin receptors, and elicit a T-cell-dependent immune response. Further, the proposed vaccine exists as a dry powder form and kept well protected from moisture. Thus, the shelf lives of these vaccines are expected to be several fold higher than that of the conventional vaccines. The novel nanotechnology-based vaccine that mimics conjugation effects by encapsulation into albumin-based nanoparticle matrices provides the following advantages: 1—does not require chemical conjugation, 2—self adjuvanting-antigen delivery vehicle, 3—enhanced uptake by immune cells and slow antigen release, i.e. antigen depot effect, 4—induces robust autophagy formation that enhances antigen presentation, 5—uses a heat-stable formulation that does not require refrigeration, 6—can be administered via microneedles 7—the cost of producing this vaccine is dramatically reduced due to the elimination of the costs of chemical conjugation process, purification and packaging in individual dose ampoules that requires constant cooling with limited shelf life, and 8—can be used to formulate and deliver other bacterial and viral vaccines.

B. Whole Cell Vaccine Antigen

Figure 1B:
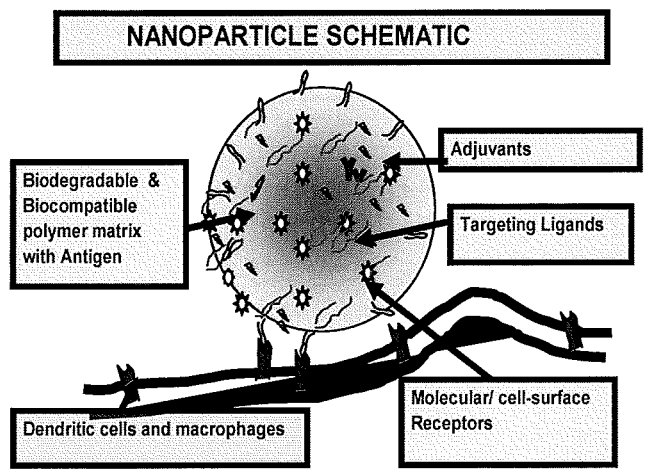
FIG. 1B is a schematic diagram of a microparticulate delivery system.

*Neisseria gonorrhoeae* is the main bacteria which causes gonorrhea infections. There have been various approaches which have been investigated for a vaccine strategy against gonorrhea infections. Since the immune suppression caused by the bacteria via various mechanisms explained in FIG. 1 there was no adaptive immune response generated. Moreover there has not been much research on development of gonorrhea vaccine which is evident from a PubMed search on Dec. 27, 2010 under "gonococcal vaccine" yielded 247 entries, whereas a similar search under "meningococcal vaccine" yielded 3326 entries. With the development of antibiotic resistant strains of gonorrhea, FDA and CDC have prioritized the research on development of a vaccine against gonorrhea. We have developed a novel approach where the whole cell of *N. gonorrheoeae* is formalin fixed for overnight and used as the vaccine antigen. By using the whole cell as the antigen, we preserve and present all the possible antigenic proteins in their native form to the antigen presenting cells. This approach will cover all the antigenic sites and help in inducing an immune response. Moreover when encapsulated in a microparticulate form, it will be better up taken by the APCs and processed.

Figure 2:
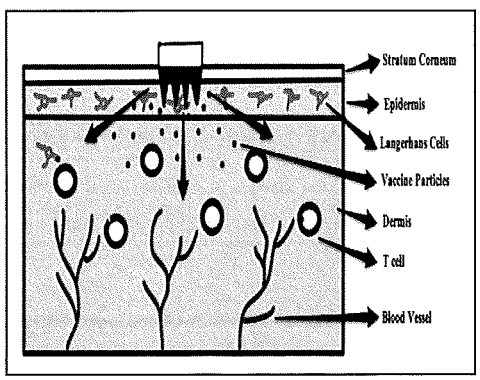
FIG. 2 is schematic view of a microneedle device according to one exemplary embodiment used for transdermal delivery of particles.

Microneedle Based Transdermal Vaccination:

The skin provides a unique site for the vaccination purposes as it is easily accessible and houses various immune cells for an efficient immune response against a range of antigens. Skin serves as a barrier against various pathogens and is equipped with the skin associated lymphoid tissues (SALT) to combat any insult from invading pathogens. Various skin cells assist in generation of effective immune response (Gao, Pan, Chen, Xue, & Li, 2008) [Example 1: Ref. 13]. Keratinocytes are the most predominant (95%) epidermal cells in the skin. They can be activated by pathogens and result in production of cytokines, which in turn recruits dendritic cells/antigen-presenting cells to the site of action leading to initiation of the immune response. Skin host's a special kind of dendritic cells, namely, the Langerhans cells. Langerhans cells comprise of only 2% of the total cell population in the epidermis but due to their extended dendrites spread in the epidermal layer they cover over 25% of the skin surface. These are professional phagocytic cells efficient in immune surveillance and further signaling to the T-cells present in their vicinity. Activated macrophages and T-cells drain into nearby lymph nodes leading to an enhanced immune response. Currently, most of the vaccines are administered via subcutaneous or intramuscular route. These have been highly effective in generating protective immune response but they remain to be invasive, painful and require a skilled professional for vaccination. In an attempt to minimize some of these issues scientists have explored the potential of delivering vaccine antigens intradermally using microneedles. Microneedles, as the name indicates, are micron-sized diameter needles, which upon insertion into the skin result in formation of aqueous conduits forming a passage for the vaccine antigens towards the immune-competent skin layers (FIG. 2). Due to their short needle length, they avoid contact with the nerve endings in the dermis thus remain to be a painless mode of immunization. Recently FDA approved Intanza™ (by Sanofi Pasteur), an intradermal influenza vaccine that incorporates a 1.5 mm needle attached to a pre-filled syringe loaded with flu antigens. It has been shown to be efficacious when compared with an IM flu vaccine thus bringing a switch from hypodermic needles to "micro"-needles for immunizations. This opens a new avenue of vaccine delivery through an effective, painless and patient-friendly route of administration. The success of immunization via skin using microneedles inspired us to evaluate the potential of delivering gonorrhea vaccine through this route.

To summarize, multiple approaches were applied to ensure development of potent and efficacious vaccine against gonorrhea. Following innovative approaches will be combined:

1. Currently there is no approved FDA vaccine against gonorrhea infection.

Development of an efficacious vaccine will have a major impact in combating the infection caused by drug resistant strains of N. Gonorrhea.

2. The entire cell surface of the N. Gonorrhea bacteria is preserved which helps to present all the antigenic sites on the bacterial surface to the immune system.

3. Particulate nature of vaccine ensures sustained release of antigens, higher internalization and stronger immune response than vaccine solution 4. Transdermal immunization via biodegradable microneedles that rapidly dissolve or biodegrade in contact with water is a unique route of administration and thus exposing the antigens to the Langerhans cells, dermal dendritic cells.

5. The transdermal route offers a painless, self-administration and patient compliant immunization strategy 6. We recently demonstrated the potential for a gonorrhea vaccine in a murine model (see preliminary data section).

Paradigm Shift:

Infections caused by *Neisseria gonorrhoeae* (the gonococcus) continue to be a global, intractable problem. The absence of a gonococcal vaccine, together with the continuing emergence of antibiotic-resistant and untreatable gonococcal strains, has raised awareness that *N. gonorrhoeae* poses an "urgent" public health threat for which immediate aggressive action is greatly needed (Unemo & Shafer, 2014). Our approach of using microparticulate based delivery system is believed to interact with the immune system differently and has shown positive results in various studies. The particulate nature of the vaccine allow the vaccine antigen to be taken by the dendritic cells and macrophages and thus enhance its presentation and subsequent activation of T cells. Thus by using the whole cell of gonorrhea in a microparticulate delivery system, and also harnessing the rich immune system of the skin, we believe to have a potential immunization strategy against the infections caused by N. Gonorrhea. We have got encouraging results for using this strategy (see preliminary results) and believe this to be a potential vaccine against gonorrhea.

Approach
Preliminary Results

Figure 3A:
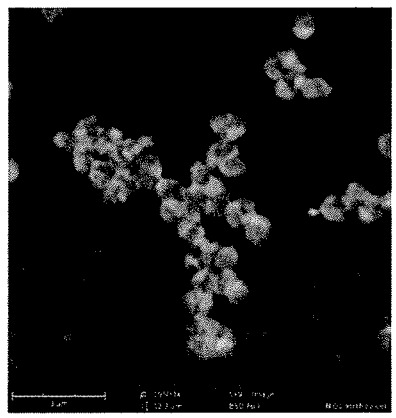
FIG. 3A is a scanning electron microscopic (SEM) image of formalin fixed whole cell N. gonorrheoeae which is the antigen for the vaccine.
Figure 3B:
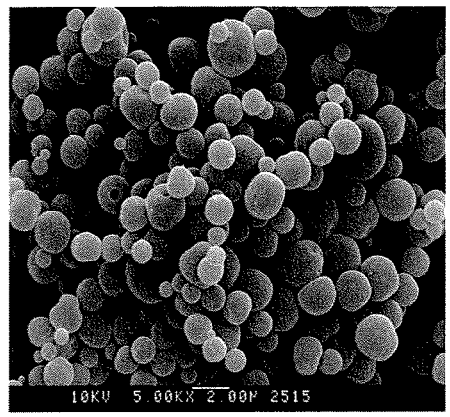
FIG. 3B is a SEM image of spray dried microparticles containing the gonorrhea vaccine antigen.
Figure 3C:
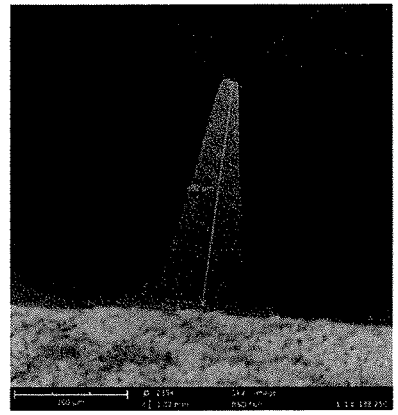
FIG. 3C is a SEM image of the dissolving microneedles which contain the gonorrhea vaccine microparticles for transdermal delivery.
Figure 4:
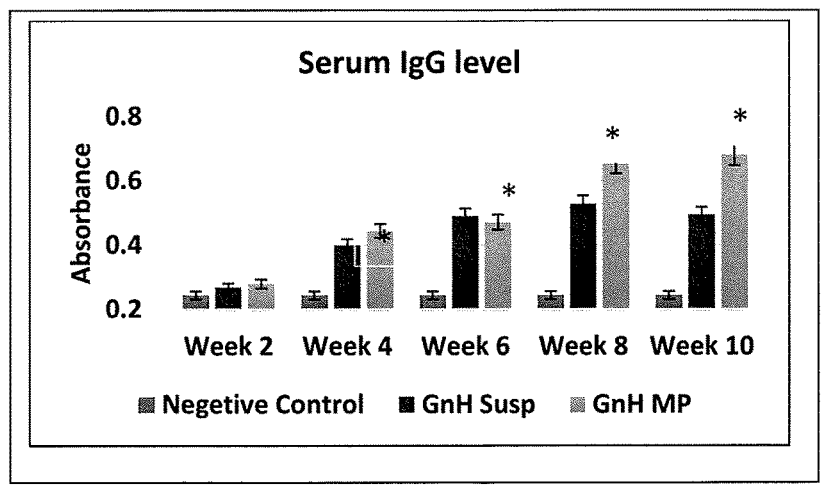
FIG. 4 is a graph of N.
Figure 8:
Figure 9:
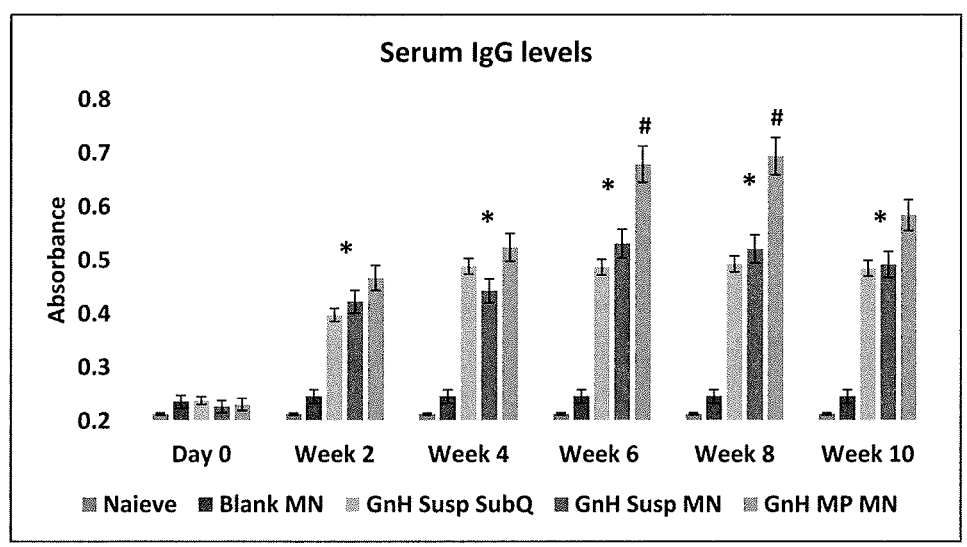
Figure 14A:
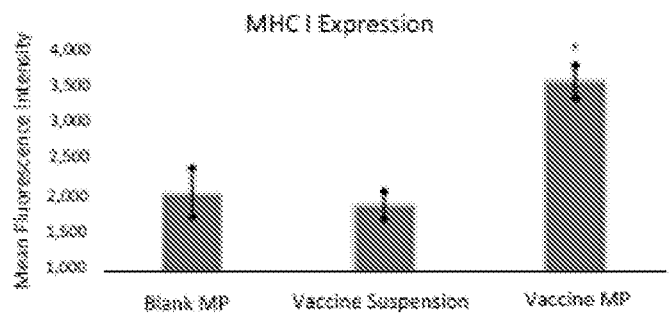
Figure 14B:
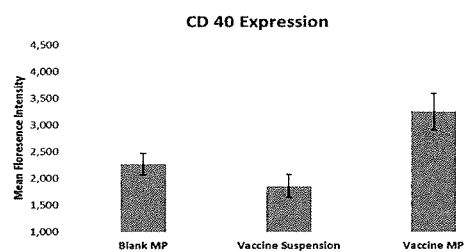
Figure 14C:
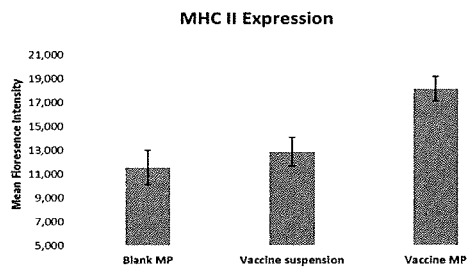
Figure 14D:
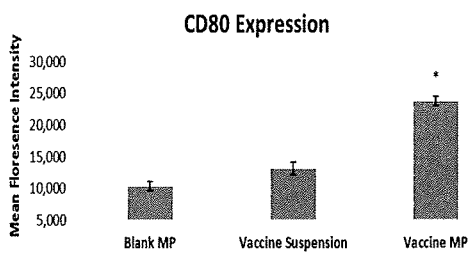

Formulation of whole cell gonorrhea microparticulate vaccine: The *N. gonorrheoeae* cells were grown in culture medium. When confluent, the media was removed and a 10% solution of formalin was added and kept overnight. This will lead to fixation of the cells in their native form which were used as the antigen for the vaccine (FIGS. 3A-B). FIGS. 3A-B shows that the cells were intact and were in their native form. This antigen was mixed with a blend of biodegradable and biocompatible cellulose polymer matrix. This was then spray dried and microparticles were made. These microparticles were characterized for their size, charge etc.

Microparticulate Morphology and Characterization

Scanning electron microscopy (SEM) was performed to evaluate the microparticle size and surface morphology. Microparticles were mounted onto metal stubs using double sided adhesive tape. After being coated with a thin layer (100-150° A), the microparticles were examined using a Phenom scanning electron microscope (FIGS. 3A-B). Recovery yield of the microparticles after spray drying was calculated for all the formulated batches. Percent recovery yield was evaluated using the following formula:

$$\text{Percentage Recovery Yield} = \frac{\text{Weight of microparticles after spray drying} * 100}{\text{Weight of all ingredients before spray drying}}$$

Particle size of the optimized formulation was evaluated using the Spectrex Laser Particle counter that works on the principle of laser diffraction. Particle size was measured in triplicates for blank as well as vaccine microparticles. For zeta potential measurement, five micrograms of microparticles were suspended in 1 ml of deionized water and measured using a Malvern Zetasizer. Zeta Potential was measured for blank as well as antigen loaded microparticles in triplicates. The particle size, recovery yield and zeta potential are all shown in Table 1.

TABLE 1

| Average Size | 3.5 µm ± 1.2 µm |
|---|---|
| Zeta Potential | 7.1 mV ± 1.4 mV |
| Percentage Yield | 85% |

Microparticles may be formed according to the method disclosed in U.S. Pat. No. 9,149,441 entitled NANOSPHERES ENCAPSULATING BIOACTIVE MATERIAL AND METHOD FOR FORMULATION OF NANOSPHERES, the disclosure of which is incorporated herein in its entirety.

In one exemplary embodiment, microparticles can be prepared by spray-drying an aqueous suspension containing a bioactive material (e.g., whole cell lysate (WCL)), ethyl cellulose, cellulose acetate phthalate (CPD), hydroxyl-propyl methylcellulose acetate succinate (HPMCAS) and trehalose using the following formula: Whole cell lysate WCL=10% w/w, Ethyl cellulose=35% w/w, Cellulose acetate phthalate (CPD)=25% w/w, Hydroxyl-propyl methylcellulose acetate succinate (HPMCAS)=25%, and Trehalose=5% w/w. This final mixture was then spray dried using Buchi 290 Mini Spray Dryer (Buchi Corporation, Newcastle, Del.) with an inlet temperature of 125° C. and outlet temperature of 80° C. The particles were stored at −20° C. until further use. In exemplary embodiments, microparticles including an adjuvant (that can enhance the immunogenicity of a vaccine) can be prepared following the same procedure. In exemplary embodiments, particles may be made with adjuvant loading of 2.5% w/w.

In exemplary embodiments, the average particle size may be in a range of about 0.01-50 μm.

In exemplary embodiments, any of a variety of different sugars can be uses, including, but not limited to, trehalose, maltose, sucrose, or the like.

Method

Dissolving microneedles, intended for the painless transdermal release of encapsulated pharmaceutical agents after dermal insertion, were developed as a solution to the safety issue. Dissolvable microneedles mainly deploy PDMS micromolds which are made from a master structure of microneedles (FIG. 5). Briefly, Polydimethylsiloxane (PDMS) (Dow Chemicals) was poured onto the stainless steel master structure (Step 1-3; FIG. 5). The microneedles were made using the following formula:

Drug/Particles=10% w/w (5 mg), Trehalose=25% w/w (12.5 mg), Maltose=25% w/w (12.5 mg), PVA=20% w/w (10 mg), HPMC=20% w/w (10 mg)

The calculated quantities in bracket are for 50 mg which is used for making 2 microneedle patch). PVA, hydroxypropyl methyl cellulose (HPMC), Maltose and Trehalose were added to a 1.7 mL microcentrifuge tube. The contents were dissolved in minimum possible amount of water (e.g., 200 mg of total solid content can be dissolved in 600 uL water). Vortex the centrifuge tube. Then approximately ⅕th quantity (of water that was added to dissolve the solids) of Ammonium hydroxide (NH4OH) was added to the microcentrifuge tube (here, 120 uL) and vortex again. The tube is kept aside for some time and observed if the contents are dissolved. If everything goes into the solution, add the weighed amount of gonorrhea vaccine microparticles in the end. This formulation is then added to mold avoiding air bubbles. These molds are then placed straight in 50 mL centrifuge tubes. Centrifugation is done in the fixed angle centrifuge in order to remove air bubbles and to force the formulation to go into the microneedles mold. The maximum speed is 2000 rpm which is achieved step wise, in order to avoid jerk in the rotation process, time for which centrifugation should be done is 5-10 min. Speed should be lowered gradually for same reason as above. After this centrifugation step, more formulation is added to molds and centrifugation is repeated in the same manner (Step 3-6; FIG. 5). This step can be repeated further by adding more formulation or a blank backing layer solution. In exemplary embodiments, the backing layer may be composed of the same components as the microneedle matrix as described in various embodiments herein, however, the backing layer is formed without any microparticles. Keep the molds in tubes and place it in an incubator at 37° C. overnight (Step 7-9; FIG. 5). The microneedle patch is 1 cm×1 cm in size which contains 100 microneedles (10×10). The microneedles are 600 μm.

In-Vivo and In-Vitro Characterization of the Microneedles.

Scanning electron microscopy (SEM) was performed to evaluate the microparticle size and surface morphology (FIG. 3C). The in-vitro delivery of the microneedles was checked on a porcine ear skin sample (FIGS. 6A-B). In-order to track the vaccine and microparticles from the microneedles, we prepared ICG loaded (IR dye) microneedles and administered to the mice on the back and monitored the intensity of the IR dye at regular intervals (FIG. 7). We could see that the intensity of the dye after 30 mins of application was localized and around the site of administration. As we monitored further, it spread to different organs in the mice at 6, 12 and 24 hours as shown in FIG. 7. In a different experiment to check the dissolution and delivery of microneedles when applied to the skin, we dosed a microneedle patch to a mice and hold it with an adhesive backing layer for 10-15 minutes. Then the microneedles patch was removed and SEM was taken to check if the microneedles and dissolved. From FIG. 8, we can see that after 12 minutes of application of the microneedles patch, all the needles had dissolved and only the back layer was left. This experiment confirmed the 100 delivery of the vaccine antigen to the skin.

Proof-of-Concept In-Vivo Immunization Study:

To check the efficacy of the whole cell microparticulate vaccine, it was administered to 4-6 weeks old mice (Balb-C) via subcutaneous route which serve as conventional routes of administration of vaccines. There were 3 groups, subcutaneous microparticle vaccine (GnH MP), subcutaneous vaccine suspension (GnH Susp) and negative control which was received the blank microparticles (n=6). There was one prime dose followed by two booster doses 2 weeks apart. Blood samples were collected prior to prime dose followed every 2 weeks. The antibody levels in the blood were measured using specific ELISA by plating the antigen on the plate. The antigen specific antibody in the serum was detected using ELISA. A rise in specific antibody levels is seen in FIG. 4 in groups which received the vaccine when compared to the blank microparticles which serve as the negative control after week 4.

Transdermal In-Vivo Immunization Study Using Microneedles

Since the subcutaneous route generated antibodies (Preliminary data; FIG. 8), we harness the rich immune system of the skin and deliver the vaccine via advanced microneedle patch. These microneedles are loaded with gonorrhea microparticulate vaccine which when applied to the skin, deliver the vaccine in the epidermis and dermis layers which is rich in dendritic cells and specialized Langerhans cells which will generate the immune response. The study will be carried out in 4-6 weeks Balb-c mice. There will be following groups in the study:

1. Naïve
2. Blank Microneedles
3. Vaccine Suspension (Subcutaneous)
4. Vaccine loaded Microneedles (Transdermal)
5. Vaccine Microparticles in Microneedles (Transdermal)

Similar to previous preliminary study, there was one prime dose and two booster doses. Blood samples will be collected prior to dosing and followed by every 2 weeks. The animals will be monitored for 10-12 weeks. The antibody are measured as previous described using ELISA (FIG. 9) which show that the groups receiving vaccine showed significantly higher serum IgG titers when compared to the controls—blank microparticles and blank microneedles after week 2. The group which received the GnH vaccine microparticles in microneedles showed significantly higher antibody titers than the other 2 vaccine groups at week 6 and 8 (n=6) (*$p<0.001$; #$p<0.05$). Thus we could say the potential of transdermal route via microneedle patch as an efficient and effective delivery system for vaccines.

Cellular Responses in the Immunized Mice:

After the animals were sacrificed, the primary and secondary lymphoid organs were extracted (i.e. spleen and lymph node) and made into single cell suspensions. The single cell suspensions were stained with fluorescence-conjugated antibodies specific to T cells, helper T cells (CD4+) and cytotoxic T cells (CD8+) and quantified using flow cytometry (FIG. 10). FIGS. 10A-D show the CD4 cell counts of lymph nodes (FIG. 10A) and spleens (FIG. 10B) and the CD8 cell counts in lymph nodes (FIG. 10C) and spleens (FIG. 10D). The groups which received the Gonorrhea vaccine microparticles incorporate in the microneedles showed significantly higher levels of both CD4 and CD8 T cells in immune organs when compared to groups receiving no vaccine and blank microneedles (*P<0.05). For determination of antigen specific T cell responses, splenocytes from the various groups were plated onto a 48 well plate and re-stimulated with antigen for 16 hours and then stained with fluorescently tagged antibodies for CD4 and CD8 cells and quantified using flow cytometry (FIG. 11). The groups receiving the vaccine via the subcutaneous or transdermal route showed significantly higher cell counts than the groups which did not receive the vaccine (*P<0.05).

EXAMPLE 1 REFERENCES

1. Ison C A, Deal C, Unemo M. Current and future treatment options for gonorrhea. Sex Transm Infect. 2013 December; 89 Suppl 4:iv52-56.
2. Edwards J L, Jennings M P, Apicella M A, Seib K L. Is gonococcal disease preventable? The importance of understanding immunity and pathogenesis in vaccine development. Crit Rev Microbiol. 2016 Jan. 23; 1-14.
3. Jerse A E, Deal C D. Vaccine research for gonococcal infections: where are we? Sex Transm Infect. 2013 December; 89 Suppl 4:iv63-68.
4. Tapsall J W. *Neisseria gonorrhoeae* and emerging resistance to extended spectrum cephalosporins. Curr Opin Infect Dis. 2009 February; 22(1):87-91.
5. Duncan J A, Gao X, Huang M T-H, O'Connor B P, Thomas C E, Willingham S B, et al. *Neisseria gonorrhoeae* Activates the Proteinase Cathepsin B to Mediate the Signaling Activities of the NLRP3 and ASC-Containing Inflammasome. J Immunol. 2009 May 15; 182(10): 6460-9.
6. Zhu W, Ventevogel M S, Knilans K J, Anderson J E, Oldach L M, McKinnon K P, et al. *Neisseria gonorrhoeae* Suppresses Dendritic Cell-Induced, Antigen-Dependent CD4 T Cell Proliferation. PLOS ONE. 2012 Jul. 23; 7(7):e41260.
7. Liu Y, Islam E A, Jarvis G A, Gray-Owen S D, Russell M W. *Neisseria gonorrhoeae* selectively suppresses the development of Th1 and Th2 cells, and enhances Th17 cell responses, through TGF-β-dependent mechanisms. Mucosal Immunol. 2012 May; 5(3):320-31.
8. Jerse A E, Bash M C, Russell M W. Vaccines against gonorrhea: current status and future challenges. Vaccine. 2014 Mar. 20; 32(14):1579-87.
9. Chablani L, Tawde S A, Akalkotkar A, D'Souza C, Selvaraj P, D'Souza M J. Formulation and evaluation of a particulate oral breast cancer vaccine. J Pharm Sci. 2012 October; 101(10):3661-71.
10. Shastri P N, Kim M-C, Quan F-S, D'Souza M J, Kang S-M. Immunogenicity and protection of oral influenza vaccines formulated into microparticles. J Pharm Sci. 2012 October; 101(10):3623-35.
11. Ubale R V, D'Souza M J, Infield D T, McCarty N A, Zughaier S M. Formulation of meningococcal capsular polysaccharide vaccine-loaded microparticles with robust innate immune recognition. J Microencapsul. 2013; 30(1):28-41.
12. Ubale R V, Gala R P, Zughaier S M, D'Souza M J. Induction of death receptor CD95 and co-stimulatory molecules CD80 and CD86 by meningococcal capsular polysaccharide-loaded vaccine nanoparticles. AAPS J. 2014 September; 16(5):986-93.
13. Gao H, Pan J-C, Chen B, Xue Z-F, Li H-D. [The effect of HPV16E7 DNA vaccine transdermal delivery with microneedle array]. Zhonghua Yu Fang Yi Xue Za Zhi. 2008 September; 42(9):663-6.

Example 2

Preclinical Evaluation of a Novel Microneedle Based Transdermal Microparticulate Vaccine for Metastatic Breast Cancer Abstract According to the National Cancer Institute, breast cancer affects one in eight women during their lives. It kills more women in USA than any other cancer. Current treatment strategies act non-specifically against both tumor cells and normal cells. We have previously tested the efficacy of vaccine microparticles in a prophylactic setup and found that vaccination induces an immune response against cancer antigens and helps controls tumor growth. After carrying out preliminary studies involving both in-vitro and in-vivo evaluation of vaccine microparticles, we wanted to further investigate the therapeutic benefits of vaccine microparticles against breast cancer in murine breast cancer model. The immunized animals showed significantly lower tumor growth compared to the naïve animals that did not receive any treatment. The delay in tumor growth in vaccinated animals was due to a strong immune response generated against the tumor-associated antigens encapsulated within the microparticles. We observed a significant increase in the CD4+ T cell population. Our research strategy is to combine chemotherapy with immunotherapy. Low dose chemotherapy has been reported to inhibit the immunosuppressive regulatory T cells. The immune organs will be collected and processed to understand the immune response generated after simultaneous administration of vaccine microparticles and chemotherapeutic drug. Primary breast cancer is currently treated with surgical removal, chemotherapy and/or radiotherapy. But due to metastatic tumor spread many (20-25%) patients experience a relapse of the tumors despite these interventions. Using murine 4T1 metastatic breast cancer cell line we have developed a microparticulate vaccine formulation. These particles were evaluated for their size, charge, surface morphology by various in vitro studies. This proposal will explore the feasibility of eliminating residual breast cancer cells/tumors and avoiding disease recurrence using a primary vaccine treatment approach in a murine model of breast cancer.

Significance

Breast cancer (BC) is the most commonly diagnosed malignancy and is the second leading cause of cancer related death in American women. This year over 250,000 women will be diagnosed with breast cancer and almost 50,000 women will die from metastatic breast cancer. Currently there are no FDA approved vaccines for breast cancer. For this reason development of a therapeutic breast cancer vaccine is an area of research that needs urgent attention offering these women a better chance of a cancer free life. Many therapeutic vaccine strategies are under clinical trials for breast and other types of cancers (1). Most vaccines being studied today, such as the gene transfer based vaccines require live cultured cells, which is time consuming and difficult to establish in many cancers. It is well known that breast cancer cells do not grow easily in vitro, significantly limiting the number of patients eligible for such clinical trials and ultimately vaccine therapy. A recent clinical trial evaluating vaccine-based therapy concluded that one of the major problems with gene-based cancer vaccine therapy is the delay vaccine production which significantly limits the access of patients to the trial and subsequent therapy (2). Another potential problem is that the delay in vaccine production and subsequent administration could also result in a delay in treatment and progression of tumor metastasis resulting in increasing tumor burden and worsening prognosis. Therefore an optimum cancer vaccine requires a rapid production time, ease of delivery, and has the ability to be customizable for individual patients. Our proposed microparticle-based vaccine approach, addresses many of the problems associated with the current vaccine therapies including the high vaccine costs. We have developed a novel formulation using sustained release polymers encapsulating antigens in a biodegradable matrix containing immune potentiator adjuvants (3-7). This has been confirmed in several other studies in our laboratory with ovarian (4), prostate (8) and melanoma (7) vaccines. Thus, we expect our proposed breast cancer vaccine formulations to be very robust for inducing immunity and to overcome most of the problems associated with soluble antigens.

We use a multi-fold approach to enhance the immunogenicity and efficacy of cancer vaccine microparticles. Following are the approaches:

Particle-based vaccination for BC: There are several challenges in developing an effective vaccine, which include the maintenance of vaccine integrity and stability, avoidance of immune tolerance, and induction of strong protective immunity. We have been studying the encapsulation of drugs in our lab as well for the past 22 years and have shown that microparticles containing different drugs in the 0.5-2 µm size are readily taken up by phagocytic macrophages (21). Recently, we have made major advances in the formulation process, and have several patents demonstrating the production of microparticles using a modified spray drying methodology in a single step process (see, for example, U.S. Pat. Nos. 6,555,110, 7,105,158, and 7,425,543, the disclosures of which are incorporated by reference herein in their entirety). The microparticles provide a depot from which the antigens a slowly release and cause a long lasting immune response. These microparticles protect the antigen from being cleared out from the body thus, enhancing the vaccine stability. This will be a major advantage from the standpoint of advancing the vaccine formulation from bench to clinic as scale-up of the process can easily be achieved with no further modifications.

Adjuvant for immune-potentiation in BC: In the recent years, adjuvants like MF59 have been incorporated in vaccine formulation to enhance the specific immune response generated by the antigen. MF59 can potentiate the immune response by either increasing the antibody response and inducing cell mediated immunity i.e. they have a balanced strong Th1/Th2 stimulation. The use of adjuvants not only enhances immunogenicity but could also permits the reduction in the antigen dose to be delivered in vaccine thus sparing the antigen. MF59 is a squalene in water emulsion which is commercially been approved in Europe with more than 27 million doses of vaccine containing MF59 have been administered. Novartis Vaccines has developed an influenza vaccine using MF59 along with inactivated, subunit seasonal prophylactic vaccine that is commercialized successfully as Fluad® in Europe. The safety and efficacy of MF59 has been established clinically with a large database.

Temporary depletion of Treg cells: Using a low dose of cyclophosphamide the Treg can be suppressed before vaccination. The dose of cyclophosphamide is much lower than the chemotherapeutic dose, thus there are no potential side effects to the patients. The Treg cells remain depleted for a short period of 45 days and then again reach normal levels. Thus during the vaccination regimen the Treg levels are low and aid in generation of a strong immune response Transdermal Vaccination:

The skin provides a unique site for the vaccination purposes as it is easily accessible and houses various immune cells for an efficient immune response against a range of antigens. Skin serves as a barrier against various pathogens and is equipped with the skin associated lymphoid tissues (SALT) to combat any insult from invading pathogens. Various skin cells assist in generation of effective immune response. Keratinocytes are the most pre-dominant (95%) epidermal cells in the skin. They can be activated by pathogens and result in production of cytokines, which in turn recruits dendritic cells/antigen-presenting cells to the site of action leading to initiation of the immune response. Skin host's special kind of dendritic cells, the Langerhans cells. Langerhans cells comprise of only 2% of the total cell population in the epidermis but due to their extended dendrites spread in the epidermal layer they cover over 25% of the skin surface. These are professional phagocytic cells efficient in immune surveillance and further signaling to the T-cells present in their vicinity. Activated macrophages and T-cells drain into nearby lymph nodes leading to an enhanced immune response. Currently most of the vaccines are administered via subcutaneous or intramuscular route. These have been highly effective in generating protective immune response but they remain to be invasive, painful and require a skilled professional for vaccination. In an attempt to minimize some of these issues scientists have explored the potential of delivering particulate based vaccine antigens intradermally using microneedles formulated in our laboratory as described earlier. Microneedle arrays as the name indicates, are micron-sized needles, which upon insertion into the skin result in formation of aqueous conduits forming a passage for the vaccine antigens towards the immune-competent skin layers. Due to their short needle length, they avoid contact with the nerve endings in the dermis thus remain to be a painless mode of immunization. This opens a new avenue of vaccine delivery through an effective, painless and patient-friendly route of administration. The success of immunization via skin using microneedles inspired us to evaluate the potential of delivering a breast cancer vaccine through this route. This approach further can potentially be translated to a clinical setting where the patient undergoes a surgery for removal of the tumor and these tumor cells can serve as source of antigens for an individualized particulate vaccine, which can be administered therapeutically to avoid relapse Specific Aims The American Cancer society estimates approximately 232,670 women will report for breast cancer in USA alone. According to the national cancer institute around 40,000 deaths are projected to occur due to breast cancer in USA (Siegel, Ma, Zou, & Jemal, 2014). Current treatment strategies for breast cancer involves some type of surgery to remove cancerous tissue followed by chemotherapy, radiation therapy or hormone therapy. Both chemotherapy and radiation therapy do not act specifically against tumor cells and therefore have serious side effects on normal cells also due to metastatic tumor spread many (20-25%) patients experience a relapse of the tumors despite these interventions. Thus a vaccine that can prevent the tumor growth as well as prevent metastasis of tumor cells is the need of the time.

We propose to formulate a microparticulate vaccine formulation for metastatic breast cancer by using a murine metastatic breast cancer cell line 4T1 for transdermal administration through microneedles. We hypothesize that the microneedle based microparticulate vaccine formulation is a viable dosage form that may result in significant reduction in tumor growth as well as prevention of metastasis in murine model.

Aim 1: To prepare, characterize and evaluate the immunogenicity of biodegradable 4T1 metastatic breast cancer vaccine microparticles Approach: Tumor associated antigens present in whole cell lysate of 4T1 cell line will be added to a mix of biodegradable polymers and formulation will be spray dried to obtain the microparticles. Subsequently, the microparticles will be incorporated into microneedles and will be characterized for physiochemical parameters and induction of innate immunity.

Impact: Microparticles will serve to protect the tumor associated antigens present in the whole cell lysate vaccine formulation and result in efficient uptake and presentation by dendritic cells.

Aim 2: To evaluate the cell surface expression on dendritic cells treated with the microparticulate vaccine formulation.

Approach: Dendritic cells will be exposed to particulate vaccine with/without adjuvants to determine co-stimulatory expression required for activation of T and B lymphocytes Impact: The increase or decrease in expression of surface markers on the cells will enable us to understand the interaction between the innate and adaptive immune system. Antigen presentation by dendritic cells stimulates other immune pathways to trigger humoral and cell mediated immune responses.

Aim 3: To determine the efficacy of the particulate 4T1 metastatic breast cancer vaccine administered by the microneedle based transdermal route in murine breast cancer model Approach: Balb/c female mice will be injected with 4T1 breast cancer cells and then will be vaccinated via the transdermal route using dissolving microneedle. Tumor volume and weight measurement will be taken regularly. At the end of the study different immune organs (e.g. lymph nodes, spleen) will be analyzed to determine if there is any increase in specific immune responses in treatment groups compared to control groups.

Impact: A significant reduction in the tumor volume and metastasis and increase in immune response will in treatment groups will suggest that the vaccine is efficacious in treating metastatic breast cancer.

Innovation

Multiple approaches will be applied to ensure potent and efficacious breast cancer therapy. Following innovative approaches will be combined:

Currently there is no approved FDA vaccine against breast cancer. Development of an efficacious vaccine will have a major impact in the field of cancer immunotherapy as similar approach could be used in other types of cancers.

Particulate nature of vaccine ensures sustained release of antigens, higher internalization and stronger immune response than vaccine solution Use of vaccine adjuvants such as MF59 to enhance the immunogenicity of tumor antigens will enhance the immunogenicity of weakly immunogenic cancer antigens.

Paradigm Shift: Primary breast cancer is currently treated with surgical resection, chemotherapy and/or radiotherapy. Despite these interventions many (20-25%) patients experience a relapse of the tumors due to micrometastatic tumor spread undiagnosed at the time of surgical resection. This proposal will explore the feasibility of eliminating residual breast cancer cells/tumors and avoiding disease recurrence using a primary vaccine treatment approach in a murine model of breast cancer. We aim to induce strong, broad and long lasting immunity, using adjuvant such as MF 59 and alum, which have demonstrated promising results in vaccine efficacy studies where they act as immune potentiator. We also aim to develop a novel treatment strategy consisting of a simultaneous use of low dose immuno-modulating chemotherapeutic drug and vaccine therapy for treatment of breast cancer. A low dose of cyclophosphamide, which causes not toxicity in humans, will be used to inhibit regulatory T cell levels. We expect this combination to create a stronger immune response against tumor cells. With this strategy, we aim to induce strong, broad and long lasting immunity against breast cancer resulting in a survival advantage in individuals afflicted with this disease. Our proposal focuses on breast cancer with the goal of clinical translation. However, microparticle vaccine technology could have widespread applications in other cancers and/or infectious diseases as well.

Preliminary Studies

The goal of this study was to determine the formulation parameters of a microparticulate vaccine for metastatic breast cancer using murine 4T1 metastatic breast cancer cell line.

Specific Aim 1: To develop and characterize microparticulate formulation for transdermal delivery of metastatic breast cancer vaccine Vaccine Preparation Briefly, whole cell lysate for murine breast cancer cell line (4T1) was prepared by using hypotonic lysis buffer (10 mM Tris and 10 mM NaCl) and further subjected to five freeze thaw cycles at −80° C. and 37° C. for 10 minutes each. At the end of last freeze thaw cycle, cell lysis was confirmed using trypan blue dye exclusion assay; presence of dead cells confirmed the end point. The whole cell lysate (WCL) thus obtained was stored at −80° C. for further use.

Formulation Preparation

The 4T1 antigen loaded vaccine particles were prepared by spray-drying an aqueous suspension containing whole cell lysate WCL, ethyl cellulose, cellulose acetate phthalate (CPD), hydroxyl-propyl methylcellulose acetate succinate (HPMCAS) and trehalose using the following formula: Whole cell lysate WCL=10% w/w, Ethyl cellulose=35% w/w, Cellulose acetate phthalate (CPD)=25% w/w, Hydroxyl-propyl methylcellulose acetate succinate (HPMCAS)=25%, Trehalose=5% w/w. This final mixture was then spray dried using Buchi 290 Mini Spray Dryer (Buchi Corporation, Newcastle, Del.) with an inlet temperature of 125° C. and outlet temperature of 80° C. The particles were stored at −20° C. until further use. Adjuvant microparticles were prepared following the same procedure with adjuvant loading of 2.5% w/w.

Vaccine and adjuvant microparticles were incorporated into dissolving microneedle patches for vaccine administration. Dissolvable microneedles mainly deploy PDMS micromolds which are made from a master structure of microneedles. Briefly, polydimethylsiloxane (PDMS) was poured onto the stainless steel master structure obtained from Micropoint Technologies INC, Singapore. The microneedles were made using the following formula: Drug/

Particles=10% w/w, Trehalose=25% w/w, Maltose=25% w/w, PVA=20% w/w, HPMC=20% w/w The resulting suspension was then added to mold avoiding air bubbles. These molds were then centrifuged for 5-10 minutes. Then the molds were dried overnight. After overnight drying dried microneedles were collected to use for the administration of vaccines.

Size and Zeta Potential

Spray dried particles were analyzed for their size and zeta potential. Antigen loaded microparticles were suspended in citrate buffer (100 mM, pH 4.0) and particle size was measured using Spectrex laser particle counter (Spectrex Corp. CA). Zeta potential of these microparticles was measured using Malvern Zetasizer Nano ZS (Malvern Instruments, Worcs, UK). For morphology studies, vaccine microparticles were visualized using scanning electron microscope (Phenom World Pure Scanning electron microscope). The particle size was within a range of 1-4 μm. The size and shape of particles was confirmed using scanning electron microscopic images (FIGS. 12A and 12B). The particles are doughnut shaped and porous in nature. The particles have a positive zeta potential of 7 to 9 mV. Positive zeta potential helps prevent aggregation and aids uptake of particles by dendritic cells.

Specific Aim 2: To evaluate the immunogenicity of vaccine loaded microparticles.

Nitric oxide assay is an important marker for innate response. Antigen-presenting cells like dendritic cells release nitric oxide upon exposure to an antigen. In this study we found that there is significantly higher amount of nitric oxide released in the supernatant of cells exposed to vaccine microparticles compared to vaccine solution and blank microparticles. Vaccine microparticles induced nitric oxide release of 70.03±10.32 μM of nitrite compared to 10.37±4.21 μM of nitrite by lysate solution (see FIG. 13).

Dendritic cells (DCs) are one of the major effector cells of immune system. They form an important part of the linkage between innate and adaptive immune response. DCs phagocytose the microparticles and lyse the microparticle in order to express the antigen on its surface (Andrianov & Payne, 1998; Hardy et al., 2013; L Thiele et al., 2001; Lars Thiele, Diederichs, Reszka, Merkle, & Walter, 2003). Therefore we evaluated the ability of dendritic cells to express the vaccine antigens as either MHC I or MHC II. Also, we evaluated the effect of delivery of antigen via microparticles on various important cell surface co-stimulatory signals such as CD40 and CD80.

Figure 15:
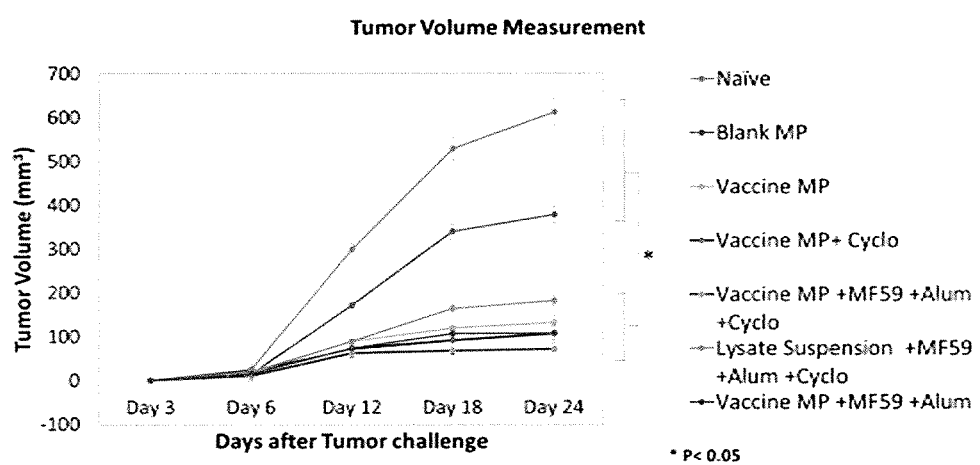
Figure 16A:
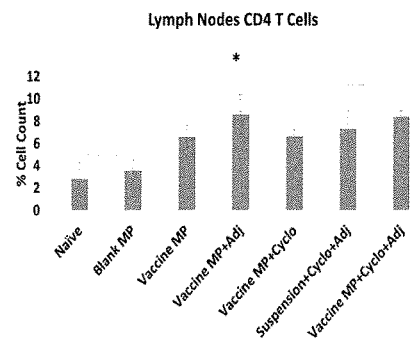
Figure 16B:
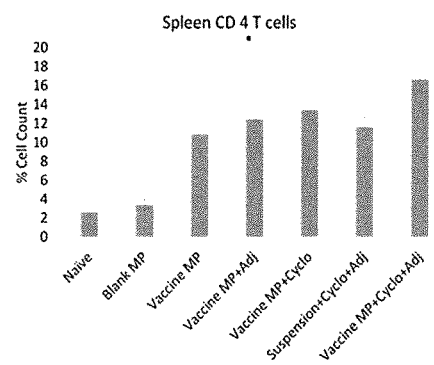
Figure 16C:
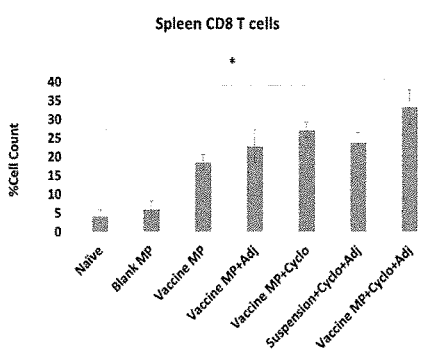
Figure 16D:
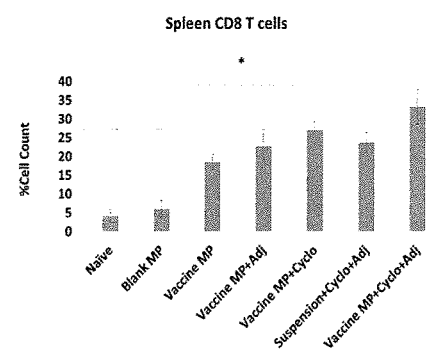
Figure 17:
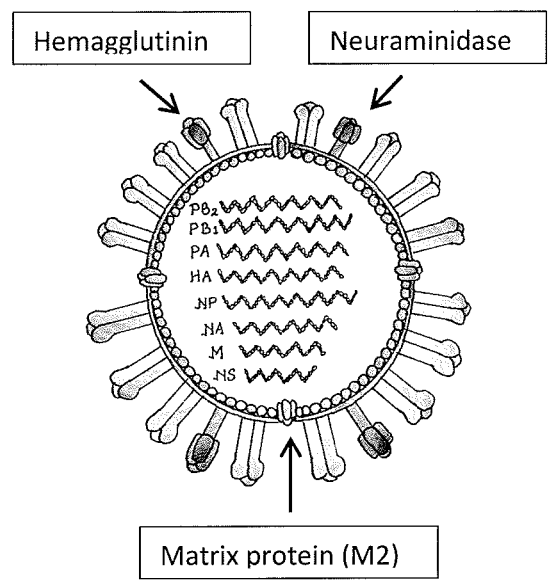
Figure 18:
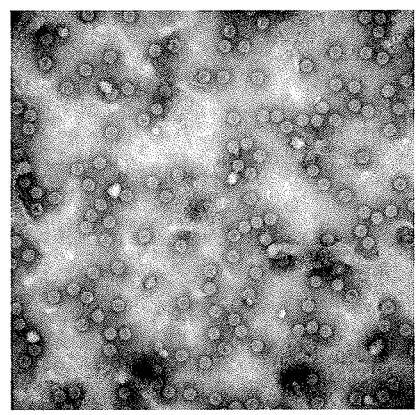
Figure 19:
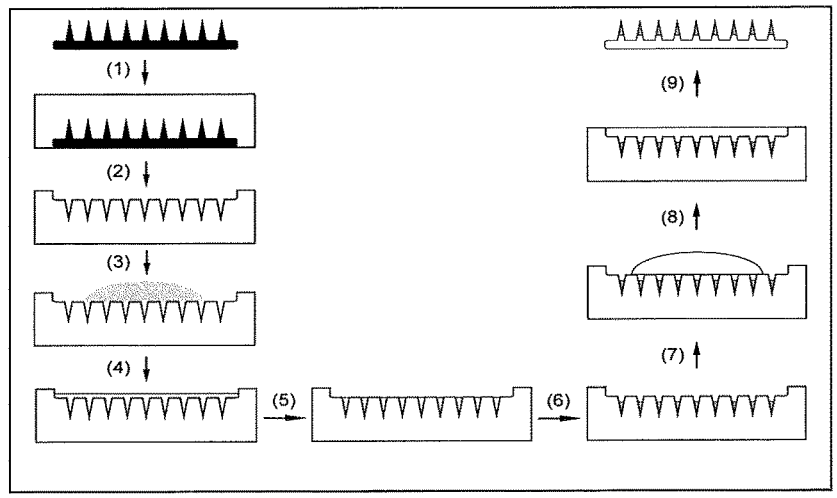
Figure 20:
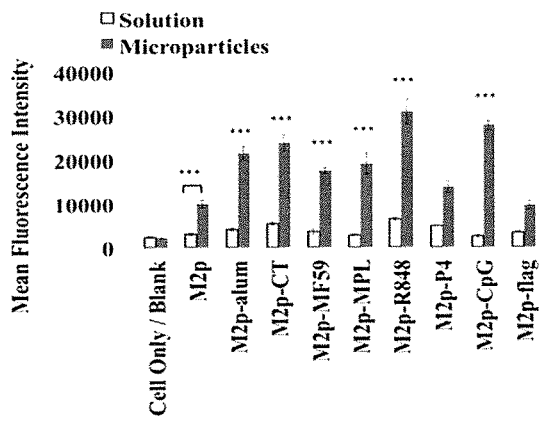
Figure 21:
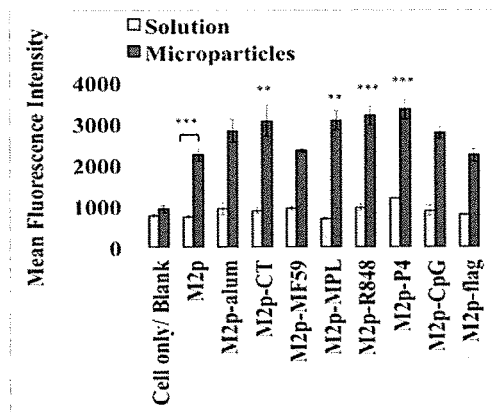
Figure 22:
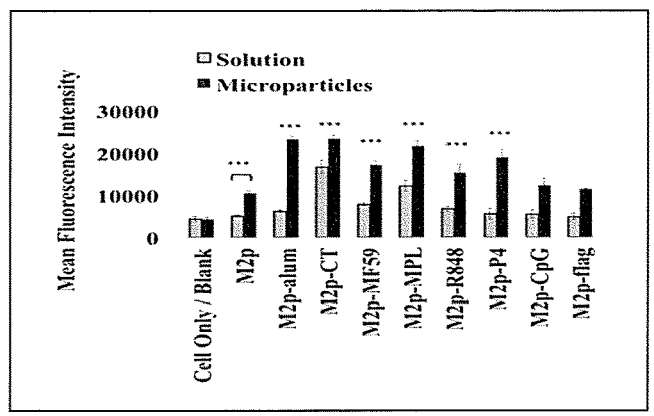
Figure 23:
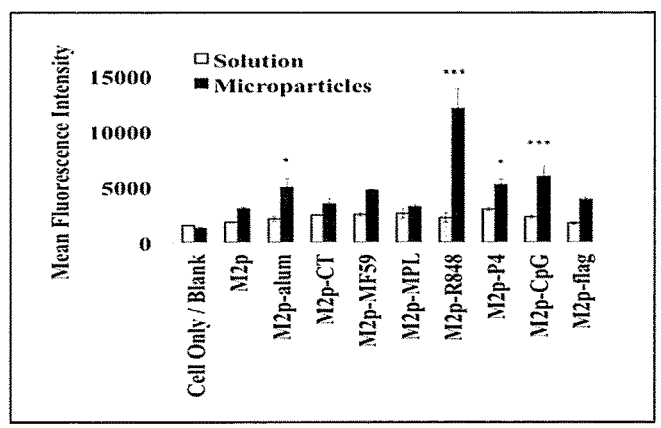

Dendritic cells were incubated with vaccine microparticles, blank microparticles and vaccine (lysate) suspension for 16 hrs. As seen in FIGS. 14A-D (induction of co-stimulatory signals—MHC I, MHC II, CD40 and CD80 on dendritic cells pulsed with 4T1 breast cancer vaccine microparticles), vaccine microparticles induced CD 40 and CD86 expression. Both CD80 and CD40 are important for binding to T cell. There was significantly higher induction of CD 40 and CD80 in presence of vaccine microparticles compared to vaccine solution and blank microparticles. The whole cell lysate contains proteins which can be expressed as either MHC I and MHCII molecules on the antigen presenting cells. Here we can see that the antigen is presented as both MHC I and MHC II molecule. Antigen presentation is higher when given as a microparticle compared to vaccine suspension. FIG. 15 is a graph of tumor volume measurement. FIGS. 16A-D are graphs of In vivo CD4 and CD8 T cell response in different treatment groups as percent cell count measurement of lymph nodes CD 4 T cells (FIG. 16A), spleen CD 4 T cells (FIG. 16B), spleen CD 8 T cells (FIG. 16C) and spleen CD 8 T cells (FIG. 16D). Table 2 shows a progression of metastasis to lung, lymph node and liver in different treatment groups.

TABLE 2

| Groups | Lung | Lymph Node | Liver |
|---|---|---|---|
| Naïve | + | + | + |
| Blank MP | + | + | − |
| Vaccine MP | + | − | − |
| Vaccine MP + Alum MP + MF 59 MP | − | − | − |
| Vaccine MP + Cyclophosphamide | − | − | − |
| Vaccine MP + Alum + MF 59 + Cyclophosphamide | − | − | − |
| Vaccine suspension + Alum + MF 59 + Cyclophosphamide | − | + | − |

EXAMPLE 2 REFERENCES

1. Mittendorf E A, Alatrash G, Xiao H, Clifton G T, Murray J L, Peoples G E. Breast cancer vaccines: ongoing National Cancer Institute-registered clinical trials. Expert Rev Vaccines. 2011 June; 10(6):755-74.
2. Nemunaitis J, Sterman D, Jablons D, Smith J W, Fox B, Maples P, et al. Granulocyte-macrophage colony-stimulating factor gene-modified autologous tumor vaccines in non-small-cell lung cancer. J Natl Cancer Inst. 2004 Feb. 18; 96(4):326-31.
3. Shastri P N, Kim M-C, Quan F-S, D'Souza M J, Kang S-M. Immunogenicity and protection of oral influenza vaccines formulated into microparticles. J Pharm Sci. 2012 October; 101(10):3623-35.
4. Uddin A N, Bejugam N K, Gayakwad S G, Akther P, D'Souza M J. Oral delivery of gastro-resistant microencapsulated typhoid vaccine. J Drug Target. 2009 August; 17(7):553-60.
5. Yeboah K G, D'souza M J. Evaluation of albumin microspheres as oral delivery system for *Mycobacterium tuberculosis* vaccines. J Microencapsul. 2009 March; 26(2):166-79.
6. Akalkotkar A, Tawde S A, Chablani L, D'Souza M J. Oral delivery of particulate prostate cancer vaccine: in vitro and in vivo evaluation. J Drug Target. 2012 May; 20(4): 338-46.
7. D'Souza B, Bhowmik T, Shashidharamurthy R, Oettinger C, Selvaraj P, D'Souza M. Oral microparticulate vaccine for melanoma using M-cell targeting. J Drug Target. 2012 February; 20(2): 166-73.
8. Drutz J E, Ligon B L. Special article: Polio: Its history and its eradication. Semin Pediatr Infect Dis. 2000 October; 11(4):280-6.
9. Lopez-Gigosos R M, Plaza E, Diez-Diaz R M, Calvo M J. Vaccination strategies to combat an infectious globe: oral cholera vaccines. J Glob Infect Dis. 2011 January; 3(1):56-62.
10. Huang C-F, Wang C-C, Wu T-C, Wu K-G, Lee C-C, Peng H-J. Neonatal sublingual vaccination with *Salmonella* proteins and adjuvant cholera toxin or CpG oligodeoxynucleotides induces mucosal and systemic immunity in mice. J Pediatr Gastroenterol Nutr. 2008 March; 46(3): 262-71.
11. Kataoka K, McGhee J R, Kobayashi R, Fujihashi K, Shizukuishi S, Fujihashi K. Nasal Flt3 ligand cDNA elicits CD11c+CD8+ dendritic cells for enhanced mucosal immunity. J Immunol Baltim Md. 1950. 2004 Mar. 15; 172(6):3612-9.

12. Zhang T, Hashizume T, Kurita-Ochiai T, Yamamoto M. Sublingual vaccination with outer membrane protein of *Porphyromonas gingivalis* and Flt3 ligand elicits protective immunity in the oral cavity. Biochem Biophys Res Commun. 2009 Dec. 18; 390(3):937-41.
13. Banchereau J, Steinman R M. Dendritic cells and the control of immunity. Nature. 1998 Mar. 19; 392(6673): 245-52.
14. Xiang R, Luo Y, Niethammer A G, Reisfeld R A. Oral DNA vaccines target the tumor vasculature and microenvironment and suppress tumor growth and metastasis. Immunol Rev. 2008 April; 222: 117-28.
21. Bozeman E N, Shashidharamurthy R, Paulos S A, Palaniappan R, D'Souza M, Selvaraj P. Cancer vaccine development: designing tumor cells for greater immunogenicity. Front Biosci Landmark Ed. 2010; 15:309-20.
32. Shah A U, D'Souza M J. Sustained-release interleukin-12 microspheres in the treatment of cancer. Drug Dev Ind Pharm. 1999 September; 25(9):995-1004.
34. Kubin M, Kamoun M, Trinchieri G. Interleukin 12 synergizes with B7/CD28 interaction in inducing efficient proliferation and cytokine production of human T cells. J Exp Med. 1994 Jul. 1; 180(1):211-22.

Example 3

Transdermal Particle Based Microneedle Against Influenza

The Influenza virus is an RNA virus, part of the Orthomyxoviridae family.[1] There are three main subtypes of influenza: A, B and C.[1] Subtype A infects nonhuman hosts, however transmission from these hosts to humans can occur which can have a serious impact and lead to a pandemic crisis.[1] Subtypes B and C only infect humans.[1]

Influenza is enclosed in a lipid bilayer that houses the RNA that codes for all the virus' proteins (FIG. 17).1 There are two major glycoproteins, hemagglutinin (HA) and neuraminidase (NA) which are commonly used to define the strains of all the various subtypes of influenza viruses.1 These two glycoproteins undergo mutation and thus give rise to new strains which causes a major challenge for the human immune system to be able to defend against all the various strains.1 In recent years, the matrix 2 protein (M2) which is an ion channel located on the membrane of the virus that is responsible for maintaining specific conditions during viral entry into the host, has been shown to be conserved amongst the various strains.2 This characteristic of the M2 protein serves as a basis for the development of a potential universal vaccine.

According to the Center for Disease Control and Prevention (CDC), the best method of protection against influenza is vaccination prior to the start of influenza season.3 The major goal of vaccines is to provide immunity, which is a term used to describe the ability of the host to protect itself against a foreign pathogen.4 This is dependent on the coordination of two major systems the innate and adaptive.4 Microorganisms such as bacteria and viruses that infiltrate the host for the first time are met by the innate immune system, which include macrophages that are activated and release proteins known as cytokines and chemokines that signal other cells to the site of infiltration.5 A vital class of immune cells that arrive to the site are dendritic cells (DCs) which help by engulfing these pathogens thus causing induction of the adaptive immune response.5 Following encounter with the pathogen, dendritic cells enter a developmental program referred to as maturation.6 The function of mature DC's is not to destroy pathogens, but to become highly effective antigen-presenting cells (APCs) and carry antigens (foreign protein or molecules) to lymphoid organs and present them to other immune cells.5

Antigens themselves can be classified as exogenous or endogenous, exogenous implies that the antigen enters the host from the external environment (i.e. injected vaccine), endogenous antigens are generated within cells of the host (i.e. proteins encoded by viruses).5 As the name suggests antigen presentation is done by none other than antigen-presenting cells (APCs) and is unique and dependent on the nature of the antigen (exogenous or endogenous).5 Exogenous antigens are dissected and fragments are displayed on molecules known as class II major histocompatibility complexes (MHC II) on the surface of APCs.5 Endogenous antigens are dissected similarly to exogenous antigens and fragments are presented on class I major histocompatibility complexes (MHC I).5 Once antigen processing and presentation occurs, there is requirement of cell to cell contact, also known as an immunological synapse between antigen-presenting cells and a subset of immune cells known as T lymphocytes.5 Antigens presented on MHC class II initiates binding to the T cell receptor (TCR) on helper T lymphocytes categorized as CD4+ T cells and antigen presentation on MHC class I binds to the T cell receptor (TCR) on cytotoxic T cells categorized as CD8+ T cells.5 Binding of these molecules to T cells does not necessarily result in activation, the binding of a molecule known as intracellular adhesion molecule 1 (ICAM-1) on APCs to leukocyte function-associated antigen 1 (LFA-1) on T cells is important for T cell proliferation and differentiation.5 There is a phenomenon known as cross-presentation predominantly done by mature DC's where there is transfer of endogenous antigens to the MHC class II pathway, a mechanism is which both class I and class II pathways of antigen presentation can be used.5 The main goal of influenza vaccination is to utilize this phenomenon of cross-presentation to induce an enhanced and more effective immune response against viral antigens of influenza.

Administration of vaccines targets the adaptive immune system which is classified into antibody-mediated and cell-mediated machineries.4,5 One machinery known as antibody-mediated is produced by a group of immune cells known as B-lymphocytes.4 Upon encounter with an antigen, B lymphocytes descend into plasma cells that are responsible for secreting proteins known as antibodies that aid in destruction of the antigen.4 The other machinery known as cell-mediated is regulated by T lymphocytes.4 There are three major subsets of T lymphocytes: cytotoxic, suppression and helper.4 Cytotoxic T lymphocytes aid in the destruction of cells that may be infected and recruit other cells to destroy the pathogen that caused the infection in these cells.4 Suppressor T lymphocytes coordinate the immune response by regulating the level of the response.4 Helper T lymphocytes activate other immune cells which aid in destruction of the pathogen, i.e. plasma cells to release antibodies.4 Vaccines are known to activate these machineries by first exposure of the antigen to immune cells, leading to recognition of the antigen following second exposure and thus allowing for rapid immune response.4 This phenomenon is known as immunological memory.4

There are various types of antigens that can be incorporated into vaccines.6 From the emergence of vaccines, which were originally practiced by Edward Jenner, development of influenza vaccines have been focused on the use of either dead, attenuated or inactivated forms of the virus.5 Recent discoveries in recombinant technology have led to the development of novel systems such as viral vectors, recombinant proteins, DNA and subunit vaccines.6 Virus-like particles (VLPs) have played an important role in vaccine development, using recombinant methods and the first VLP vaccine was marketed for Hepatitis B in 1986, followed by a VLP vaccine against the human papillomavirus (HPV) in 2006.5 Virus-like particles (VLPs) are multiple repeats of a protein or antigen that resembles the native form and organization of the virus, minus its genome; therefore it is a safer candidate for use in a vaccine.5 The nature of VLP's allow for presentation of antigenic proteins, that have the ability to enhance antibody production leading to improved immune response.5 Up to date, VLPs have been constructed for approximately 30 viruses including influenza.5 The hemagglutinin and neuraminidase VLPs have been constructed and used for research purposes, however the persistent challenge is that these two proteins mutate in various strains of the influenza virus and therefore our focus is to utilize the matrix 2 protein (M2), construct a VLP and test its potential as a vaccine.2

In order to generate a dynamic immune response, vaccines should meet two main criteria, it should produce long-term protection and should be specific to the antigen.8 To meet these criteria, compounds known as adjuvants are used to enhance activation of the immune system.8 In the 1920's aluminum based compounds demonstrated excellent adjuvant activity and have been licensed and are widely used in human vaccines today.8 Research has shown that aluminum based adjuvants enhance immunogenicity by producing a depository at the site of administration allowing for sustained release of the antigen.8 This sustained release mechanism allows for increased interface between the antigen and cells of the immune system.8 One of the most common entry sites for infectious diseases including influenza is through mucosal membranes, therefore researchers have sought out the use of adjuvants that target mucosal membranes to improve vaccines.9 Immune cells express a family of proteins categorized as toll-like receptors which help in the elimination of pathogens, therefore adjuvants that target these toll-like receptors can enhance the immunogenicity of vaccines.10 Toll-like receptor 4 (TLR-4) activation induces mucosal and systemic immunity in influenza viral infection, through the release of pro-inflammatory molecules.10 Monophosphoryl Lipid A (MPL-A) originally sequestered from *Salmonella minnesota* R595 is a TLR-4 ligand that generates resistance towards viral infections by modulation of cytokine release.10 MPL-A is approved for human use and is incorporated in combination with aluminum hydroxide collectively referred to as AS04 and marketed in Cervarix™, a vaccine against the human papillomvirus (HPV).11 Similarly, this principal combination will be added to our matrix 2 protein virus-like particle (M2 VLP) antigen for construction of an immunomodulating vaccine against Influenza.

Entering into delivery options for vaccines, there are several important considerations and challenges for vaccine delivery.12 In order to prepare a good vaccine, there are several parameters that must be contemplated that allow for minimal change to the antigen incorporated into the vaccine, especially in regards to its integrity and activity.12 It has been suggested in the past decade that particulate antigens have an advantage over soluble antigens in that they mimic the nature of the pathogen and are taken up better by antigen presenting cells leading to activation of multiple immune pathways and thus a more effective response.12 Internalization of particulate antigens has also illustrated the ability for antigen cross-presentation, suggesting another reason why the immune response may be enhanced.12 Particulate antigens have a prolonged release period and can be delivered in higher doses in comparison to soluble antigens.12 There are several methods of delivering antigens as particulates, one of which is incorporating them into polymers which can be tailored with specific chemical and physical characteristics capable of activating pathways in the immune system.12 Polymers made up of a biodegradable matrix are an attractive approach because they release the encapsulated entity in a controlled manner and are safe for use in development of vaccines.12 On the basis of particulate systems, our goal will be to encapsulate the M2 VLP into a biodegradable matrix and evaluate immune system activation.

The most widely used route for administration of vaccines has been parenteral delivery, however a lot of focus has been placed on non-injectable methods, one of which utilizes the skin, which is the first line of defense against pathogens.13 The skin is rich in antigen presenting cells (APCs), known as Langerhans cells (LCs) in the epidermis and dermal dendritic cells in the dermis which can activate the T and B lymphocytes and therefore is an excellent route of delivery for vaccines.13,14 There are a multitude of methods that have been utilized for delivery of proteins as well as drugs across the skin.14 A straightforward way to deliver molecules into the skin is the use of microneedles.14 This method has been illustrated to be painless and depending on the size and length of the needles, they can permeabilize the skin, allowing for simple delivery of biologics.14

Innovation

Current influenza vaccines on the market use whole inactivated forms of the virus and use multiple antigenic strains that need to be modified annually to produce the desired antibodies capable of protecting against the virus. However with the rapid rate of mutation in the two major glycoproteins hemagglutinin (HA) and neuraminidase (NA), there is a need for an alternative approach for development of a universal vaccine against influenza. Subsequently, particulate formulations that encapsulate the matrix 2 protein virus-like particle (M2 VLP) that is conserved among all strains was designed to overcome this limitation. Moreover, the transdermal route for vaccination has been evaluated by many research groups, employing microneedles to allow for permeabilization of the skin allowing for delivery of therapeutics. Nevertheless, the novelty of this proposed work is underlined by the delivery of the M2 VLP particulate vaccine into the skin to target dermal dendritic cells to induce immunity. Additionally, to assess protection and efficacy of the vaccine, a live virus challenge will be conducted. Exploring these objectives are intended to hopefully bring us a step closer and advance our goal in seeking a universal vaccine for influenza.

Preliminary Studies

Influenza is one of the most devastating infectious diseases due to the ease of spread. Memory response after primary infection is critical, however due to the high rate of mutation of the virus; the antibodies produced in primary infection are not specific and are unable to protect against secondary influenza infection. The immune system is composed of two major classes of immunity, innate and adaptive immunity. Adaptive immunity is subdivided into humoral and cell-mediated responses. The fight against influenza involves both humoral and cell-mediated immune responses. In addition to humoral mediated antibody production, activation of T lymphocytes, both CD4+ and CD8+ T cells are important for recovery against influenza infection. Priming of the host defense using vaccines is key for prevention of influenza infection.

Figure 24:
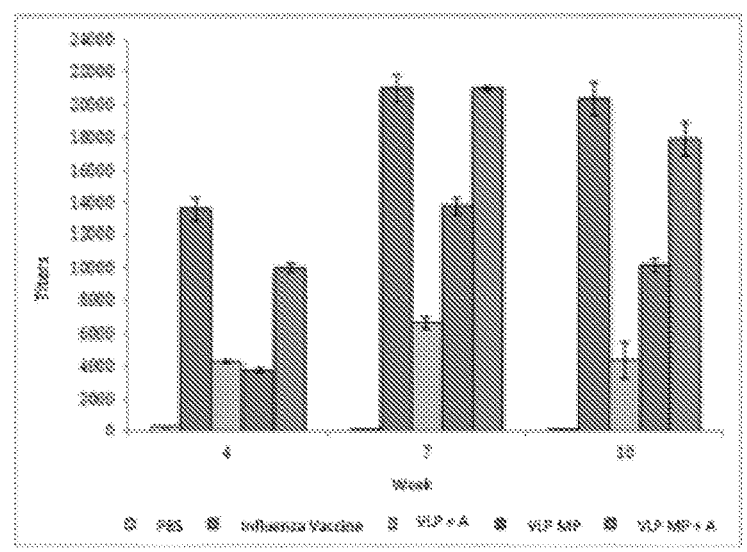

Transdermal delivery of particulate vaccines has been shown to induce protective immunity against influenza, however the mechanism of this response is not well understood. It is thought that differentiation of T cells into Th1 and Th2 cells is vital for delineation of immune cells that lead to immunological memory. Th1 differentiation leads to CD8+ activation of cytokines that then help to convert to memory T cells. Th2 differentiation leads to CD4+ activation of cytokines that can lead to both T and B cell memory. In order to investigate this mechanism, the Th1 and Th2 immune responses were explored following transdermal vaccination with a particulate system incorporating the A/PR/8/34 (H1N1) inactivated influenza virus and delivery using a micro needle injector.

Formulation of Microparticulate Vaccine

The particulate formulation was first prepared using the spray drying method. The inactivated influenza virus was incorporated into a polymer matrix with the following composition: 20% (w/w) cellulose acetate phthalate (Aquacoat® CPD), 35% (w/w) HPMCAS and 33% (w/w) of ethyl cellulose (Aquacoat® ECD). Other constituents include trehalose (5%), chitosan (5%), tween 20 (0.5%) and lastly Inactivated influenza virus (1.5%). Following preparation, the microparticulates were visualized using transmission electron microscopy (FIG. 19). Size and charge are illustrated in Table 3.

TABLE 3

| | |
|---|---|
| Average Size | 900 nm ± 7.53 |
| Zeta Potential | −12.23 mV |
| Encapsulation Yield | 86.41 ± 2.38% |
| Percentage Yield | 95.64% |

Formulation of Microneedles

Mice were immunized transdermally using dissolving microneedles. Dissolving microneedles, intended for the painless transdermal release of encapsulated pharmaceutical agents after dermal insertion, were developed as a solution to the safety issue. Dissolvable microneedles mainly deploy PDMS micromolds which are made from a master structure of microneedles (FIG. 19). Briefly, Polydimethylsiloxane (PDMS) was poured onto the stainless steel master structure obtained from Micropoint Technologies INC, Singapore (Step 1-3; FIG. 19). The M2e VLP formulation was then spray dried respectively. The microneedle formulation includes 10% of M2e VLP, 25% trehalose, 25% maltose, 20% polyvinyl alcohol and 20% hydroxypropylmethylcellulose acetate succinate (HPMCAS). The formulation was prepared beginning with the addition of PVA, HPMC, Maltose and Trehalose to a microcentrifuge tube, followed by the addition of ammonium hydroxide (NH4OH) to the microcentrifuge tube. Once dissolved, this formulation was then added to a microneedle mold avoiding air bubbles (FIG. 19). These molds were then placed straight into 50 mL centrifuge tubes. Centrifugation was done in a fixed angle centrifuge in order to remove air bubbles and to force the formulation into the microneedles mold. The maximum speed was 2000 rpm which was achieved step wise, in order to avoid jerking in the rotation process, time for which centrifugation should be done was 5-10 min. After this centrifugation step, the backing layer was added and centrifuged repeatedly in the same manner. The molds were placed in in tubes and then in an incubator at 37 degrees C. overnight.

To investigate the efficacy of this M2 VLP formulation. Dendritic cells play a major role in immune system activation and are well known for their ability to release chemical messengers known as cytokines or chemokines, followed by activation of the adaptive immune system. Dendritic cells take up antigens and present them on major histocompatibility complexes I and II (MHC I, MHC II).

The soluble and particulate vaccines (with and without adjuvants) were introduced to dendritic cells with the same amount of antigen and adjuvant. The induced cells were incubated for 20 hours at 37° C. with 5% CO2. Different markers can be used to evaluate the antigen presentation on APCs in ex-vivo or in-vitro studies. Some of these markers include CD40, MHC class II, CD80, and CD86. Both expressions of CD40 and MHC II on the surface of APCs are necessary for a successful stimulation of T cells from APCs as demonstrated in FIGS. 20 and 21 (18). CD80 and CD86 molecules are normally expressed on activated APCs and provide critical co-stimulatory signals for T cell activation and survival (19). FIG. 20 shows that M2p MP group showed statistically higher CD 40 expression compared to M2p solution group. Except for alum, MF59, CpG and flagellin groups, all other adjuvant treated groups showed significant increase in CD40 expression levels compared to M2P MP alone. FIG. 21 shows that the M2p MP group showed statistically higher CD 40 expression compared to M2p solution group. Except for P4 and Flag, MHC II expression was elevated in all adjuvant treated groups compared to M2p MP. Elevated MHC II expression will elicit a T-helper cell mediated response leading to antibody production against the antigen. In FIGS. 22 and 22, the microparticulate vaccine enhanced the CD80 expression but not the CD86 expression, compared to these expressions of the soluble vaccine group. In FIG. 22, the M2p MP group showed statistically higher CD80 expression level compared to the M2p solution group. CD 80 expression was elevated in Alum, CT, MF50, MPL, R848 and treated groups. In FIG. 23, there was no significant difference in CD 86 expression between soluble and microparticulate M2p vaccines. CD 86 expression was elevated in R848, P4 and CpG treated groups compared to M2p MP.

Table 4 shows the group, treatment, route, dose and number of doses.

TABLE 4

| Group Name | Treatment | Route | Dose (μg) | # of Doses |
|---|---|---|---|---|
| Naïve | PBS | Transdermal | — | 3 |
| Influenza Vaccine | Inactivated virus | Intramuscular | 10 | 3 |
| Free antigen | M2 VLP | Transdermal | 10 | 3 |
| Antigen loaded particulates | M2 VLP | Transdermal | 10 | 3 |
| Antigen loaded particulate with adjuvant | M2 VLP | Transdeimal | 10 | 3 |

For animal experiments, 6-8 weeks old male C57BL/6 mice were immunized with 3 doses at 3-week intervals. Four weeks after the final booster dose, mice were challenged with a lethal dose of mouse adapted A/Philippines/2/82 (H3N2) live influenza virus. Mice were monitored daily to record changes in weight and mortality. Following 25% loss in body weight, animals were sacrificed for further analysis. by Mercer University IACUC review board and conducted under the guidelines of Mercer University IACUC.

Blood samples were collected before immunization and every 3 weeks, samples were stored in −20° C. until analysis. Specific serum antibody for the matrix protein (M2)

were assessed using ELISA. Coating antigens were the M2 peptide or inactivated virus at a concentration of 200 ng/well. Serum samples were used for detection of primary antibody and horseradish peroxidase (HRP) conjugated goat anti-mouse IgG, IgG1 and IgG2a were used as secondary antibodies to determine total amount of antibody and antibody isotypes. The substrate 3,3',5,5'-Tetramethylbenzidine (TMB) was used, followed by 0.3M sulfuric acid (H2SO4) as stop solution for detection of color. The optical density was taken at 450 nm by a spectrophotometer. See FIG. 24.

C) Evaluation of T Cell Responses

Figure 25:
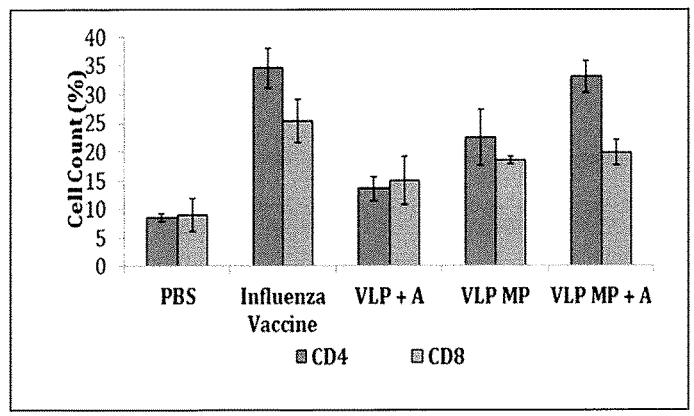

After the animals are sacrificed, the lymph node was extracted (i.e. spleen and lymph node) and made into single cell suspensions. The single cell suspensions were stained with fluorescence-conjugated antibodies specific to T cell phenotypes, helper T cells (CD4+) and cytotoxic T cells (CD8+) and quantified using flow cytometry. See FIG. 25.

EXAMPLE 3 REFERENCES

1. Clancy S. Genetics of the influenza virus. Nat Educ. 2008; 1(1):83.
2. Kim M-C, Song J-M, Eunju O, Kwon Y-M, Lee Y-J, Compans R W, et al. Virus-like particles containing multiple M2 extracellular domains confer improved cross-protection against various subtypes of influenza virus. Mol Ther. 2013; 21(2):485-92.
3. Vaccines and Immunizations|Home|CDC [Internet]. [cited 2016 Jun. 20]. Available from: cdc.gov/vaccines
4. Health GBD of. Immunisation against infectious diseases. The Stationery Office; 2006.486 p.
5. Janeway C A, Travers P, Walport M, Shlomchik M J. Immunobiology: the immune system in health and disease. Vol. 1. Current Biology; 1997
6. Roldão A, Mellado M C M, Castilho L R, Carrondo M J, Alves P M. Virus-like particles in vaccine development. Expert Rev Vaccines. 2010; 9(10):1149-76.
7. Soema P C, Kompier R, Amorij J-P, Kersten G F. Current and next generation influenza vaccines: Formulation and production strategies. Eur J Pharm Biopharm. 2015; 94:251-63.
8. Petrovsky N, Aguilar J C. Vaccine adjuvants: current state and future trends. Immunol Cell Biol. 2004; 82(5):488-96.
9. Moldoveanu Z, Clements M L, Prince S J, Murphy B R, Mestecky J. Human immune responses to influenza virus vaccines administered by systemic or mucosal routes. Vaccine. 1995; 13(11):1006-12.
10. Mifsud E J, Tan A C-L, Jackson D C. TLR agonists as modulators of the innate immune response and their potential as agents against infectious disease. Front Immunol. 2014; 5:79.
11. Kim K S, Park S, Ko K-N, Yi S, Cho Y J. Current status of human papillomavirus vaccines. Clin Exp Vaccine Res. 2014; 3(2):168-75.
12. Xu Q, Hashimoto M, Dang T T, Hoare T, Kohane D S, Whitesides G M, et al. Preparation of monodisperse biodegradable polymer microparticles using a microfluidic flow-focusing device for controlled drug delivery. Small. 2009; 5(13):1575-81.
13. Song J-M, Wang B-Z, Park K-M, Van Rooijen N, Quan F-S, Kim M-C, et al. Influenza virus-like particles containing M2 induce broadly cross protective immunity. PLoS One. 2011; 6(1):e14538.
14. Kim K K, Pack D W. Microspheres for drug delivery. In: BioMEMS and Biomedical Nanotechnology. Springer; 2006 p. 19-50.
15. Savina A, Amigorena S. Phagocytosis and antigen presentation in dendritic cells. Immunol Rev. 2007; 219(1):143-56.
16. Théry C, Amigorena S. The cell biology of antigen presentation in dendritic cells. Curr Opin Immunol. 2001; 13(1):45-51.
17. Germain R N, Margulies D H. The biochemistry and cell biology of antigen processing and presentation. Annu Rev Immunol. 1993; 11(1):403-50.
18. Burgdorf S, Kurts C. Endocytosis mechanisms and the cell biology of antigen presentation. Curr Opin Immunol. 2008; 20(1):89-95.
19. Trombetta E S, Mellman I. Cell biology of antigen processing in vitro and in vivo. Annu Rev Immunol. 2005; 23:975-1028.
20. O'Hagan D T, Singh M, Ulmer J B. Microparticle-based technologies for vaccines. Methods San Diego Calif. 2006 September; 40(1):10-9.
21. Prausnitz M R, Langer R. Transdermal drug delivery. Nat Biotechnol. 2008; 26(11):1261-8.
22. Moran T M, Park H, Fernandez-Sesma A, Schulman J L. Th2 responses to inactivated influenza virus can be converted to Th1 responses and facilitate recovery from heterosubtypic virus infection. J Infect Dis. 1999; 180(3):579-85.
23. Avetisyan G, Ragnavolgyi E, Toth G T, Hassan M, Ljungman P. Cell-mediated immune responses to influenza vaccination in healthy volunteers and allogeneic stem cell transplant recipients. Bone Marrow Transplant. 2005; 36(5):411-5.
24. Wang B-Z, Gill H S, Kang S-M, Wang L, Wang Y-C, Vassilieva E V, et al. Enhanced influenza virus-like particle vaccines containing the extracellular domain of matrix protein 2 and a Toll-like receptor ligand. Clin Vaccine Immunol. 2012; 19(8):1119-25.
25. Kang S-M, Yoo D-G, Lipatov A S, Song J-M, Davis C T, Quan F-S, et al. Induction of long-term protective immune responses by influenza H5N1 virus-like particles. PLoS One. 2009; 4(3):e4667.
26. Kim T S, Sun J, Braciale T J. T cell responses during influenza infection: getting and keeping control. Trends Immunol. 2011; 32(5):225-31.
27. Bramwell V W, Perrie Y. Particulate delivery systems for vaccines: what can we expect? J Pharm Pharmacol. 2006; 58(6):717-28.

Example 4

Transdermal Particle Based Microneedle Against Human Papilloma Virus (HPV)

Human papillomaviruses (HPVs) are transmitted through sexual contact and most people are infected with HPV shortly after the onset of sexual activity (World Health Organization, 2015). There are more than 100 different types of HPVs, which are classified into two categories: non-oncologic and oncologic. Patients infected with the non-oncologic HPVs experience body warts on hands and feet, whereas these infected with the oncologic HPVs face development of genital warts or carcinogenic symptoms. More than 40 various HPV serotypes cause 90% genital warts such as HPV6, 11, 31, 33, 45, 52 and 58. Two HPV serotypes (16 and 18) are responsible for approximately 70% of cervical cancers and precancerous cervical lesions (Centers for Disease Control and Prevention, 2015, p. 1). Several symptoms of cervical cancer tend to appear only after the cancer has reached an advanced stage, which include irregular, intermenstrual or abnormal vaginal bleeding after sexual intercourse; back, leg or pelvic pain; fatigue, weight loss and loss of appetite. It takes 15 to 20 years for cervical cancer to develop in women with a normal immune system, while 5 to 10 years in women with a weakened immune system, such as those with untreated HPV infection.

Two commercial vaccines (Gardasil® from Merk, and Cervarix® from GlaxoSmithKline) are widely available in North America and Europe. The Centers of Disease Control and Prevention (CDC) recommends boys and girls to get vaccinated against HPV, especially between ages of 9 to 26. Both vaccines consist of HPV16 and HPV18 to prevent cervical cancers. Additionally, Gardasil® contained 9 different HPV serotypes (HPV 6, 11, 16, 28, 31, 33, 45, 52, and 58) which enhance the protection from cancers (cervical, vulvar, vaginal and anal) and genital warts (Centers for Disease Control and Prevention, 2015). However, the high cost of vaccine and trained personnel are a significant financial burden, especially in developing countries. Moreover, the vaccine needs cold-chain storage that adds to the vaccine cost. To overcome the challenges of injectable vaccines, vaccine solutions can be converted into micro/nano particles using a spray-drying or lyophilization process (Prathap Nagaraja Shastri et al., 2015).

The spray drying process first evolved several decades ago, with the sudden need to reduce the transport weight of food and other materials (R. P. Patel, M. P. Patel, & A. M. Suthar, 2009). Nowadays, spray drying process is extensively employed in the pharmaceutical field because of several advantages: (i) single step processing, (ii) easy to scale-up, and (iii) continuous processing operation. The functional principle of the spray drying process is based on the atomization of a liquid feed into very small droplets within a hot drying gas leading to flash drying of the droplets into solid particles (Año et al., 2011). The particles are then separated from the drying gas, using a cyclone and/or a filter bag, which yields a final spray dried product (Filipe Gaspar, 2014).

Figure 26:
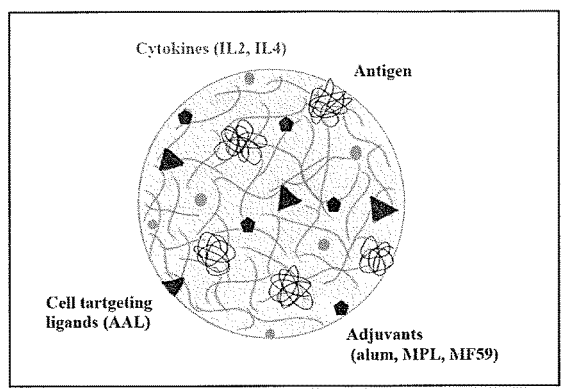
Figure 27:
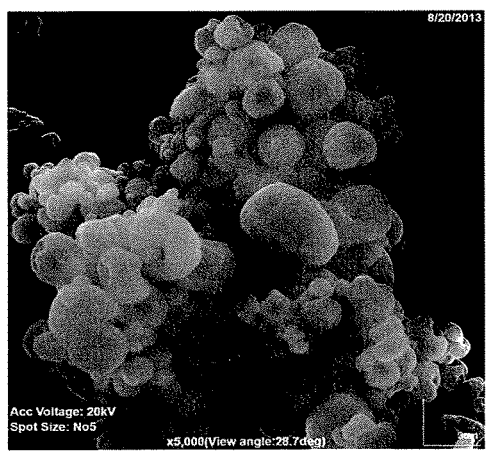
Figure 28:
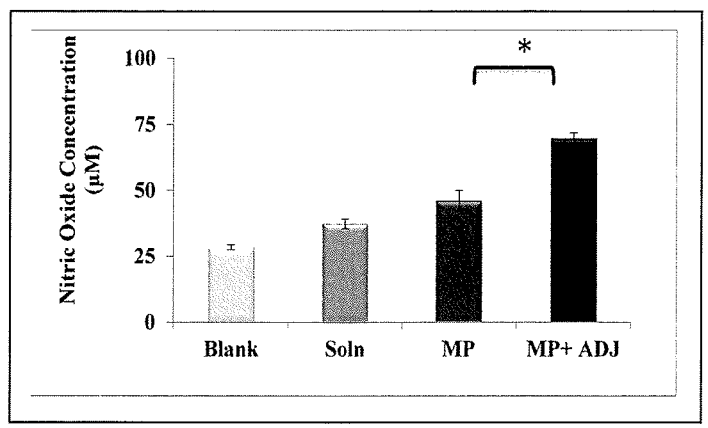
Figure 29:
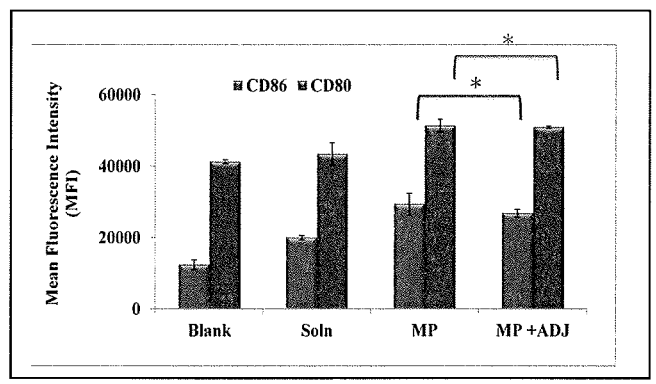
Figure 30:
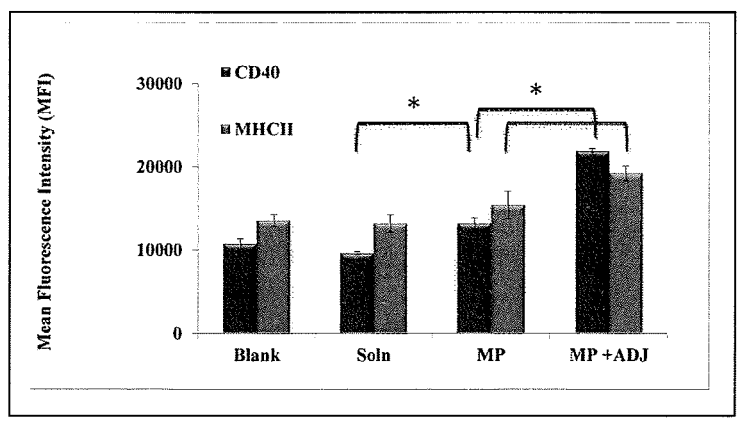
Figure 31:
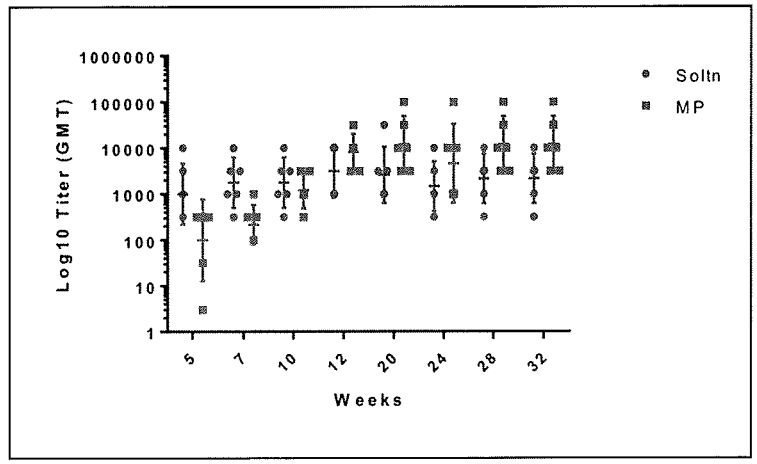
Figure 32:
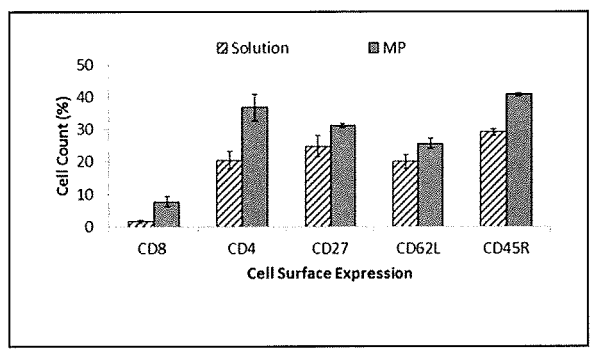
Figure 33:
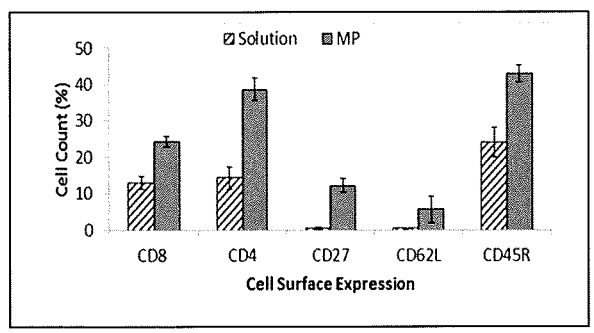

Vaccine nano/microparticles consist of a single or multiple antigens incorporated into a polymer matrix along with targeting ligands, adjuvants, and cytokines (shown as FIG. 26). Antigens can be inactivated whole cells (virus, bacteria), a part of the cells (capsid proteins, DNAs, peptides, polysaccharides) or toxoids. For examples, virus-like particles (VLPs) are made of capsid protein L1 and L2 of HPVs and are used as antigens in Gardasil® and Cervarix. Virus-like-particles (VLPs) are genetically engineered particles similar in size and structure to the virus but do not possess viral genomes, hence they lack the ability to replicate and cause infection in the host.

Polymer matrices such as poly(lactic-co-glycolic acid) (PLGA), hydroxypropyl methylcellulose (HPMC), hypromellose acetate succinate (HPMCAS), bovine serum albumin (BSA), cellulose acetate phthalate (CPD) and cyclodextrins (CDs) have been investigated as potential polymers. Selected polymers should be biodegradable and biocompatible in humans, to prevent any toxicity concerns.

Encapsulated antigens are portrayed as pathogens or foreign substances and are therefore taken up better by antigen presenting cells (APCs) and activate the innate and adaptive immune system.

Micro/nanoparticulate delivery systems that contain the antigen within a polymeric matrix, aid in the delivery of antigen/adjuvant for a prolonged period of time. Moreover, antigens delivered by a particulate carrier can enhance uptake by immune cells owing to their size, surface charge and morphology. Several publications from our lab have proved the efficacy of using microparticles for delivering cancer and infectious disease antigens.

Adjuvants have been studied and employed in vaccines for decades in order to improve, expedite, and prolong specific immune responses produced by vaccine antigens including increase in antibody responses, induction of cell mediated immunity, and reduction in dose of antigen and the number of doses required for vaccination (13). For a successful immune response to a vaccine, there are four classes of signals: (a) antigen, (b) co-stimulation of immune cells including antigen-presenting cells (APCs), (c) immune system modulation, and (d) activation of innate immune response (14) (15). Various adjuvants utilize their distinct effects via different mechanisms to stimulate the immune system, and hence it is essential to appoint appropriate adjuvants for a specific given antigen. Adjuvants can be classified into two types: delivery system and immune potentiator (16). Some adjuvants function as antigen delivery systems such as alum, calcium phosphate tyrosine liposomes, virosomes, emulsions micro/nano particles (MF59, ISCOMS), and virus-like particles, because these particulate adjuvants increase antigen stability and allow them to be presented for an extended period of time (prolonging the signal of the antigen) (17). Delivery system based adjuvants are often taken up by phagocytosis into antigen presenting cells (APCs), and they can also induce an immune response, signaling and indirectly activating APCs. Immune potentiators are purified components of bacterial cells or viruses; thus, they are recognized as "danger signals" by receptors present on immune cells (APCs) (15). Immune potentiators directly stimulate all the necessary signals for an immune response to an antigen. A major category of immune potentiators is toll-like receptor (TLR) agonists, which activate signaling pathways to trigger innate immune responses. Some examples of adjuvants that act as TLR agonists include MPL and synthetic derivatives, muramyl dipeptide and derivatives, CpG oligonucleotides, alternative bacterial or viral components (flagellin), saponins, dsRNA, and resiquimod (16). Since delivery system based adjuvants elevate the amount of antigen that reach APCs and immune potentiators mainly activate these APCs; combinations of adjuvants from both classes can be used to maximize potency of a vaccine.

Furthermore, in our study we have used adjuvants, along with the antigen which when used in combination enhance their ability to produce a robust immune response. We propose that adjuvants when combined with the microparticulate vaccine will potentiate the immune response and result in improved efficacy by generation of an antigen-specific antibody response. Moreover, adjuvants enable the vaccine to produce long-term immunity in case of re-exposure to virus.

Innovation

Conventionally, administration of influenza vaccines has utilized the intramuscular route, because this route provides long-term efficacy and safety. However, the use of needles is still somewhat feared by society. A lot of effort and time has been spent in developing alternative routes for administration of vaccines and medications. Recent discoveries have shown the skin to be an excellent source of immune cells and can be used as a strategy for vaccine administration. The transdermal route has been widely accepted due to its, non-invasive, easy-to-use, needle-free strategy and especially because of the immunocompetency of the skin. In transdermal vaccination, dendritic cells and Langerhans cells (LCs) that reside in the dermal layer of the skin have the ability to capture the antigen, migrate to the secondary lymphoid organs and present the antigen to the T cells to generate adaptive immune responses (12).

Hence, we hypothesize that transdermal delivery of the vaccine by encapsulating a viral antigen such as the HPV 16 VLP in a biodegradable matrix may not only result in better stability and uptake by Langerhans cells/dendritic cells but will also provide enhanced antigen presentation and recognition by the immune system. The innovation in our current approach lies in our proposed strategy, which is to develop, characterize and assess a micro/nanoparticulate vaccine against Influenza. Moreover, we have evaluated the interaction between the innate and adaptive immune systems by measuring co-stimulatory expression on dendritic cells exposed to the particulate vaccine with/without adjuvants. This in vitro preliminary data has prompted us to test the immune efficacy of the vaccine when delivered by the transdermal route. We hypothesize that our particulate vaccine will induce specific antibodies to neutralize the human papilloma virus and cytotoxic T lymphocytes, which will eliminate the virus, infected cells. Since our particles exist in the dry powder form, they are therefore stable under normal refrigeration conditions.

Preliminary Studies

Formulation and Characterization of HPV VLP Microparticles

The goal of this study was to determine the formulation parameters of a microparticulate vaccine for Influenza using the HPV 16 VLP. The HPV VLP was incorporated into an enteric-coated polymer matrix in this formulation. This matrix consisted of celluloseacetatephthalate (CPD) hydroxypropylmethylcellulose acetate succinate (HPMCAS), ethylcellulose (EC), trehalose and glycol chitosan polymers First, CPD dispersion (30% w/v) was diluted in deionized water with a concentration of five mg/ml under stirring. CPD and HPMCAS were dissolved separately using 1N sodium hydroxide to make final solutions at pH of 6.0 and 8.0, respectively. The mixture of CPD, HPMCAS, and EC was obtained as mentioned above, and the final solution pH was adjusted to be 7.0. Glycol chitosan was then added along with HPV 16 VLP and trehalose. In addition, Tween-20 was added to enhance the smooth surface of the microparticles (MPs). The solution was stirred at 50 rpm during the spraying process using a Buchi B290 spray dryer to maintain its homogeneity. Microparticulate adjuvants were formulated using the same procedure as the vaccine microparticles.

The microparticles (See FIG. 27) were characterized and analyzed for their morphology using the Phenom Pure Desktop® scanning electron microscopy (SEM). The average percent yield of the MPs was 90%+5.3% (w/w) after the spray drying process. The size of MPs ranged from 1.0 μm to 5.5 μm with an average size of 3.76+0.84 μm.

Evaluation of Innate Immune Response Using Murine Dendritic Cells

Sodium thioglycolate was injected into the intraperitoneal cavity of Swiss Webster (6-8 week old) to recruit the APCs (19) (20). After four days, these mice were euthanized and PBS was injected intraperitoneally into each mouse to harvest cells from the cavity. Collected cells were washed with twice. After these APCs adhered to the bottom of a flask and the supernatant was removed and complete RPMI media was added in the presence of ConA. The harvested APCs (5×104 cells/well) were seeded in Dulbecco's complete media in a 96 well plate. The soluble and particulate vaccines (with and without adjuvants) were introduced to the APCs with the same amount of antigen and adjuvant. The induced APCs were incubated for 20 hours at 37° C. with 5% CO2. Supernatants were collected and the amount of nitric oxide released in each group was analyzed using the Greiss chemical method. The plate was read at a wavelength of 540 nm (21). The nitric oxide assay was performed to investigate the recognition of vaccine and adjuvants by the APCs (22). Nitric oxide (NO) is released in the process of conversion of arginine to citrulline by nitric oxide synthase during the recognition and phagocytosis of antigen from APCs (23). A higher level of NO released indicates a stronger activation of APCs by the vaccines. FIG. 28 is a graph of nitric oxide concentration of various solutions.

Assessment of adaptive immune response by observing the cell surface expression on dendritic cells exposed to the microparticulate vaccine formulation with adjuvants Similarly to the innate immunity, after stimulating the antigen with APCs for 20 hours, the supernatant was removed to perform the nitric oxide assay. These cells were gently washed with PBS. Trypsin-EDTA solution was used to collect the APCs and Hank's Balanced Salt Solution (HBSS) was used to wash prior to an incubation with antimouse-CD80 PE, antimouse-CD86 FITC, antimouse-CD40 PE, antimouse-MHC II (FITC). After 1-hour incubation, the cells were washed twice with HBSS, then analyzed for the specific cell surfaced markers using BD Accuri® C6 flow cytometer.

Different markers can be used to evaluate the antigen presentation on APCs in ex-vivo or in-vitro studies. Some of these markers include CD40, MHC class II, CD80, and CD86. Both expressions of CD40 and MHC II on the surface of APCs are necessary for a successful stimulation of T cells from APCs as demonstrated in FIGS. 29 and 30 (18). In this study, the particulate vaccine enhanced both MHC II and CD40 expressions ($p<0.001$), compared to the soluble vaccine. Except P4 and flagellin, all other adjuvants enhanced highly MHC II expression ($p<0.001$) on the cell surface, compared to the M2p MP group. The highest CD40 expressions were was found in the presence of R848 and P4 ($p<0.001$), followed by CT and MPL ($p<0.01$). Flagellin did not enhance either CD40 or MHC II expression.

CD80 and CD86 molecules are normally expressed on activated APCs and provide critical co-stimulatory signals for T cell activation and survival (19). In FIGS. 31 and 32, the microparticulate vaccine enhanced the CD80 expression but not the CD86 expression, compared to these expressions of the soluble vaccine group. Except CpG and flagellin, all other adjuvants induced statistically ($p<0.001$) the CD80 expression. R848 and CpG enhanced the highest ($p<0.001$) expression of CD86, followed by alum and P4 treated groups, compared to the vaccine MP treated group.

The human papilloma virus type 16 virus-like particles (HPV 16 VLP) was provided by the Center for Disease Control and Prevention (CDC). The HPV 16 VLP was incorporated into a cellulose polymer mix of cellulose acetate phthalate (Aquacoat® CPD), HPMCAS and ethyl cellulose (Aquacoat® ECD). Other constituents included trehalose, chitosan, tween 20 and, lastly, the HPV 16 VLP. This suspension was spray dried using the B-290 spray dryer to obtain particulates.

Mice were immunized transdermally using dissolving microneedles. Dissolving microneedles, intended for the painless transdermal release of encapsulated pharmaceutical agents after dermal insertion, were developed as a solution to the safety issue. Dissolvable microneedles mainly deploy PDMS micromolds which are made from a master structure of microneedles as illustrated below. Briefly, Polydimethylsiloxane (PDMS) was poured onto the stainless steel master structure obtained from Micropoint Technologies INC, Singapore. The HPV 16 VLP formulation was then spray dried respectively. The microneedle formulation included 10% of M2e VLP, 25% trehalose, 25% maltose, 20% polyvinyl alcohol and 20% hydroxypropylmethylcellulose (HPMC). The formulation was prepared beginning with the addition of PVA, HPMC, Maltose and Trehalose to a microcentrifuge tube, followed by the addition of Ammonium hydroxide ($NH_4OH$) to the microcentrifuge tube. Once dissolved, this formulation was then added to a microneedle mold avoiding air bubbles. These molds were then placed straight into 50 mL centrifuge tubes. Centrifugation was done in a fixed angle centrifuge in order to remove air bubbles and to force the formulation into the microneedles mold. The maximum speed was 2000 rpm, which was achieved step wise in order to avoid jerking in the rotation process, time for which centrifugation should be done was 5-10 min. After this centrifugation step, the backing layer was added and centrifuged repeatedly in the same manner. The molds were placed in tubes and then in an incubator at 37 degrees C. overnight.

For animal experiments, 4-6 week old female Balb/c mice were immunized, with 3 doses, 1 prime dose and 2 booster doses at 4-week intervals. For determination of long-term efficacy of the vaccine, the mice antibody responses were monitored for a 40-week period, followed by which they were sacrificed for further analysis. The groups for the study are shown in Table 5.

TABLE 5

Treatment groups receiving HPV 16 VLP Vaccines

| Group Name | Treatment | Route | Dose (μg) | # of Doses |
|---|---|---|---|---|
| Solution Vaccine | HPV 16 VLP | Transdermal | 20 (Prime)<br>10 (Booster) | 3 |
| Microparticulate Vaccine | HPV 16 VLP | Transdermal | 20 (Prime)<br>10 (Booster) | 3 |

All animal experiments were approved by Mercer University IACUC review board and conducted under the guidelines of Mercer University IACUC.

Blood samples were collected before immunization and beginning at week 5. Samples were stored in −20° C. until analysis. Specific serum antibody for HPV 16 was assessed using ELISA. Plates were coated with 100 μg/well of HPV VLPs. Serum samples were used for detection of primary antibody and alkaline phosphatase (AP) conjugated goat anti-mouse IgG was used as secondary antibody to determine total amount of antibody. The alkaline phosphatase substrate was used for detection of color. The optical density was taken at 405 nm on the Biotek Synergy ELISA plate reader.

After the animals are sacrificed, the primary and secondary lymphoid organs were extracted (i.e. spleen and lymph node) and made into single cell suspensions. The single cell suspensions were stained with fluorescence conjugated antibodies specific to T cell phenotypes, helper T cells (CD4+) and cytotoxic T cells (CD8+) and memory B and T cell phenotypes, memory T cells (CD45R and CD62L) and memory B cell (CD27) quantified using flow cytometry.

EXAMPLE 4 REFERENCES

1. Centers for Disease Control and Prevention. Seasonal Influenza (Flu) [Internet]. 2014. Available from: cdc.gov/flu/about/disease
2. Akalkotkar, A., Tawde, S. A., Chablani, L., & D'Souza, M. J. (2012). Oral delivery of particulate prostate cancer vaccine: in vitro and in vivo evaluation. *Journal of Drug Targeting,* 20(4), 338-346.
3. Bhowmik, T., D'Souza, B., Shashidharamurthy, R., Oettinger, C., Selvaraj, P., & D'Souza, M. J. (2011). A novel microparticulate vaccine for melanoma cancer using transdermal delivery. *Journal of Microencapsulation,* 28(4), 294-300.
4. Chablani, L., Tawde, S. A., Akalkotkar, A., D'Souza, C., Selvaraj, P., & D'Souza, M. J. (2012). Formulation and evaluation of a particulate oral breast cancer vaccine. *Journal of Pharmaceutical Sciences,* 101(10), 3661-3671.
5. Shastri, P. N., Kim, M.-C., Quan, F.-S., D'Souza, M. J., & Kang, S.-M. (2012). Immunogenicity and protection of oral influenza vaccines formulated into microparticles. *Journal of Pharmaceutical Sciences,* 101(10), 3623-3635.
6. Li, N., Peng, L.-H., Chen, X., Nakagawa, S., & Gao, J.-Q. (2011). Transcutaneous vaccines: novel advances in technology and delivery for overcoming the barriers. *Vaccine,* 29(37), 6179-6190.
7. Smith D M, Simon J K, Baker J R. Applications of nanotechnology for immunology. Nat Rev Immunol. 2013 August; 13(8):592-605.
8. Maisonneuve C, Bertholet S, Philpott D J, De Gregorio E. Unleashing the potential of NOD- and Toll-like agonists as vaccine adjuvants. Proc Natl Acad Sci USA. 2014 Aug. 26; 111(34):12294-9.
9. Derek T O'Hagan. New Generation Vaccine Adjuvants [Internet]. Novartis Vaccines and Diagnostics; Available from: roitt.com/elspdf/Newgen_Vaccines.pdf
10. Mohan T, Verma P, Rao D N. Novel adjuvants & delivery vehicles for vaccines development: a road ahead. Indian J Med Res. 2013 November; 138(5):779-95.
11. Gupta R K, Siber G R. Adjuvants for human vaccines—current status, problems and future prospects. Vaccine. 1995 October; 13(14):1263-76.
12. Batista-Duharte A, Lindblad E B, Oviedo-Orta E. Progress in understanding adjuvant immunotoxicity mechanisms. Toxicol Lett. 2011 Jun. 10; 203(2):97-105.
13. Cohn Z A. Activation of mononuclear phagocytes: fact, fancy, and future. J Immunol Baltim Md. 1950. 1978 September; 121(3):813-6.
14. Lagasse E, Weissman I L. Flow cytometric identification of murine neutrophils and monocytes. J Immunol Methods. 1996 Oct. 16; 197(1-2):139-50.
15. Zughaier S M, Tzeng Y-L, Zimmer S M, Datta A, Carlson R W, Stephens D S. *Neisseria meningitidis* lipooligosaccharide structure-dependent activation of the macrophage CD14/Toll-like receptor 4 pathway. Infect Immun. 2004 January; 72(1):371-80.
16. Roper R L. Antigen presentation assays to investigate uncharacterized immunoregulatory genes. Methods Mol Biol Clifton N.J. 2012; 890:259-71.
17. Kohchi C, Inagawa H, Nishizawa T, Soma G-I. ROS and innate immunity. Anticancer Res. 2009 March; 29(3):817-21.

Example 5

Formulation and Testing of a Microneedle-Based Particulate Vaccine for Rsv

Background

Respiratory Syncytial Virus (RSV) is the leading cause of bronchiolitis in infants and immunocompromised adults. It is estimated that approximately 3.4 million children are annually hospitalized due to RSV-related illnesses and 160, 000 people die from RSV infection worldwide (Nair et al., 2010). The past few decades have been spent in developing a promising strategy to combat the virus either using subunit vaccines, attenuated viruses or live vector vaccines. With the centralized controversy surrounding the disease i.e., the tragic outcome of vaccinated children who developed vaccine-enhanced respiratory disease, in the 1960s with alum-adjuvanted, formalin inactivated RSV; there still remains a large barrier before the licensure of an RSV vaccine (H. W. Kim et al., 1969). RSV has 10 genes that encode 11 proteins. Among them are the F, fusion protein and G, glycoprotein which are important antigenic proteins expressed on the surface of the virus and a target for neutralizing antibodies that facilitate a protective immune response in the patient (Murawski et al., 2010).

There are multiple subunit licensed vaccines that use specific proteins that have similarities to the native form of the virus, one of which are VLPs. Virus-like-particles (VLPs) are genetically engineered particles similar in size and structure to the virus but do not possess viral genomes, hence they lack the ability to replicate and cause infection in the host. Recombinant baculovirus-expressed VLPs containing RSV-F and/or G glycoproteins, were shown to stimulate antigen-specific antibody responses and defend against RSV infection in murine models (K.-H. Kim et al., 2015; Murawski et al., 2010; Quan et al., 2011). Encapsulated antigens are portrayed as pathogens or foreign substances and are therefore taken up better by antigen presenting cells (APCs) and activate the innate and adaptive immune system. Micro/nanoparticulate delivery systems that contain the antigen within a polymeric matrix, aid in the delivery of antigen/adjuvant for a prolonged period of time. Several publications from our lab have proved the efficacy of using microparticles for delivering cancer and infectious disease antigens through the oral, transdermal and subcutaneous routes. (Akalkotkar, Tawde, Chablani, & D'Souza, 2012; Bhowmik et al., 2011; Chablani et al., 2012; Shastri, Kim, Quan, D'Souza, & Kang, 2012). Our approach is to incorporate RSV Fusion protein VLPs in a mix of biodegradable polymers and spray dry the formulation to obtain microparticles.

Conventionally, administration of vaccines has utilized the intramuscular route, because this route provides long term efficacy and safety. However, the use of needles is still somewhat feared by society. A lot of effort and time has been spent in developing alternative routes for administration of vaccines and medications. Recent discoveries have shown the skin to be an excellent source of immune cells and can be used as a strategy for vaccine administration. The transdermal route has been widely accepted due to its, non-invasive, easy-to-use, needle-free strategy and especially because of the immunocompetency of the skin. In transdermal vaccination, dendritic cells and Langerhans cells (LCs) that reside in the dermal layer of the skin have the ability to capture the antigen, migrate to the secondary lymphoid organs and present the antigen to the T cells to generate adaptive immune responses (Li, Peng, Chen, Nakagawa, & Gao, 2011). Hence, we hypothesize that transdermal delivery of the vaccine by encapsulating a viral antigen such as the fusion protein from the surface of the RSV virus in a biodegradable matrix may not only result in better uptake but will also provide enhanced antigen presentation and recognition by the immune system.

Adjuvants are crucial compounds used in combination with vaccine antigens to enhance their ability to produce a stronger immune response. They are minimally toxic and have no long lasting immune effects when given alone. Specific aims 1 and 2 have used adjuvants with vaccine to potentiate the immune response against the disease. Alum, an adjuvant delivery system has been widely used in human vaccines for decades. The hypothesized mechanisms of Alum include enhanced antigen uptake by APCs, improved MHC II expression and antigen presentation (Dubensky & Reed, 2010). Monophosphoryl lipid A (MPL®) is a Toll-like receptor-4 agonist that induces a strong cellular (T cell mediated) immune response. Another approved adjuvant, MF59™ is a squalene in water nano-emulsion that shows cell-mediated/antibody responses and results in secretion of cytokines and chemokines by DCs and macrophages. Pneumococcal surface adhesion A-derived peptide (P4) has been recently explored as an adjuvant since it has shown enhanced opsonophagocytosis in some studies (Rajam, Anderton, Carlone, Sampson, & Ades, 2008). R848 is an imidazoquinoline compound that activates immune cells via the TLR7/8 pathway.

Innovation

Currently there is no safe and efficacious treatment regimen to treat infections caused by RSV. Drugs such as corticosteroids, antibiotics and bronchodilators are primarily administered to alleviate the symptoms in complicated cases. Ribavirin, an antiviral drug has been approved for treatment of RSV infections. In high-risk infants a novel approved monoclonal antibody; palivizumab (Synagis®) is approved to prevent sever lower respiratory tract infections and has markedly reduced risk of hospitalization. However, the high cost of therapy along with no long term memory response to protect against future RSV infections, necessitates a need for a safe and potent vaccine.

The innovation in our current approach lies in our proposed strategy which is to develop, characterize and assess a micro/nanoparticulate vaccine against RSV, which has no licensed vaccine till date. Moreover, we have evaluated the interaction between the innate and adaptive immune systems by measuring co-stimulatory expression on dendritic cells exposed to the particulate vaccine with/without adjuvants. This in vitro preliminary data has prompted us to test the immune efficacy of the vaccine when delivered by the transdermal route.

We hypothesize that our particulate vaccine will induce specific antibodies to neutralize RSV and cytotoxic T lymphocytes which will eliminate the virus infected cells. Since our particles exist in the dry powder form, they are therefore stable under normal refrigeration conditions (recent unpublished data).

Preliminary Studies

Formulation and Characterization of RSV-F VLP Microparticles

Figure 34:
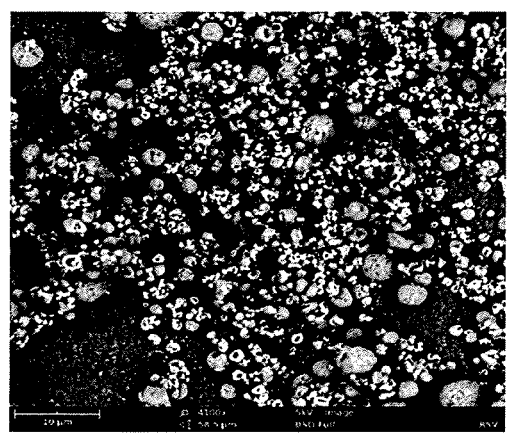

The goal of this study was to determine the formulation parameters of a microparticulate vaccine for RSV using F Fusion protein virus-like particles (VLPs). A unique blend of cellulose polymers and chitosan was utilized to formulate microparticles. Briefly 0.5% (w/w) F-VLP solution was incorporated into a mixture of cellulose acetate phthalate, hydroxypropylmethylcellulose acetate succinate (HPM-CAS), ethylcellulose, trehalose and chitosan polymers. The aqueous suspension was subsequently spray-dried using the Buchi-290 spray dryer to obtain micro/nanoparticles. The microparticles were characterized and analyzed for their size, surface charge, encapsulation efficiency and antigen stability. The Malvern Zetasizer® Nano ZS was used to carry out size and surface potential measurements. Particles were suspended in citric acid (10 mM, pH 3.8) for 10 minutes and centrifuged. The particles were resuspended in deionized water and later analyzed by the instrument. The microparticle images were captured on carbon sheets and observed under 20 kV at 7500× using the scanning electron microscope (See FIG. 34).

Table 6 summarizes the physicochemical characteristics of the spray dried microparticles.

TABLE 6

Characterization of Vaccine Microparticles

| Product Yield | 88-93% |
|---|---|
| Particle Size | 1-2 μm |
| Surface Charge | 25 ± 2 mV |
| Protein Content | 80-85% |

Figure 35:
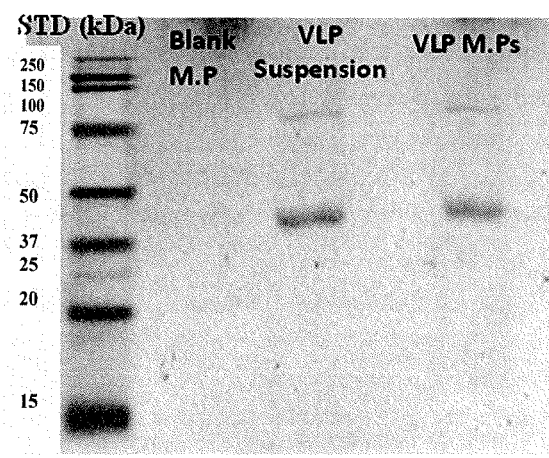

To evaluate antigen integrity, SDS PAGE was performed for the VLP microparticulate formulation as seen in FIG. 35. The spray dried microparticles were added to PBS, vortexed for 10 minutes followed by incubation at 37° C. for 10 minutes to extract the antigen from the matrix to check antigen integrity and encapsulation efficiency. Ten micrograms equivalent of F-VLP was loaded onto the acrylamide gel. Precision protein plus standards were run as a control. We found that the F-VLP remained intact after spray drying when compared to the F-VLP suspension lane.

Evaluate Immunogenicity of Vaccine Microparticles Using Murine Dendritic Cells

After characterization, we tested the in vitro immunogenicity of the RSV F-VLP microparticles using a dendritic cell line, DC 2.4. Dendritic cells are responsible for pathogen recognition and eradication by releasing cytokines such as TNF-α, nitric oxide (NO) and IFN-γ. The increase in levels of nitrite may be related to enhanced antigen recognition and delivery to dendritic cells. NO is also known to eradicate viruses by nitrosation of cysteine residues within key proteins required for replication purposes (Wink et al., 2011).

Figure 36:
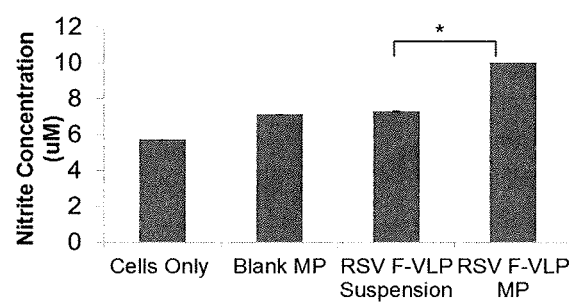
Figure 37:
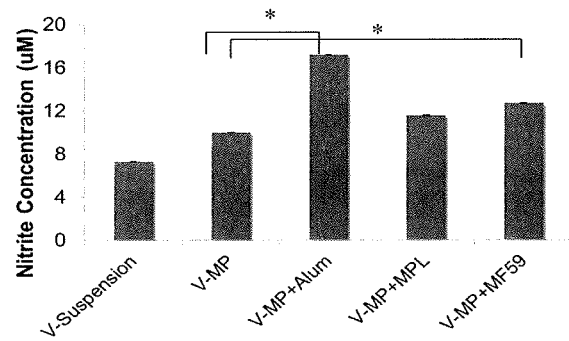

The microparticles' ability to generate an innate immune response was evaluated using the nitric oxide assay. Cells were plated in 24 well plates following which blank MPs, RSV F-VLP suspension and vaccine MPs were added and incubated with the cells for 20 hrs. The VLP-MPs were compared with controls of blank MPs and VLP solution. Subsequently, the cell supernatant was analyzed for nitric oxide (NO) levels (Ubale, D'Souza, Infield, McCarty, & Zughaier, 2013) using the Griess Test. The results proved that the F-VLP microparticles were immunogenic, by activating the innate immune system. FIG. 36 shows the amount of nitric oxide released (μM) from DC 2.4 cells when exposed to Cells Only, Blank MP, RSV F-VLP Suspension, RSV F-VLP MP (*p<0.05). There was a significant release of nitric oxide seen in supernatant of cells receiving RSV F-VLP MPs. FIG. 37 shows Amount of nitric oxide released from DC 2.4 cells when exposed to VLP Suspension, RSV VLP MP and RSV VLP MP+Alum, MPL A and MF59 (*p<0.05) There was a significant release of nitric oxide seen in supernatant of cells receiving RSV F-VLP+Alum/MF59 MPs.

Figure 38:
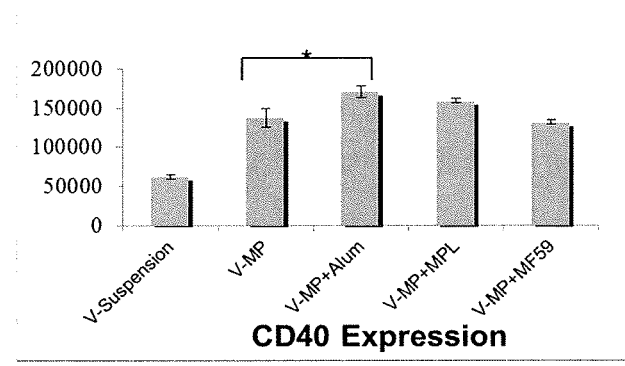
Figure 39:
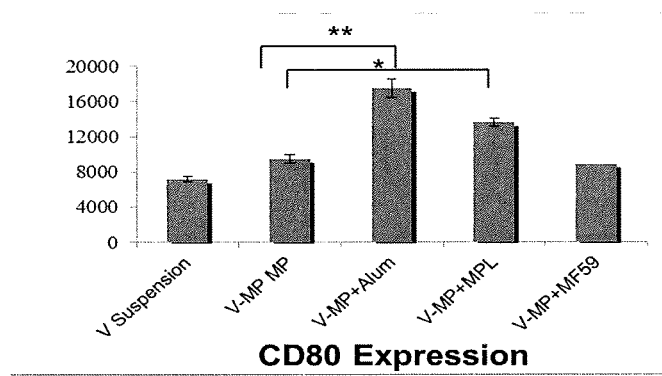
Figure 40:
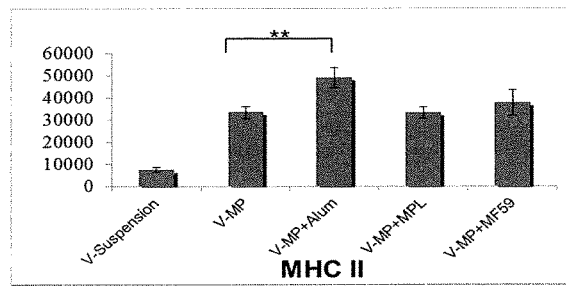

Since the RSV F-VLP microparticles demonstrated immunogenicity, we were interested to understand the interaction between the innate and adaptive immune responses. Vaccines are required to be efficiently taken up and processed by dendritic cells and presented on major histocompatibility complex I or II molecules along with co-stimulatory molecule expression such as CD40 and CD80/86 that are required for T and B cell activation and survival, which are critical for an adaptive and hence a memory response after vaccination. Following the nitric oxide assay we further examined the surface co-stimulatory expression on dendritic cells treated with RSV F-VLP microparticles alone and with adjuvants, which are substances that enhance the antigen specific response. Briefly, the cells were washed with PBS and detached using Trypsin EDTA. Each group of cells was analyzed separately for different markers (CD40, CD80, CD86, MHCI and MHC II) using the flow cytometer. Theoretically, dendritic cells will engulf antigen and adjuvant and process it in the phagolysosome. The protein fragments will be expressed on MHC II surface molecules. For the activation of the CD4+ T cell, a co-stimulatory molecule known as CD40 is required. CD40 and MHC II expression were significantly higher in the VLP-MP+Alum group compared to VLP solution. The inclusion of adjuvant increased CD40 expression and antigen presentation on MHCII molecules. FIG. 38 is a graph showing the expression of CD40 on DC 2.4 cells exposed to Blank MP, F-VLP solution, F-VLP MP and VLP MP with adjuvant. MHC II expression was significantly higher in MP group compared to VLP solution. CD40 expression was higher in V+Alum group, compared to F-VLP MP group (*p<0.05). Adjuvants resulted in higher CD40 costimulatory expression. FIG. 39 is a graph showing the expression of CD80 on DC 2.4 cells exposed to Blank MPs, F-VLP solution, F-VLP MP and VLP MP with adjuvants. CD80 is a co-stimulatory molecule required for activation of CD8 T cells. CD80 expression was significantly higher in V MP+Alum (**p<0.01)/MPL A (*p<0.05) group compared to RSV F-VLP MP alone. MF59 did not result in enhanced expression of CD80 molecules. FIG. 40 is a graph showing the expression of CD40 on DC 2.4 cells exposed to Blank MP, F-VLP solution, F-VLP MP and VLP MP with adjuvant. MHC II is a protein that expresses fragments of antigen to T cells of the immune system. MHC II expression was significantly higher in MP group compared to VLP solution. CD40 expression was higher in V+Alum group, compared to RSV F-VLP MP group (**p<0.01). Adjuvants resulted in higher CD40 costimulatory expression.

The particles collected were weighed and samples were characterized for size, surface charge and morphology. The Malvern Zetasizer® Nano ZS was used to carry out size and surface potential measurements. Particles were suspended in citric acid for 10 minutes and centrifuged. The particles were re-suspended in deionized water and later analyzed by the instrument. The microparticle images were captured on carbon tape and observed under 20 kV at 7500× using the Phenom® Desktop SEM. The spray-dried microparticles were added to PBS, vortexed for 10 minutes followed by incubation at 37° C. to extract the protein antigens from the matrix. The sample was centrifuged and supernatant was subjected to the micro BCA protein assay to quantify the amount of protein incorporated in microparticles. The vaccine MPs demonstrated immunogenic properties when compared with its solution counterpart, as seen in FIG. 37. We further evaluated the surface marker expression on dendritic cells using the flow cytometer. The vaccine MPs+adjuvants were incubated with dendritic cells and incubated for 20 hrs. The cell supernatant was analyzed for nitric oxide followed by CD40, CD80, CD86, MHC I and CD54 expression which was examined using the flow cytometer. The adjuvants significantly increased nitric oxide and surface marker expression of MHC I and CD80 as seen in FIGS. 37-39. Hence, adjuvants may be effective in potentiating the immune response.

In Vivo Efficacy of Vaccine Post-Challenge with Live RSV A2 Virus

To evaluate the effectiveness of the F-VLP microparticulate vaccine, mice were dosed using dissolving microneedles. Dissolving microneedles, intended for the painless transdermal release of encapsulated pharmaceutical agents after dermal insertion, were developed as a solution to the safety issue. Dissolvable microneedles mainly deploy PDMS micromolds which are made from a master structure of microneedles (FIG. 5). Briefly, Polydimethylsiloxane (PDMS) was poured onto the stainless steel master structure obtained from Micropoint Technologies INC, Singapore (Step 1-3; FIG. 5). The microneedles were made using 10% w/w microparticles, 25% w/w trehalose, 25% w/w maltose, 20% w/w polyvinylalcohol (PVA), 20% w/w hydroxypropylmethyl cellulose (HPMC). PVA, HPMC, Maltose and Trehalose to a 1.7 mL microcentrifuge tube. The contents were dissolved in minimum possible amount of water (e.g. 200 mg of total solid content can be dissolved in 600 uL water) and vortexed. Then approximately ⅕th quantity (of water that was added to dissolve the solids) of Ammonium hydroxide (NH4OH) was added to the microcentrifuge tube (here, 120 uL) and vortexed again. The tube was kept aside for some time and observed if the contents are dissolved. If everything goes into the solution, add the weighed amount of vaccine microparticles in the end. This formulation is then added to mold avoiding air bubbles. These molds are then placed straight in 50 mL centrifuge tubes. Centrifugation is done in the fixed angle centrifuge in order to remove air bubbles and to force the formulation to go into the microneedles mold. The maximum speed is 2000 rpm which is achieved step wise, in order to avoid jerk in the rotation process, time for which centrifugation should be done is 5-10 min. Speed should be lowered gradually for same reason as above. After this centrifugation step, more formulation was added to molds and centrifugation is repeated in the same manner (Step 3-6; FIG. 5). This step can be repeated further by adding more formulation or blank backing layer solution. The molds were placed in tubes and placed in an incubator at 37.0 overnight (Step 7-9; FIG. 5).

The groups for the study and doses that were administered to each group are shown in Table 7.

TABLE 7

Groups for animal study

| Serial No. | Groups | VLP/dose | Challenge |
|---|---|---|---|
| 1 | PBS (−) Control | — | RSV-A2 |
| 2 | IM FI-RSV (formalin inactivated RSV) | 1.0 ug FI-RSV | RSV-A2 |
| 3 | Transdermal Suspension (Vaccine + MPL) | 5.0 ug RSV F VLP | RSV-A2 |
| 4 | Transdermal (MP Vaccine) | 5.0 ug RSV F VLP | RSV-A2 |
| 5 | Transdermal (MP Vaccine + MPL ®) | 5.0 ug RSV F VLP | RSV-A2 |

For the study, 4-6 week old, male C57BL/6 mice were immunized with 1 prime and 2 booster doses of microparticulate RSV F-VLP via the transdermal route by treating the mice using dissolving microneedles. Blood samples were collected every week and serum antibody (IgG) levels were analyzed by ELISA. Subsequently, the mice were challenged with live RSV-A2 virus and body weight was measured for a period of 5 days. At the end of the 5th day, all mice were sacrificed and effector T cell populations, specifically, CD4+ and CD8+ T cells were quantified in the lymph node and spleen using fluorescence activated cell sorting (FACS). The lungs were harvested and utilized for histopathology staining and lung viral titer experiments. The lung viral load in the test groups helped us understand whether the vaccination protocol was effective in generating an immune response against the RSV infection.

Figure 41:
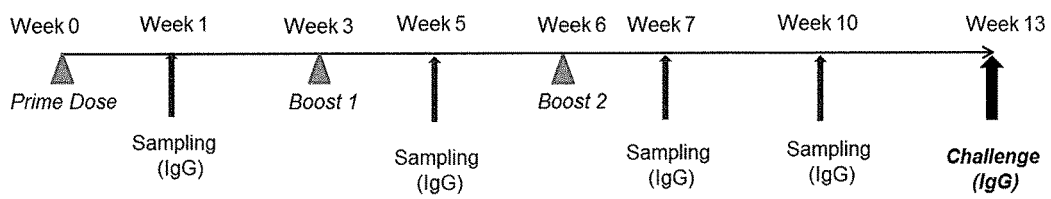

Experimental Schedule:

FIG. 41 is a timeline for the animal study, with dosing and sampling intervals incorporated.

Figure 42:
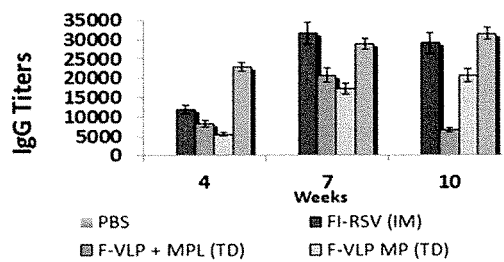
Figure 43:
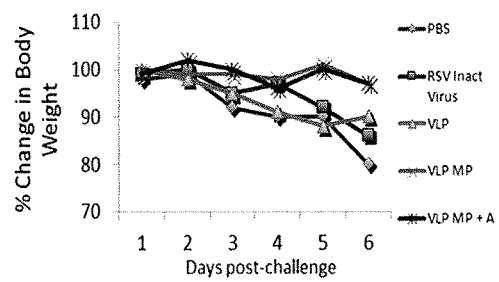
Figure 44:
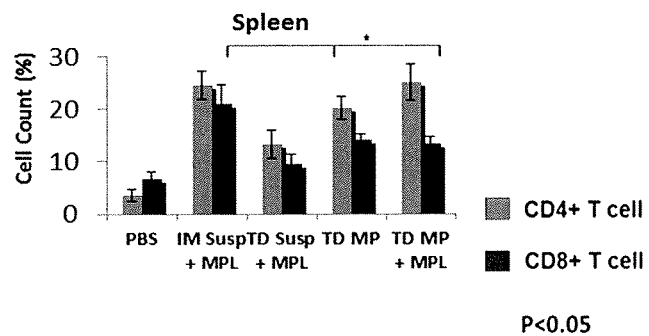
Figure 45:
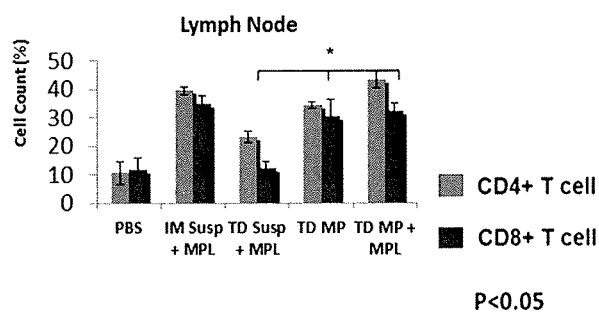
Figure 46:
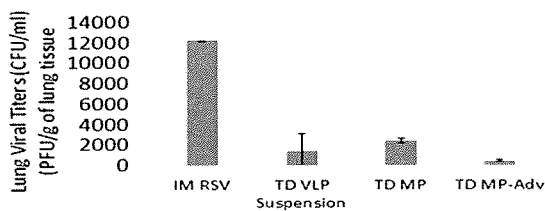

FIG. 42 is a graph showing IgG antibody levels in blood serum of mice inoculated with Inactivated RSV vaccine (FI-RSV), solution form of F-VLP, F-VLP microparticles and F-VLP+MPL microparticles. FIG. 43 is a graph showing body weight measurements of mice 6 days post-challenge with live RSV A2 virus. Untreated mice (PBS) showed the highest change in weight compared to vaccinated mice. FIG. 44 and FIG. 45 show graphs of CD4+ and CD8+ T cell response after challenge with live RSV A2 virus. TD MP+MPL showed higher CD4 and CD8 T cell populations compared to TD MP and TD Suspension+MPL. FIG. 46 is a graph of viral titers measured in lung homogenates of various groups after challenge using RT-PCR. Lung viral titers were found to be significantly higher in mice vaccinated with inactivated RSV given IM, VLP suspension and VLP microparticles given transdermally compared with VLP MP+MPL A.

EXAMPLE 5 REFERENCES

1. Akalkotkar, A., Tawde, S. A., Chablani, L., & D'Souza, M. J. (2012). Oral delivery of particulate prostate cancer vaccine: in vitro and in vivo evaluation. *Journal of Drug Targeting*, 20(4), 338-346.
2. Bhowmik, T., D'Souza, B., Shashidharamurthy, R., Oettinger, C., Selvaraj, P., & D'Souza, M. J. (2011). A novel microparticulate vaccine for melanoma cancer using transdermal delivery. *Journal of Microencapsulation*, 28(4), 294-300.
3. Chablani, L., Tawde, S. A., Akalkotkar, A., D'Souza, C., Selvaraj, P., & D'Souza, M. J. (2012). Formulation and evaluation of a particulate oral breast cancer vaccine. *Journal of Pharmaceutical Sciences*, 101(10), 3661-3671.
4. D'Souza, B., Bhowmik, T., Shashidharamurthy, R., Oettinger, C., Selvaraj, P., & D'Souza, M. (2012). Oral microparticulate vaccine for melanoma using M-cell targeting. *Journal of Drug Targeting*, 20(2), 166-173.
5. Dubensky, T. W., & Reed, S. G. (2010). Adjuvants for cancer vaccines. *Seminars in Immunology*, 22(3), 155-161.
6. Kim, H. W., Canchola, J. G., Brandt, C. D., Pyles, G., Chanock, R. M., Jensen, K., & Parrott, R. H. (1969). Respiratory syncytial virus disease in infants despite prior administration of antigenic inactivated vaccine. *American Journal of Epidemiology*, 89(4), 422-434.
7. Kim, K.-H., Lee, Y.-T., Hwang, H. S., Kwon, Y.-M., Kim, M.-C., Ko, E.-J., . . . Kang, S.-M. (2015). Virus-like particle vaccine containing the F protein of respiratory syncytial virus confers protection without pulmonary disease by modulating specific subsets of dendritic cells and effector T cells. *Journal of Virology*, JVI.02018-15.
8. Li, N., Peng, L.-H., Chen, X., Nakagawa, S., & Gao, J.-Q. (2011). Transcutaneous vaccines: novel advances in technology and delivery for overcoming the barriers. *Vaccine*, 29(37), 6179-6190. h
9. Murawski, M. R., McGinnes, L. W., Finberg, R. W., Kurt-Jones, E. A., Massare, M. J., Smith, G., Morrison, T.

G. (2010). Newcastle Disease Virus-Like Particles Containing Respiratory Syncytial Virus G Protein Induced Protection in BALB/c Mice, with No Evidence of Immunopathology. *Journal of Virology*, 84(2), 1110-1123.
10. Nair, H., Nokes, D. J., Gessner, B. D., Dherani, M., Madhi, S. A., Singleton, R. J., Campbell, H. (2010). Global burden of acute lower respiratory infections due to respiratory syncytial virus in young children: a systematic review and meta-analysis. *Lancet* (London, England), 375(9725), 1545-1555.
11. Quan, F.-S., Kim, Y., Lee, S., Yi, H., Kang, S.-M., Bozja, J., Compans, R. W. (2011). Viruslike particle vaccine induces protection against respiratory syncytial virus infection in mice. *The Journal of Infectious Diseases*, 204(7), 987-995.
12. Rajam, G., Anderton, J. M., Carlone, G. M., Sampson, J. S., & Ades, E. W. (2008). Pneumococcal surface adhesin A (PsaA): a review. *Critical Reviews in Microbiology*, 34(3-4), 131-142.
13. Shastri, P. N., Kim, M.-C., Quan, F.-S., D'Souza, M. J., & Kang, S.-M. (2012). Immunogenicity and protection of oral influenza vaccines formulated into microparticles. *Journal of Pharmaceutical Sciences*, 101(10), 3623-3635.
14. Ubale, R. V., D'Souza, M. J., Infield, D. T., McCarty, N. A., & Zughaier, S. M. (2013). Formulation of meningococcal capsular polysaccharide vaccine-loaded microparticles with robust innate immune recognition. *Journal of Microencapsulation*, 30(1), 28-41.
15. Wink, D. A., Hines, H. B., Cheng, R. Y. S., Switzer, C. H., Flores-Santana, W., Vitek, M. P., Colton, C. A. (2011). Nitric oxide and redox mechanisms in the immune response. *Journal of Leukocyte Biology*, 89(6), 873-891.

Example 6

Encapsulation of Pancreatic Beta Cells for the Treatment of Insulin Dependent Diabetes Mellitus Purpose This research evaluates the fabrication of microtissue encapsulating pancreatic islet beta cells (Beta-TC-6) in alginate microcapsules coated with chitosan, as therapy for type I diabetes mellitus. The biocompatibility and semipermeable nature of these alginate polymers, in addition to their ability to provide immune protection and their high mechanical properties appears to be a promising strategy for cell encapsulation. In this study, encapsulated cells were evaluated for cell viability, secretion of insulin in the presence of glucose.

Introduction

Figure 47:
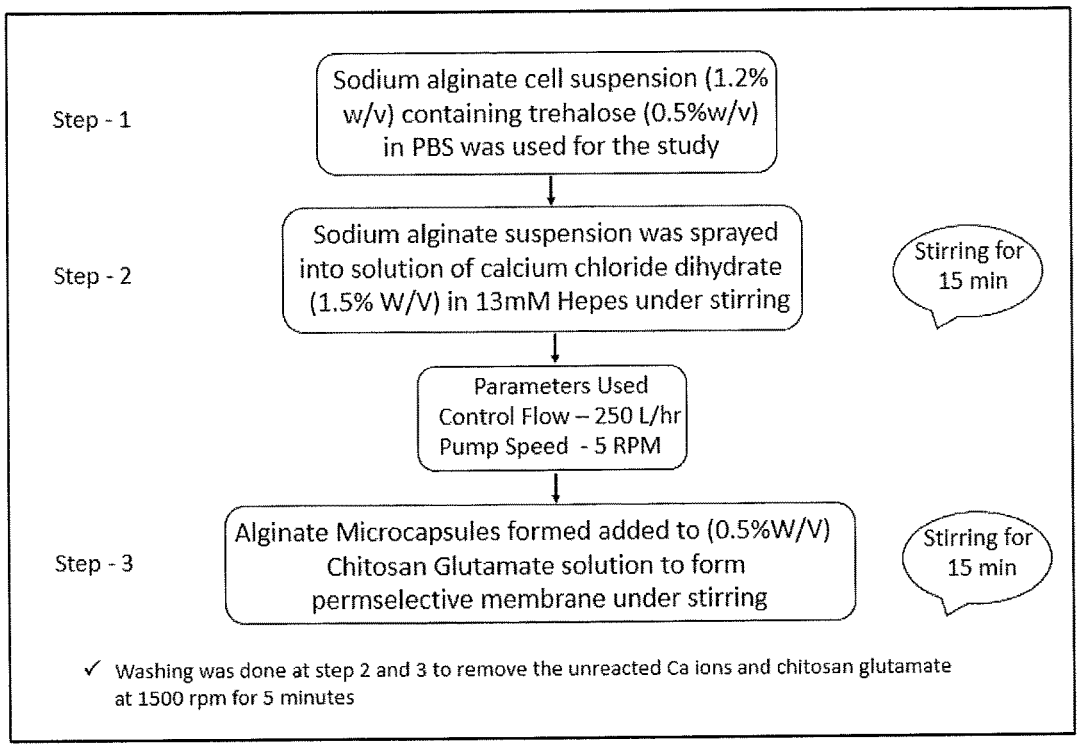
FIG. 47 is a schematic flow diagram of one exemplary embodiment of a method used for the preparation of microcapsules encapsulating live pancreatic beta cells using biocompatible polymer.
Figure 48:
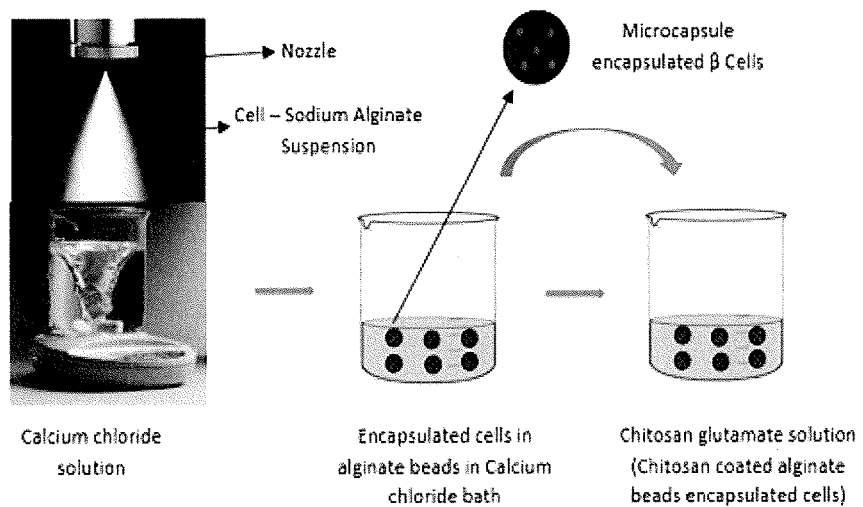
FIG. 48 is a schematic diagram showing a portion of an exemplary embodiment of a method of forming microcapsules.

Diabetes mellitus is a chronic metabolic disease and is one of the primary causes of mortality in well developed countries. The causative factor responsible for none or underproduction of insulin is due to destruction of pancreatic beta cells in type I diabetic patients. The first line therapy is to inject insulin directly to patients or either organ transplant. Our strategy is to enclose (encapsulate) pancreatic beta cells in polymeric microcapsules. This technology works by encapsulating the cells in a semipermeable membrane that allows the entry and exit of small molecules like oxygen and proteins like insulin (Mol wt—6 KDa These cells can produce the protein of interest de novo and deliver the biotherapeutic molecules in the body. The advantage of our proposed strategy over existing therapy would limit the dosing frequency and circumvent the need for organ transplantation Method As shown in FIG. 47 and FIG. 48, microcapsules were prepared by spraying a sucrose-alginate-beta cell suspension mixture into calcium chloride solution using a specialized spray nozzle. Calcium alginate microcapsules containing cells were coated with chitosan glutamate to form a semipermeable membrane at the surface. Various concentrations of sodium alginate, chitosan glutamate and calcium chloride were varied for optimal size and sphericity.

Procedure:

Briefly, alginate solution (1.2% w/v) was prepared and beta islet cells were added to it and allowed to stir for fifteen minutes. After stirring, the alginate cell suspension was then sprayed via 1.40 mm nozzle using a Buchi spraying apparatus in calcium chloride solution (1.5% w/v). Microcapsules in calcium chloride suspension were allowed to stir for fifteen minutes and washed with PBS, centrifuged twice at ×285 g (1200 rpm) to remove the excess calcium ions. Alginate suspension was then transferred to chitosan glutamate (0.5% w/v) solution and stirred further for fifteen minutes and washed with PBS, centrifuged twice at ×285 g (1200 rpm) to remove the excess chitosan and finally transferred in DMEM media and kept in the incubator at 37° C.

Results

Microcapsule Size Vs Gas Flow Rate

Different sized microcapsules can be achieved by spraying the alginate suspension at different gas flow rate. Maintaining the higher gas flow rate leads to reduction in size of microcapsules due to high shear at the tip of nozzle.

Microcapsule Size Distribution

Figure 49:
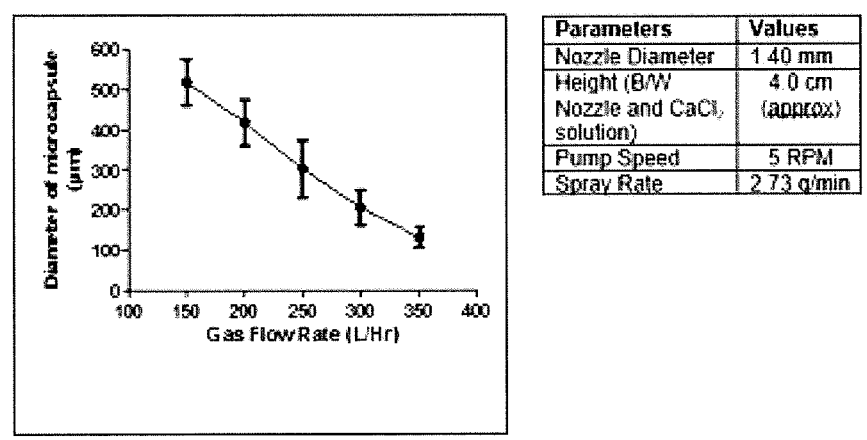
FIG. 49 is a graph of the size of microcapsules (diameter being in μm) plotted at different gas flow rates. Plotted values are mean with ±standard deviation bars.
Figure 50:
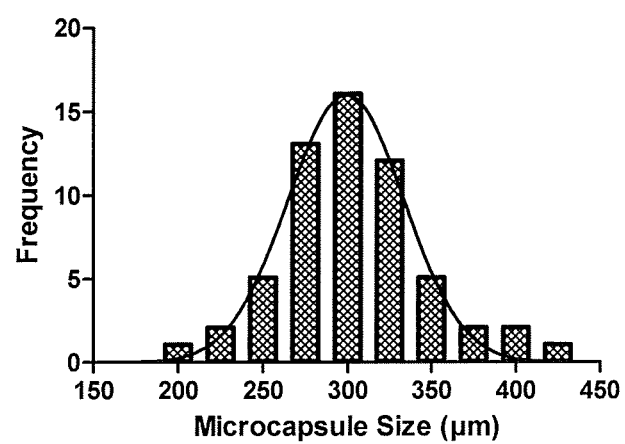
FIG. 50 is a graph of microcapsule size distribution obtained after spraying the alginate suspension at 250 L/Hr.

Microcapsule size was measured by using light optical microscope. The size distribution was evaluated at mean size of 300 μm obtained at a gas flow rate of 250 L/hr. Size distribution was determined by taking a total of 50 microcapsules. FIG. 49 is a graph of the size of microcapsules (diameter being in μm) plotted at different gas flow rates. Plotted values are mean with ±standard deviation bars. FIG. 50 is a graph of microcapsule size distribution obtained after spraying the alginate suspension at 250 L/Hr.

Figure 51:
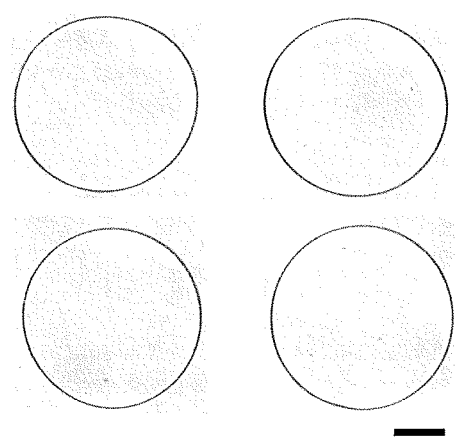
FIG. 51 are microcapsule images taken at 10× after spraying the alginate suspension at 250 L/Hr.

Representative images of empty microcapsules of size 300 μm are shown in FIG. 51. The microcapsule size was found to be in the range of 200-400 μm with a mean of 300 μm.

Fourier Transform Infrared Spectroscopy

Figure 52:
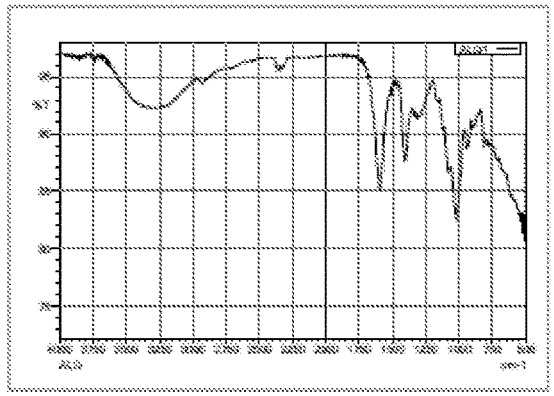
FIG. 52 is a graph of FTIR spectra of sodium alginate.
Figure 53:
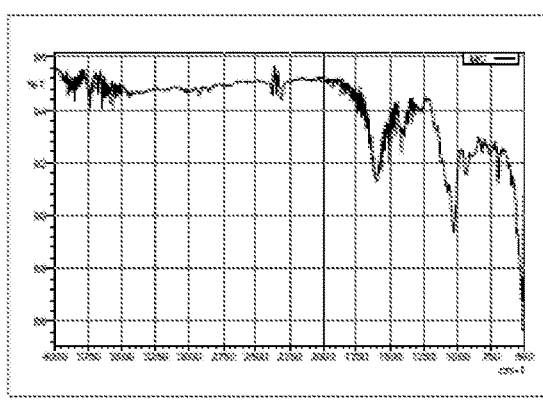
FIG. 53 is a graph of FTIR spectra of alginate microcapsules.

FTIR analysis was performed to confirm the cross linking of alginate microcapsules with calcium chloride used during the fabrication process. Spectra was taken for powdered samples of sodium alginate and compared with the spectra obtained from dried microcapsules. Disappearance of peaks in the region of 3250 cm-1 in alginate microcapsules suggest crosslinking of matrix of alginate microcapsules by calcium chloride added during the fabrication of microcapsules as cross linking agent. FIG. 52 is a graph of FTIR spectra of sodium alginate. FIG. 53 is a graph of FTIR spectra of alginate microcapsules.

Light Microscopy Images

Figure 54A:
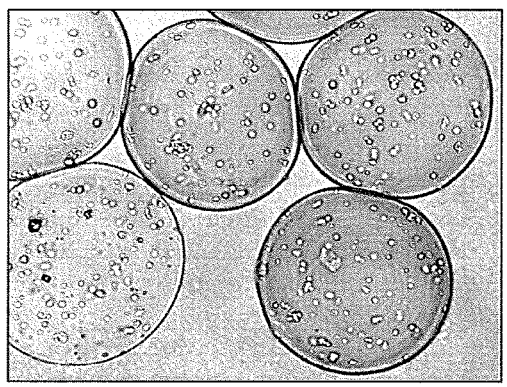
FIG. 54A is a light microscopic image showing clusters of microcapsules encapsulated beta islet pancreatic cells were taken at magnification of 10×.
Figure 54B:
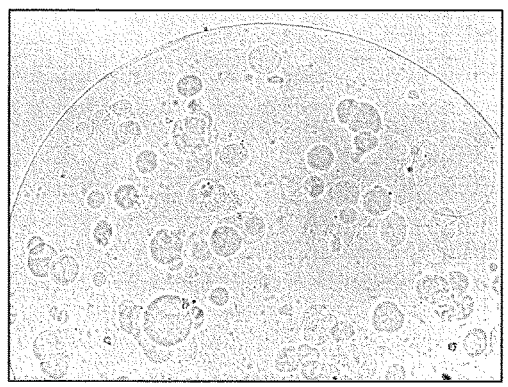
FIG. 54B is a light microscopic image showing clusters of microcapsules encapsulated beta islet pancreatic cells were taken at magnification and 40×.

Images of microcapsules encapsulated pancreatic islet beta cells were taken in light optical microscope at 10×. A drop of microcapsule suspension was placed on slide and coverslip was put on it and observed under microscope. Also the images were taken at 40× which shows that the beta cells present inside the microcapsules in small cluster and not as single cell. The number of cells present in each cluster may range in thousands. FIG. 54A is a light microscopic image showing clusters of microcapsules encapsulated beta islet pancreatic cells were taken at magnification of 10×. FIG. 54B is a light microscopic image showing clusters of microcapsules encapsulated beta islet pancreatic cells were taken at magnification and 40×.

Viability of Beta Islet Cells in Microcapsules

Cell viability in the microcapsules is required for the beta cells to secrete insulin in response to glucose concentration. Cell viability was measured using fluorescent Live/Dead Staining kit. In this assay, the living cells are stained green by the fluorescent calcein that is hydrolyzed from non-fluorescent calcein AM by the intracellular esterases. Ethidium homodimer-1 (EthD-1) enters only the damaged cells and yields increased red fluorescence signal upon binding to nucleic acids. Fluorescent images were taken at different time over a period of thirty days. Stained cells were observed under fluorescent microscope and photographed with a digital camera.

Figure 55:
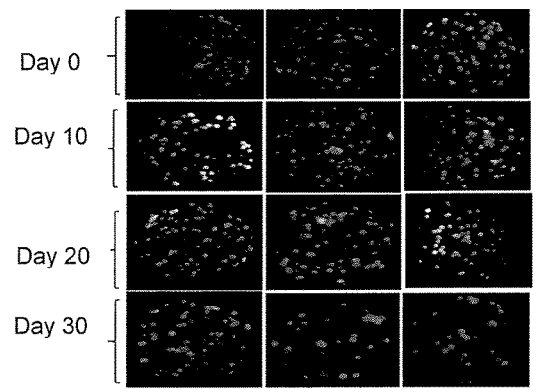
FIG. 55 is a chart of Live dead cell stained images of microcapsules encapsulated pancreatic islet beta cells collected over thirty days period at magnification of 10×.

Procedure—In 96 well plate, 100 μL of sample having microcapsules were added to well and 100 μL staining solution (2 mL of 2 mM stock solution of ethidium bromide and 1 mL of Calcein AM) was added to same well and incubate for 45 minutes. After incubation period, sample was taken on slides and cover with coverslip and analyzed under microscope for live and dead cells. Cells stained green represents live cells and cells stained red represents dead cells. FIG. 55 is a chart of Live dead cell stained images of microcapsules encapsulated pancreatic islet beta cells collected over thirty days period at magnification of 10×.

Nitric Oxide Assay

Figure 56A:
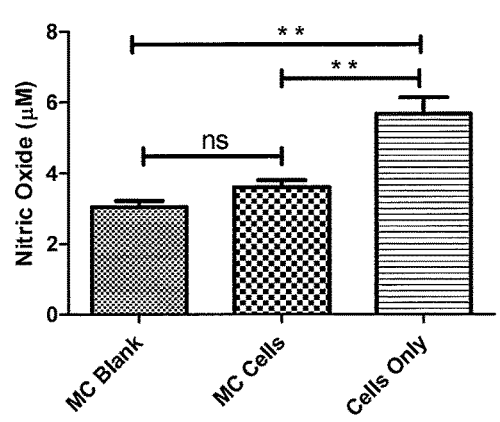
FIG. 56A is a graph of nitric oxide release vs MC Blank (Microcapsules without beta islet pancreatic cells), MC cells (Microcapsules encapsulate beta islet pancreatic cells and Cells only (Unencapsulated cells) ns—not significant, p<0.01 very significant, *p<0.001 extremely significant.
Figure 56B:
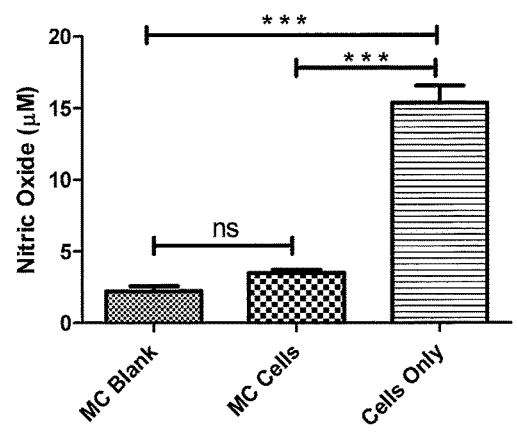
FIG. 56B is a graph of nitric oxide release vs MC Blank (Microcapsules without beta islet pancreatic cells), MC cells (Microcapsules encapsulate beta islet pancreatic cells and Cells only (Unencapsulated cells) ns—not significant, p<0.01 very significant, *p<0.001 extremely significant.
Figure 57:
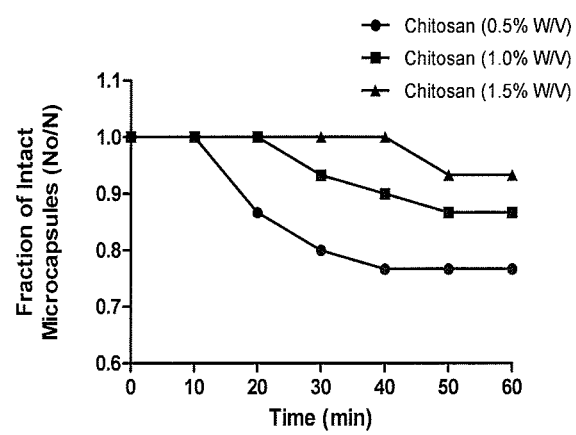
FIG. 57 is graph of short term stability monitored by measuring the fraction of intact microcapsules at different concentration of chitosan used as second layer on alginate microcapsules.

Nitric oxide is an important marker for innate immune response. Antigen presenting cells like dendritic cells release nitric oxide upon exposure to an antigen. In this study we found that there is significantly higher amount of nitric oxide released in the supernatant of dendritic cells exposed to naked beta islet cells compared to microencapsulated cells. FIGS. 56A and 56B are graphs of nitric oxide release vs MC Blank (Microcapsules without beta islet pancreatic cells), MC cells (Microcapsules encapsulate beta islet pancreatic cells and Cells only (Unencapsulated cells) ns—not significant, $p<0.01$ very significant, *$p<0.001$ extremely significant.

Stability of Microcapsules

Stability of microcapsules was done for short term (one hour) also known as explosion assay and long term period (thirty days).

Short Term Stability Studies

Microcapsules fabricated with second layer of coating using chitosan glutamate at different concentrations. Microcapsules were then kept on water for sixty minutes. Second layer of coating at 1.5 w/v of chitosan glutamate was found showing more than 90% of intact microcapsules suggesting enhanced stability. However the stability of microcapsules formed using chitosan glutamate secondary layer at 0.5 W/V and 1.0 W/V showed less than 90% of intact microcapsules.

Long Term Stability Studies

Figure 58:
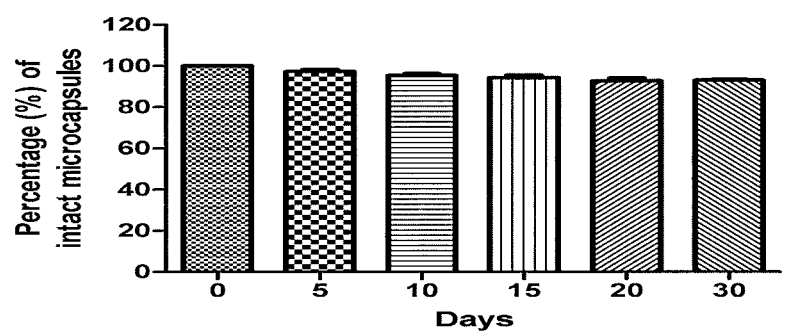
FIG. 58 is a graph of long term stability monitored by measuring the fraction of intact microcapsules.

For long term stability studies, microcapsules fabricated using chitosan glutamate second layer at 1.5% W/V were kept in DMEM media for a period of thirty days. Samples were taken at 5 day interval and put of slides with coverslip and analyzed for percentage of intact microcapsules under light microscope. It was found that percentage of intact microscope was more that 90% on Day 30. FIG. 58 is a graph of long term stability monitored by measuring the fraction of intact microcapsules.

In-Vivo Study

In vivo study was done to evaluate the efficacy of microcapsules in streptozotocin induced diabetic mice model. Animal species used for the study was Swiss Webster and mice were considered diabetic when showing blood glucose levels above 250 mg/dL and non-diabetic when blood glucose levels were below 150 mg/dL.

Figure 59:
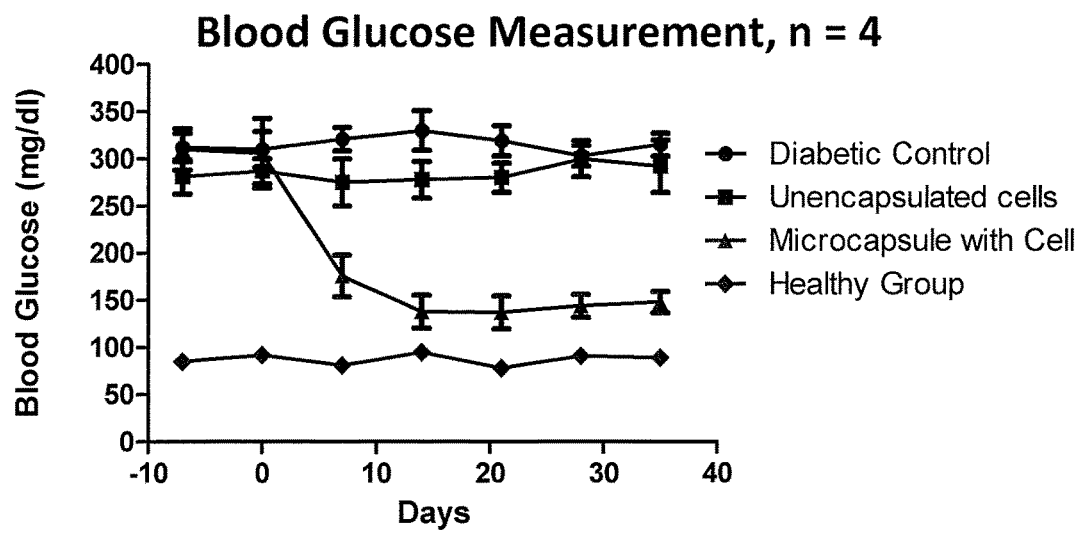
FIG. 59 is a graph of blood glucose levels of different groups in mice measured for 35 days.
Figure 60:
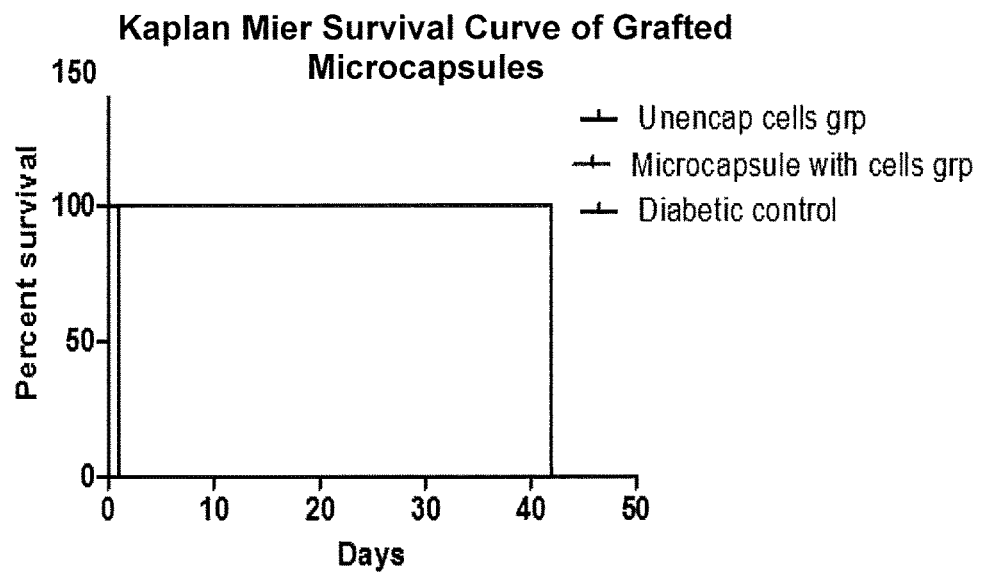
FIG. 60 is a graph of percent graft survival plotted for different groups i.e., Diabetic control, MC cells (Microcapsules encapsulated pancreatic beta islet cells) and Cells only (Unencapsulated cells).

After the induction of diabetes, mice were segregated into different groups based on treatment given. Group received microcapsules encapsulated pancreatic beta islet cells were injected intraperitoneally with microcapsules encapsulating beta cells equivalent to 3 million approximately. Unencapsulated cells group were injected with cells equivalent to 3 million cells. Diabetic control group did not receive any treatment and healthy animals were used in the study for comparison with treatment groups. After giving treatment, blood glucose levels were measured after every 7 days and for a period of thirty five days. As shown in FIG. 59, it was found that the blood glucose levels were below 150 mg/dL in group received microencapsulated beta cells. However, the group received unencapsulated beta cell and diabetic control group show blood glucose level above 250 mg/dL. Blood glucose measurement on Day 42 showed blood glucose levels above 150 mg/dL. Therefore, it was considered that the rejection of injected graft took place and no longer efficient in secreting insulin in response to higher blood glucose levels. FIG. 60 is a Kaplan Miers survival curve shows that the microcapsule group shows graft rejection on day 42. FIG. 60 shows percent graft survival plotted for different groups i.e., Diabetic control, MC cells (Microcapsules encapsulated pancreatic beta islet cells) and Cells only (Unencapsulated cells).

Body Weight Measurement

Figure 61:
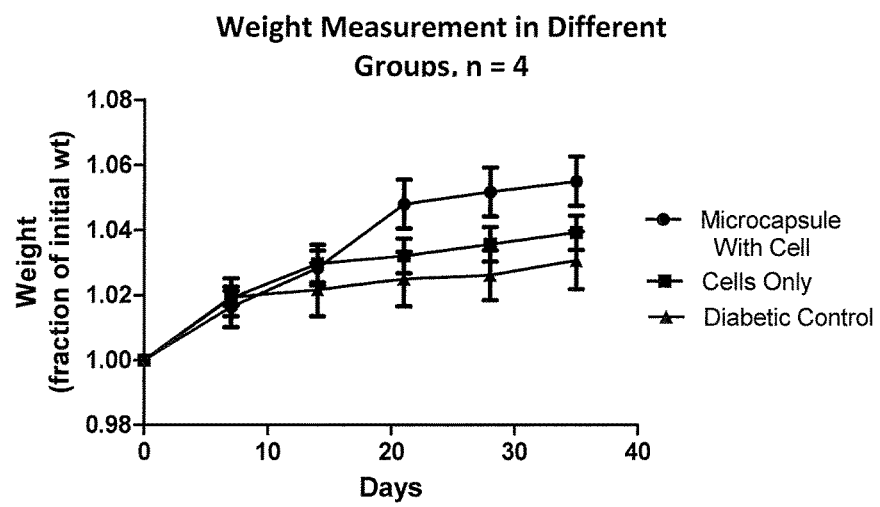
FIG. 61 is a graph of fractional weight of mice in different groups measured for 35 days.

Fractional weight was measured for all mice in different groups studied shown in FIG. 61. Measurement was taken at every 5 day interval and change in weight of mice was observed during the course of study. The data obtained suggest that the increase in weight was higher in groups administered with encapsulated cell in microcapsule. However the diabetic control group not received any treatment shows slight increase in weight.

Immunology Study

Immunology study was performed to ascertain the immune response in mice receiving different treatment. After the rejection of graft in mice received microcapsules encapsulated pancreatic beta cells, mice in all groups sacrificed and immune organs i.e. spleen and lymph nodes were collected. Single cell suspension was prepared by passing the spleen and lymph nodes cells through 40μstrainer. Spleen cells obtained were treated with RBC lysis buffer and centrifuged. This process continues till the cell suspension obtained was colorless. Then, cells of spleen and lymph nodes were seeded in 48 well plate and incubate with markers of CD4 and CD8 cells. After one hour of incubation, cells were washed to remove excess marker and were analyzed using flow cytometry.

Figure 62A:
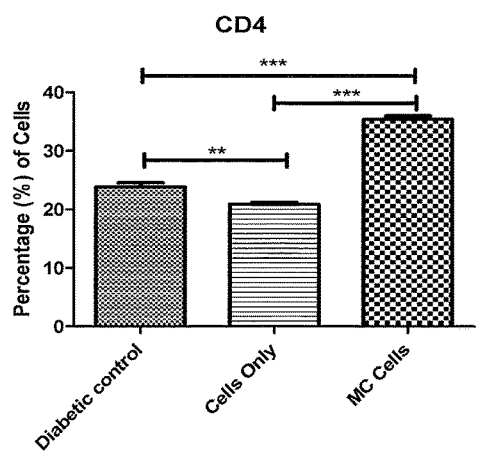
FIG. 62A is a graph of percentage of CD4 and CD8 positive cells plotted for different groups i.e., Diabetic control, MC beta and naked Cells Only. *p<0.05 significant, p<0.01 very significant, *p<0.001 extremely significant (spleen cells).
Figure 62B:
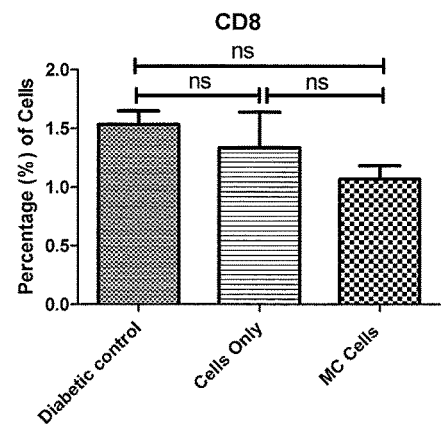
FIG. 62B is a graph of percentage of CD4 and CD8 positive cells plotted for different groups i.e., Diabetic control, MC beta and naked Cells Only. *p<0.05 significant, p<0.01 very significant, *p<0.001 extremely significant (spleen cells).

Results of immune study demonstrate that in spleen cells, the CD4 expression was higher in microcapsule cell group and it was extremely significant ($p<0.001$) compare to diabetic control group and cells only group. However, the expression of CD8 was higher in cells only groups suggesting strong immune response and confirms the protection provided the alginate microcapsules to pancreatic islet beta cells. FIGS. 62A and 62B are graphs of percentage of CD4 and CD8 positive cells plotted for different groups i.e., Diabetic control, MC beta and naked Cells Only. *$p<0.05$ significant, $p<0.01$ very significant, *$p<0.001$ extremely significant (spleen cells). FIG. 62B does not show any statistical significance in expression of CD8 in cells only group and microcapsule group but shows scientific significance.

Figure 63A:
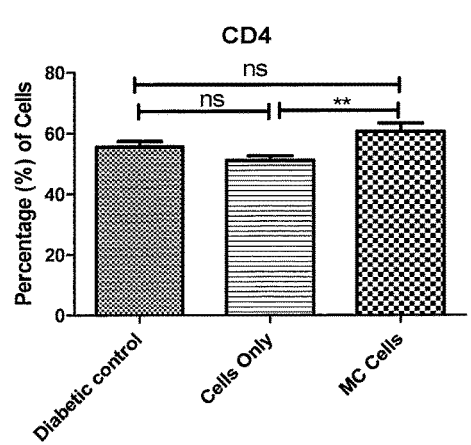
FIG. 63A is a graph of percentage of CD4 positive cells plotted for different groups i.e., Diabetic control, MC beta and naked Cells Only. *p<0.05 significant, p<0.01 very significant, *p<0.001 extremely significant (Lymph node cells).
Figure 63B:
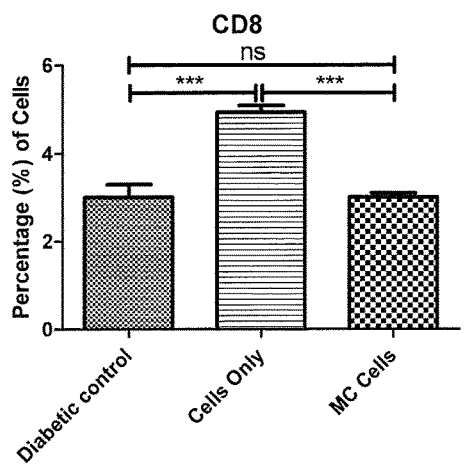
FIG. 63B is a graph of percentage of CD8 positive cells plotted for different groups i.e., Diabetic control, MC beta and naked Cells Only. *p<0.05 significant, p<0.01 very significant, *p<0.001 extremely significant (Lymph node cells).

CD4 expression in lymph nodes cells follows the same trend as in spleen cells and it was higher in microcapsule cell group and it was statistically very significant (p<0.01) in comparison to cells only group as shown in FIGS. 63A and 63B (graphs of percentage of CD4 and CD8 positive cells plotted for different groups i.e., Diabetic control, MC beta and naked Cells Only. *p<0.05 significant, p<0.01 very significant, *p<0.001 extremely significant (Lymph node cells). CD8 expression in lymph nodes also follows similar trend as in spleen cells and it was higher in case of cells only group shows statistically extremely significant (p<0.001) in comparison to microcapsule group and therefore confirms the protective ability of alginate microcapsule to beta islet cells in response to body immune response.

Figure 64:
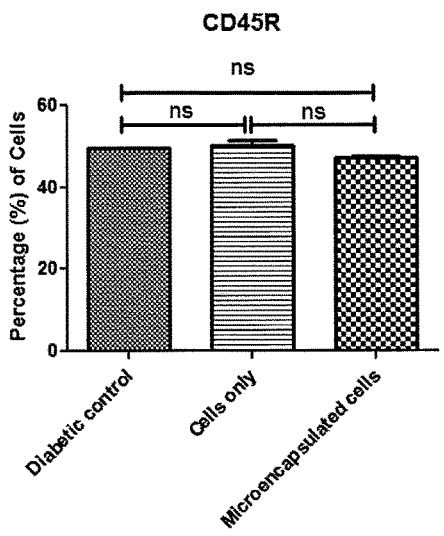
FIG. 64 is a graph of a flow cytometric analysis showing CD45R cell counts in different groups of mice *p<0.05 significant, p<0.01 very significant, *p<0.001 extremely significant.
Figure 65:
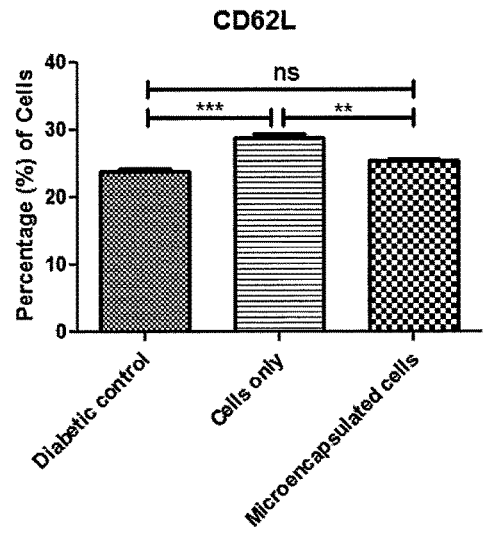
FIG. 65 is a graph of a flow cytometric analysis showing CD62L cell counts in different groups of mice *p<0.05 significant, p<0.01 very significant, *p<0.001 extremely significant.

Expression of CD45R (b220) was also evaluated in order to confirm the antibody response. FIG. 64 is a graph of a flow cytometric analysis showing CD45R cell counts in different groups of mice *p<0.05 significant, p<0.01 very significant, *p<0.001 extremely significant. FIG. 65 is a graph of a flow cytometric analysis showing CD62L cell counts in different groups of mice *p<0.05 significant, p<0.01 very significant, *p<0.001 extremely significant. It was found that antibody secretion similar in all groups and no statistical difference was found. However, the expression of CD62L, a marker of naïve T cells shows higher expression in cells only group and statistical very significant difference (p<0.01) in comparison to microencapsulated cells group demonstrate less immune response developed for beta islet cells encapsulated in microcapsules.

EXAMPLE 6 REFERENCES

1. Hong, C., Carol T. B., Sean M. D. C., Adrienne, K. B., Neal N. I., Collin J. W., and Susan A. S., Long-Term Metabolic Control of Autoimmune Diabetes in Spontaneously Diabetic Nonobese Diabetic Mice by Nonvascularized Microencapsulated Adult Porcine Islets. Transplantation (88) 2 2009 p. 160-169
2. Susan, A. S. Hong, C., M. D., Sean, C., Carol, T. B., B. S., and Collin J. W. M. D. Biocompatibility and Immune Acceptance of Adult Porcine Islets Transplanted Intraperitoneally in Diabetic NOD Mice in Calcium Alginate Poly-L-lysine Microcapsules versus Barium Alginate Microcapsules without Poly-L-lysine. Journal of Diabetes Science and Technology (2) 5 2008 p. 760-767
3. Pia, M., Ilaria, P., Teresa, P., Giuseppe, B., Riccardo, C., Treatment of diabetes mellitus with microencapsulated fetal human liver (FH-B-TPN) engineered cells. Biomaterials (34) 2013 p. 4002-4012
4. Leena, S. K., Marjo, Y., Pyry, T., Antti, M., Ann, M. M., Arto, U., A laboratory-scale device for the straightforward production of uniform, small sized cell microcapsules with long-term cell viability Journal of Controlled Release (152) 2011 p. 376-381
5. Edward, A. P., Devon, M. H., Robert, T., Peter, M. T., Andres, J. G., Vasculogenic bio-synthetic hydrogel for enhancement of pancreatic islet engraftment and function in type 1 diabetes. Biomaterials. (19) 2013 p. 4602-4611
6. ZHOU, D., SUN, A. M., LI, X., MAMUJEE, S. N., VACEK, I., GEORGIOU, J., WHEELER, M. B., In vitro and in vivo evaluation of insulin-producing bTC6-F7 cells in microcapsules. American Physiological Society 1998 p. C1356-C1362
7. Basta, G., Sarchielli, P., Luca, G., Racanicchi, L., Nastruzzi, C., Guido, L., Mancuso, F., Macchiarulo, G., Calabrese, G., Brunetti, P., Calafiore, R., Optimized parameters for microencapsulation of pancreatic islet cells: an in vitro study clueing on islet graft immunoprotection in type 1 diabetes mellitus. Transplant Immunology (13) 2004 p. 289-296
8. Gasserd, O., Sannes, A., Gudmund, S. B., Microcapsules of alginate-chitosan. II. A study of capsule stability and permeability. Biomaterials (20) 1999 p. 773-783
9. Jonna, W., Matti, E., Heli, S., Johanna, K., Marjo, Y., Paavo, H., Arto, U., Alginate-based microencapsulation of retinal pigment epithelial cell line for cell therapy. Biomaterials (29) 2008 p. 869-876
10. Chris, G., Van, H., Henk, J., BusscherPaul, D. V., Fourier transform infrared spectroscopy studies of Alginate-PLL capsules with varying compositions. Wiley Periodicals, 2003 p. 172-178
11. Min, S. P., Eun, Y. L., Gyo, S., Jacek, W., Andrzej, W., and Hi, B. L., Peritoneal transport of glucose in rat. Peritoneal Dialysis International (19) 1999 p. 442-450

Although only a number of exemplary embodiments have been described in detail above, those skilled in the art will readily appreciate that many modifications are possible in the exemplary embodiments without materially departing from the novel teachings and advantages. Accordingly, all such modifications are intended to be included within the scope of this disclosure as defined in the following claims. Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

It should further be noted that any patents, applications and publications referred to herein are incorporated by reference in their entirety.

The invention claimed is:

1. A transdermal delivery system, comprising:
    at least one biodegradable needle comprising
        i. at least one biodegradable polymer,
        ii. at least one sugar; and,
        iii. an encapsulated bioactive material,
    wherein the at least one biodegradable needle contains encapsulated bioactive material such that the bioactive material does not directly contact the at least one biodegradable polymer or the at least one sugar.

2. A transdermal delivery system, comprising:
at least one biodegradable needle comprising
  i. at least one biodegradable polymer, wherein the biodegradable polymer is polydimethylsiloxane;
  ii. at least one sugar; and,
  iii. an encapsulated bioactive material,
wherein the at least one biodegradable needle contains encapsulated bioactive material such that the bioactive material does not directly contact the at least one biodegradable polymer or the at least one sugar.

3. The system of claim 1, wherein the sugar is at least one material selected from the group consisting of maltose and trehalose.

4. The system of claim 1, wherein the bioactive material is at least one material selected from the group consisting of drugs, vaccines, and proteins, and mixtures thereof.

5. A transdermal delivery system, comprising:
at least one biodegradable needle comprising
  i. at least one biodegradable polymer,
  ii. at least one sugar; and,
  iii. an encapsulated bioactive material,
wherein the at least one biodegradable needle contains encapsulated bioactive material such that the bioactive material does not directly contact the at least one biodegradable polymer or the at least one sugar; and,
wherein the bioactive material is at least one material provided in microencapsulated particle form.

6. A transdermal delivery system, comprising:
at least one biodegradable needle comprising
  i. at least one biodegradable polymer;
  ii. at least one sugar; and,
  iii. an encapsulated bioactive material,
wherein the at least one biodegradable needle contains encapsulated bioactive material such that the bioactive material does not directly contact the at least one biodegradable polymer or the at least one sugar; and,
wherein the at least one biodegradable microneedle is able to degrade within 12 minutes after delivery to a subject's skin.

7. A transdermal delivery system, comprising:
at least one biodegradable needle comprising
  i. at least one biodegradable polymer;
  ii. at least one sugar; and,
  iii. an encapsulated bioactive material,
wherein the at least one biodegradable needle contains encapsulated bioactive material such that the bioactive material does not directly contact the at least one biodegradable polymer or the at least one sugar; and,
wherein the bioactive material is in the form of microencapsulated material having an average particle size in a range of 0.01-50 µm.

8. A transdermal delivery system, comprising:
at least one biodegradable needle comprising
  i. at least one biodegradable polymer;
  ii. at least one sugar; and,
  iii. an encapsulated bioactive material,
wherein the at least one biodegradable needle contains encapsulated bioactive material such that the bioactive material does not directly contact the at least one biodegradable polymer or the at least one sugar; and,
wherein the bioactive material is in the form of microencapsulated material having an average particle size in a range of 1-4 µm.

9. The system of claim 1, further comprising an adjuvant.

10. The system of claim 1, wherein the bioactive material is at least one material selected from the group consisting of a vaccine to gonorrhea, a vaccine to an antigen expressed by breast cancer cells, a vaccine to influenza, a vaccine to human papilloma virus, and a vaccine to respiratory syncytial virus.

11. The delivery system of claim 1, wherein each biodegradable needle is solid.

12. The delivery system of claim 1, wherein each biodegradable needle is hollow.

* * * * *